United States Patent [19]

Fishbine et al.

[11] Patent Number: 4,811,414
[45] Date of Patent: Mar. 7, 1989

[54] METHODS FOR DIGITALLY NOISE AVERAGING AND ILLUMINATION EQUALIZING FINGERPRINT IMAGES

[75] Inventors: Glenn M. Fishbine, Eden Praire; Mark S. Ransom; Daniel E. Germann, both of Minneapolis, all of Minn.

[73] Assignee: C.F.A. Technologies, Inc., St. Louis, Minn.

[21] Appl. No.: 20,331

[22] Filed: Feb. 27, 1987

[51] Int. Cl.$^4$ .................... G06K 9/00; G06K 9/56
[52] U.S. Cl. .................................. 382/52; 382/4; 382/54; 358/163
[58] Field of Search .................. 382/4, 5, 52, 54; 358/163, 166

[56] References Cited

U.S. PATENT DOCUMENTS

| | | | |
|---|---|---|---|
| 3,200,701 | 8/1965 | White | 88/14 |
| 3,478,658 | 11/1969 | Yow-Jiun et al. | 95/1.1 |
| 3,482,498 | 12/1969 | Becker | 95/12 |
| 3,581,282 | 5/1971 | Altman | 340/149 |
| 3,614,737 | 10/1971 | Sadowsky | 340/146.3 |
| 3,639,905 | 2/1972 | Yaida et al. | 340/149 |
| 3,648,240 | 3/1972 | Jacoby et al. | 340/146.3 E |
| 3,743,772 | 7/1973 | Pieters et al. | 358/163 |
| 3,944,978 | 3/1976 | Jensen et al. | 340/146.3 E |
| 3,968,476 | 7/1976 | McMahon | 340/146.3 E |
| 3,975,711 | 8/1976 | McMahon | 340/146.3 E |
| 4,047,152 | 9/1977 | Giuliano | 382/52 |
| 4,074,231 | 2/1978 | Yajima et al. | 382/54 |
| 4,107,775 | 8/1978 | Ott | 364/413 |
| 4,120,585 | 10/1978 | DePalma et al. | 356/71 |
| 4,151,512 | 4/1979 | Riganati et al. | 340/146 |
| 4,186,378 | 1/1980 | Moulton | 340/146.3 E |
| 4,205,341 | 5/1980 | Mitsuya et al. | 382/54 |
| 4,206,441 | 6/1980 | Kondo | 340/146.3 E |
| 4,227,805 | 10/1980 | Schiller | 356/71 |
| 4,236,082 | 11/1980 | Butler | 250/461 R |
| 4,238,768 | 12/1980 | Mitsuya et al. | 382/52 |
| 4,246,568 | 1/1981 | Peterson | 340/146.3 E |
| 4,322,163 | 3/1982 | Schiller | 356/71 |
| 4,340,300 | 7/1982 | Ruell | 356/71 |
| 4,357,597 | 11/1982 | Butler | 340/146.3 E |
| 4,385,831 | 5/1983 | Ruell | 356/71 |
| 4,428,670 | 1/1984 | Ruell et al. | 356/71 |
| 4,429,413 | 1/1984 | Edwards | 382/4 |
| 4,455,083 | 6/1984 | Elmes | 356/7 |
| 4,544,267 | 10/1985 | Schiller | 356/71 |
| 4,553,165 | 11/1985 | Bayer | 358/166 |
| 4,553,837 | 11/1985 | Marcus | 356/71 |
| 4,569,080 | 2/1986 | Schiller | 382/4 |
| 4,573,070 | 2/1986 | Cooper | 358/166 |
| 4,577,235 | 3/1986 | Kannapell et al. | 382/52 |
| 4,652,116 | 3/1987 | Rios | 355/40 |
| 4,668,995 | 5/1987 | Chen et al. | 382/52 |

Primary Examiner—Leo H. Boudreau
Assistant Examiner—Donald J. Daley
Attorney, Agent, or Firm—Kinney & Lange

[57] ABSTRACT

Methods for operating a programmable digital computer to enhance images of fingerprints represented by an array of pixel values. Methods for noise averaging, illumination equalizing, directional filtering, unhairing, curvature correcting, and scale correcting a fingerprint image are disclosed.

7 Claims, 28 Drawing Sheets

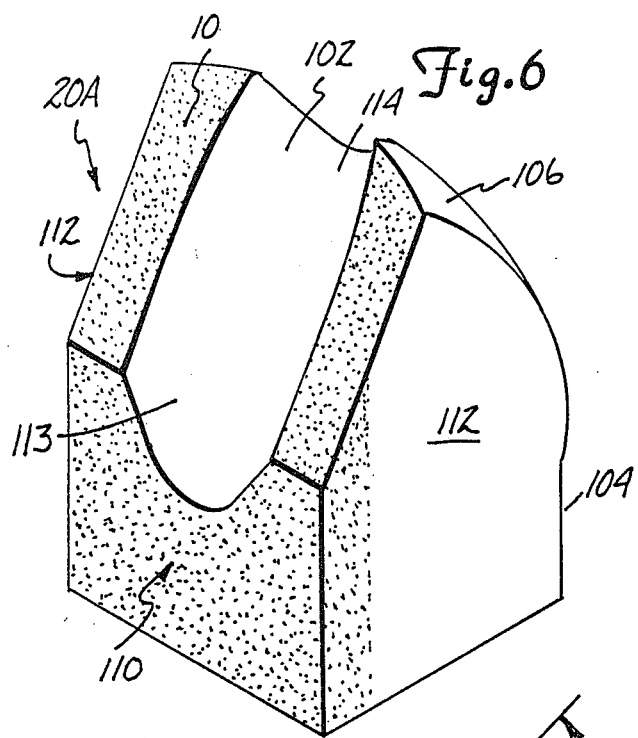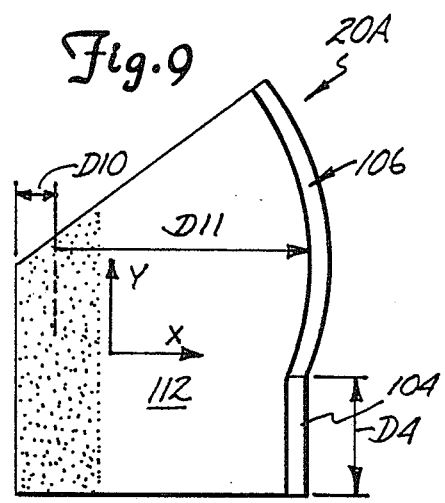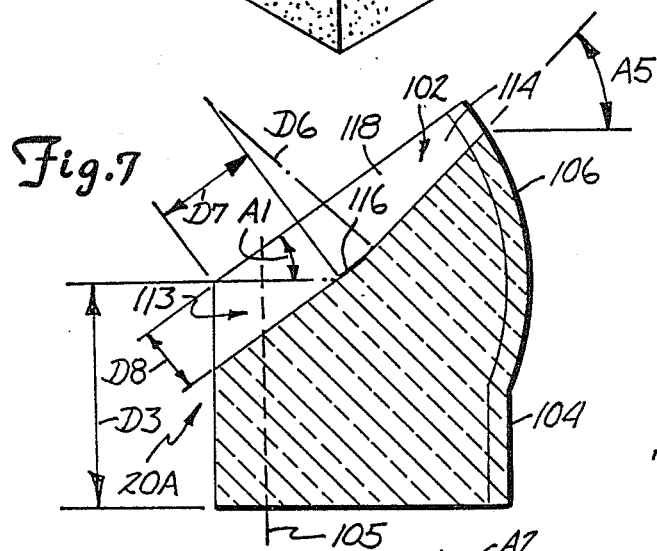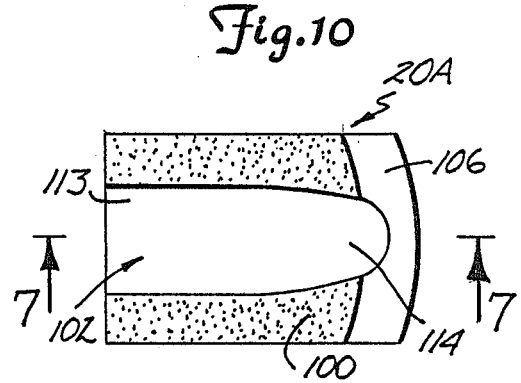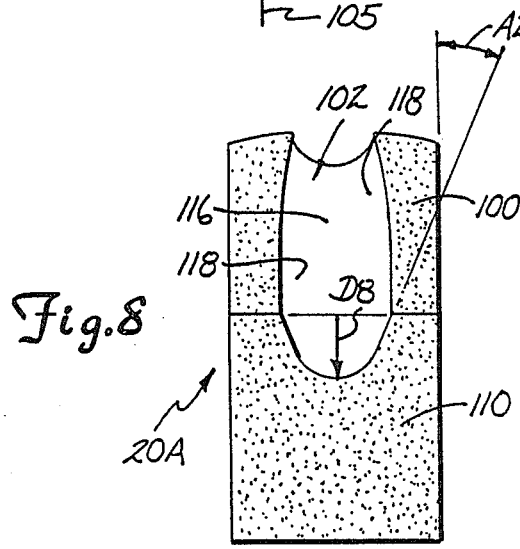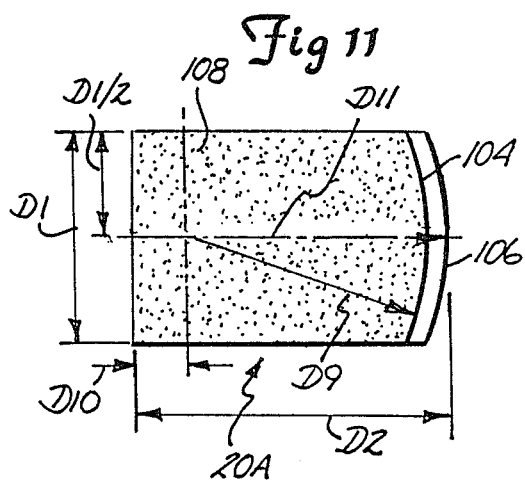

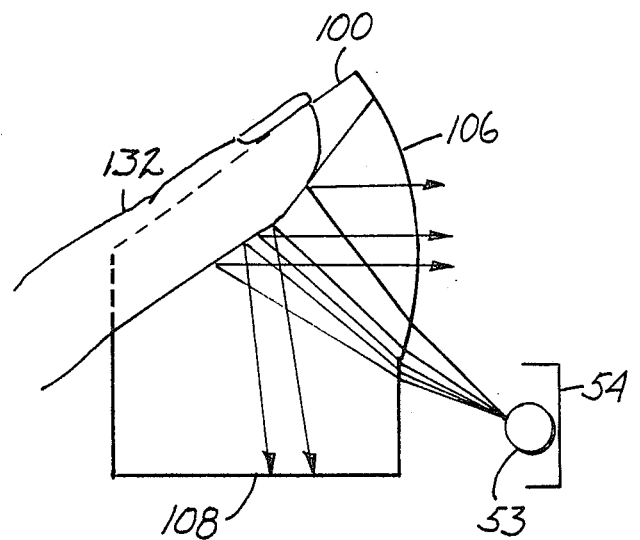
Fig. 13
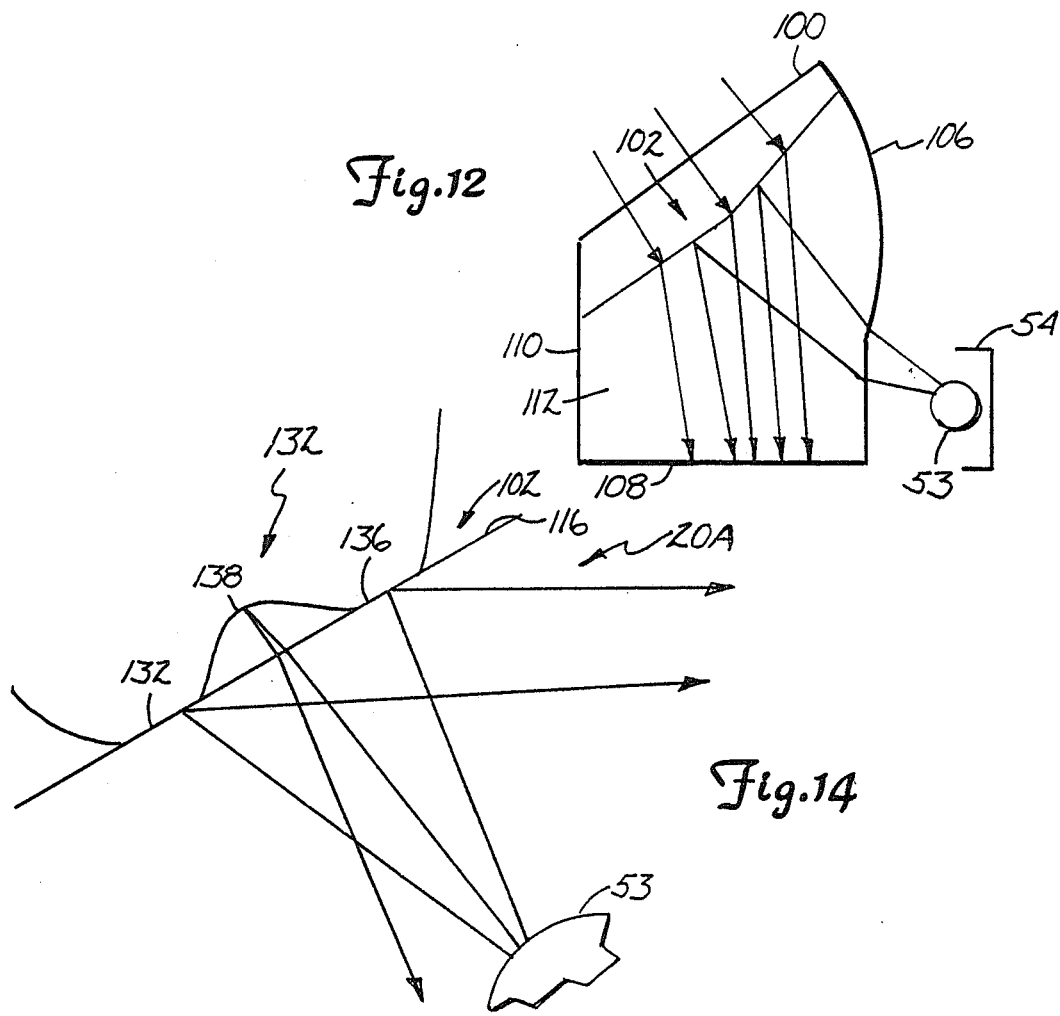
Fig. 12
Fig. 14

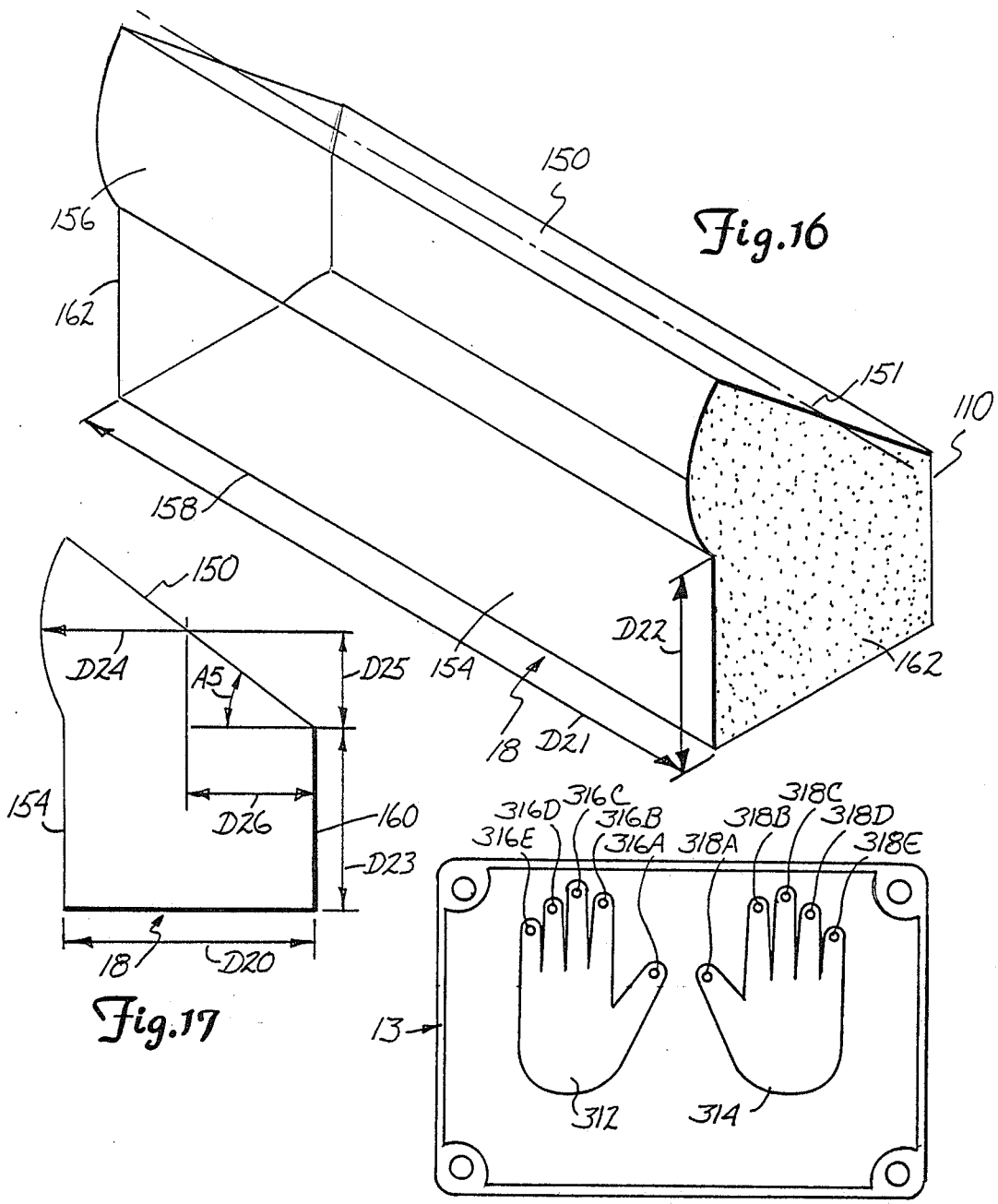
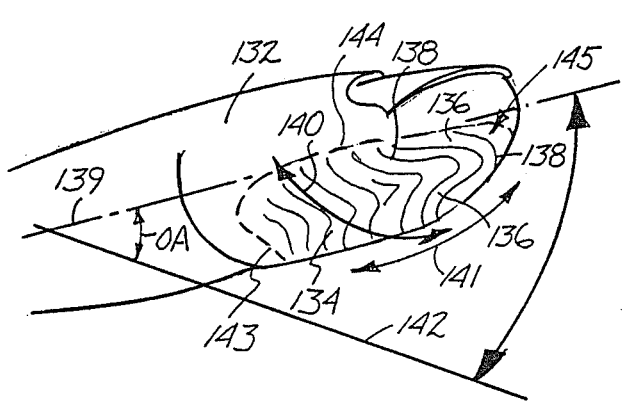

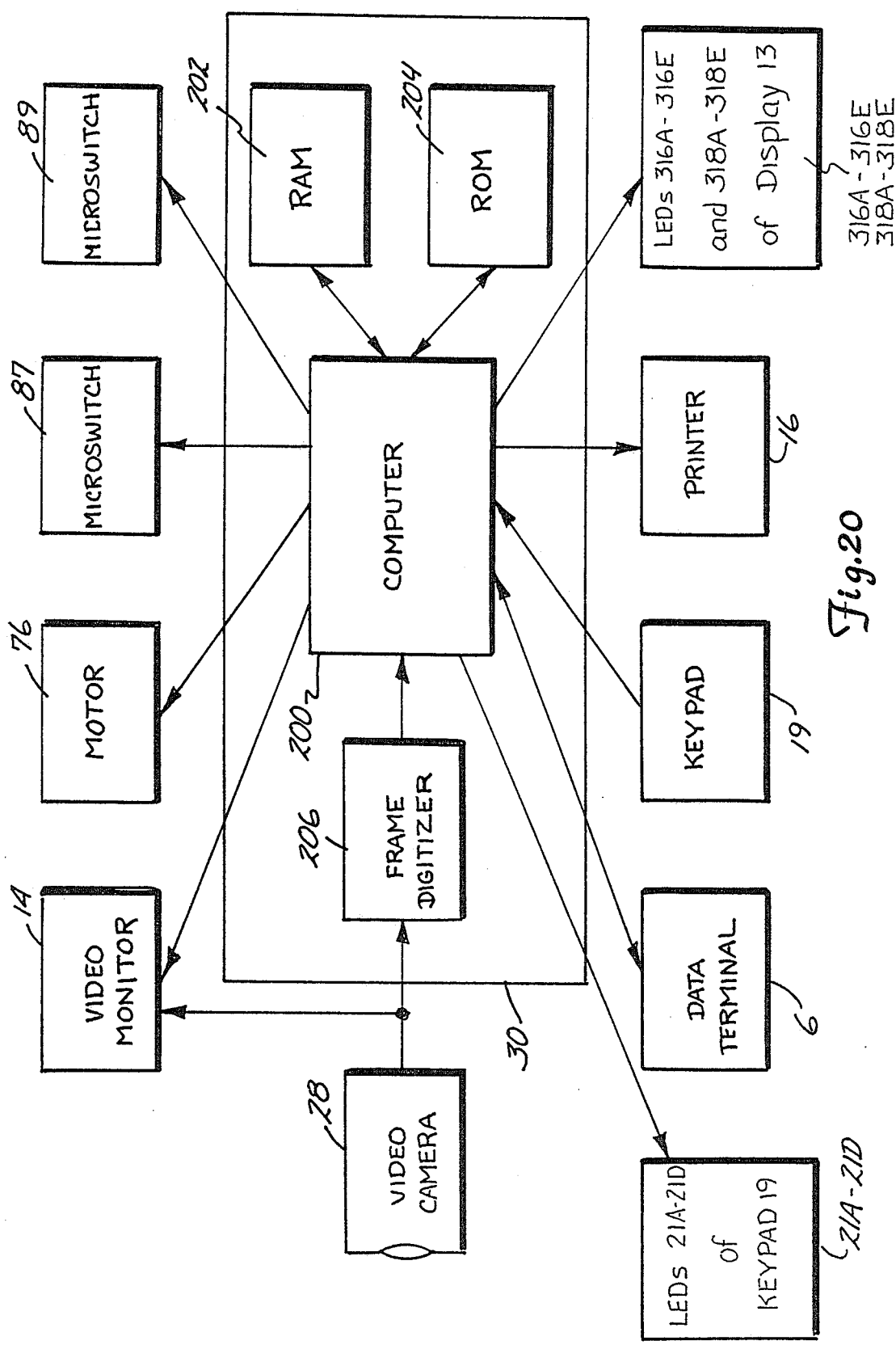

| PV1,1$_I$ PL1,1 | PV1,2$_I$ | PV1,3$_I$ | PV1,4$_I$ | PV1,5$_I$ | PV1,6$_I$ | PV1,7$_I$ | ... | | PV1,M$_1$ |
|---|---|---|---|---|---|---|---|---|---|
| PV2,1$_I$ | PV2,2$_I$ | PV2,3$_I$ | | | | | | | |
| PV3,1$_I$ | PV3,2$_I$ | PV3,3$_I$ | | | | | | | |
| PV4,1$_I$ | | | PV$n$-1, $m$-1$_I$ | PV$n$-1, $m_I$ | PV$n$-1, $m$+1$_I$ | | | | |
| PV5,1$_I$ PL5,1 | | PL$N$,M | PV$n$, $m$-1$_I$ | PV$n$, $m_I$ | PV$n$, $m$+1$_I$ | | | | |
| PV6,1$_I$ | | PL$n$, $m$-1 | PV$n$+1, $m$-1$_I$ | PV$n$+1, $m_I$ | PV$n$+1, $m$+1$_I$ | | | | |
| PV7,1$_I$ | | | | | | | | | |

| PL$N$-1,1 PV$N$-1, 1$_I$ | | | | | | | | PV$N$-1, M-1$_I$ | PV$N$-1, M$_I$ |
|---|---|---|---|---|---|---|---|---|---|
| PL$N$,1 PV$N$,1$_I$ | PV$N$,2$_I$ | PV$N$,3$_I$ | PV$N$,4$_I$ | PV$N$,5$_I$ | PV$N$,6$_I$ | PV$N$,7$_I$ | ... | PV$N$, M-1$_I$ | PV$N$, M$_I$ |

PLN-1,M

PLN,M

| $PV1,1_N$ | $PV1,2_N$ | $PV1,3_N$ | $PV1,4_N$ | $PV1,5_N$ | $PV1,6_N$ | $PV1,7_N$ | ... | $PV1, M-1_N$ | $PV1,M_N$ |
|---|---|---|---|---|---|---|---|---|---|
| $PV2,1_N$ | $PV2,2_N$ | $PV2,3_N$ | | | | | | | |
| $PV3,1_N$ | $PV3,2_N$ | $PV3,3_N$ | | | | | | | |
| $PV4,1_N$ | | | $PVn-1, m-1_N$ | $PVn-1, m_N$ | $PVn-1, m+1_N$ | | | | |
| $PV5,1_N$ | | | $PVn, m-1_N$ | $PVn, m_N$ | $PVn, m+1_N$ | | | | |
| $PV6,1_N$ | | | $PVn+1, m-1_N$ | $PVn+1, m_N$ | $PVn+1, m+1_N$ | | | | |
| $PV7,1_N$ | | | | | | | | | |
| $PVN-1, 1_N$ | | | | | | | | $PVN-1, M-1_N$ | $PVN-1, M_N$ |
| $PVN,1_M$ | $PVN2_M$ | $PVN3_N$ | $PVN4_N$ | $PVN5_N$ | $PVN6_N$ | $PVN7_N$ | ... | $PVN, M-1_N$ | $PVN, M_N$ |

NAA

| $PV1,1_E$ | $PV1,2_E$ | $PV1,3_E$ | $PV1,4_E$ | $PV1,5_E$ | $PV1,6_E$ | $PV1,7_E$ | ... | $PV1, M-1_E$ | $PV1, M_E$ |
|---|---|---|---|---|---|---|---|---|---|
| $PV2,1_E$ | | | | | | | | | |
| $PV3,1_E$ | | | | | | | | | |
| $PV4,1_E$ | | | $PVn-1, m-1_E$ | $PVn-1, m_E$ | $PVn-1, m+1_E$ | | | | |
| $PV5,1_E$ | | | $PVn, m-1_E$ | $PVn, m_E$ | $PVn, m+1_E$ | | | | |
| $PV6,1_E$ | | | $PVn+1, m-1_E$ | $PVn+1, m_E$ | $PVn+1, m+1_E$ | | | | |
| $PV7,1_E$ | | | | | | | | | |

⋮

| $PVN-1, 1_E$ | | | | | | | | $PVN-1, M-1_E$ | $PVN-1, M_E$ |
|---|---|---|---|---|---|---|---|---|---|
| $PVN,1_E$ | $PVN2_E$ | $PVN3_E$ | $PVN4_E$ | $PVN5_E$ | $PVN6_E$ | $PVN7_E$ | ... | $PVN, M-1_E$ | $PVN, M_E$ |

IEA

Fig. 23

| PV1,1$_N$ | PV1,2$_N$ | PV1,3$_N$ | PV1,4$_N$ | PV1,5$_N$ | PV1,6$_N$ | PV1,7$_N$ | ... | PV1, M-1$_N$ | PV1, M$_N$ |
|---|---|---|---|---|---|---|---|---|---|
| PV2,1$_N$ | PV2,2$_N$ | PV2,3$_N$ | | | | | | | |
| PV3,1$_N$ | PV3,2$_N$ | PV3,3$_N$ | | | | | | | |
| PV4,1$_N$ | | | PV$n$-1, $m$-1$_N$ | PV$n$-1, $m_N$ | PV$n$-1, $m$+1$_N$ | | | | |
| PV5,1$_N$ | | | PV$n$, $m$-1$_N$ | PV$n$, $m_N$ | PV$n$, $m$+1$_N$ | | | | |
| PV6,1$_N$ | | | PV$n$+1, $m$-1$_N$ | PV$n$+1, $m_N$ | PV$n$+1, $m$+1$_N$ | | | | |
| PV7,1$_N$ | | | | | | | | | |
| ... | | | | | | | | ... | ... |
| PVN-1, 1$_N$ | | | | | | | | PVN-1, M-1$_N$ | PVN-1, M$_N$ |
| PVN,1$_M$ | PVN2$_M$ | PVN3$_N$ | PVN4$_N$ | PVN5$_N$ | PVN6$_N$ | PVN7$_N$ | ... | PVN, M-1$_N$ | PVN, M$_N$ |

NAA

| | | | 230A | 230B | | | | | |
|---|---|---|---|---|---|---|---|---|---|
| $PV1,1_E$ | $PV1,2_E$ | $PV1,3_E$ | $PV1,4_E$ | $PV1,5_E$ | $PV1,6_E$ | $PV1,7_E$ | ... | $PV1, M-1_E$ | $PV1,M_E$ |
| 232A $PV2,1_E$ | $PV2,2_E$ | $PV2,3_E$ | $PV2,4_E$ | $PV2,5_E$ | $PV2,6_E$ | $PV2,7_E$ | | | 232F |
| $PV3,1_E$ | $PV3,2_E$ | $PV3,3_E$ | $PV3,4_E$ | $PV3,5_E$ | $PV3,6_E$ | $PV3,7_E$ | | | |
| $PV4,1_E$ | $PV4,2_E$ | $PV4,3_E$ | $PV4,4_E$ | $PV4,5_E$ | $PV4,6_E$ | $PV4,7_E$ | | | 230E |
| $PV5,1_E$ | | | 230G $PVn-1, m-1_E$ | $PVn-1, m_E$ | $PVn-1, m+1_E$ | | | | |
| 230F $PV6,1_E$ | | 232H | | $PVn, m-1_E$ | $PVn, m_E$ | $PVn, m+1_E$ | | | |
| $PV7,1_E$ | | | | $PVn+1, m-1_E$ | $PVn+1, m_E$ | $PVn+1, m+1_E$ | | | |
| $PVN-1, 1_E$ | | | | | | | | $PVN-1, M-1_E$ | $PVN-1, M_E$ |
| $PVN,1_E$ | $PVN,2_E$ | $PVN,3_E$ | $PVN,4_E$ | $PVN,5_E$ | $PVN,6_E$ | $PVN,7_E$ | ... | $PVN, M-1_E$ | $PVN, M_E$ |

IEA

Fig. 27

| $PV1,1_U$ | $PV1,2_U$ | $PV1,3_U$ | $PV1,4_U$ | $PV1,5_U$ | $PV1,6_U$ | $PV1,7_U$ | ... | | $PV1,M_U$ |
|---|---|---|---|---|---|---|---|---|---|
| $PV2,1_U$ | | | | | | | | | |
| $PV3,1_U$ | | | | | | | | | |
| $PV4,1_U$ | | | $PVn-1, m-1_U$ | $PVn-1, m_U$ | $PVn-1, m+1_U$ | | | | |
| $PV5,1_U$ | | | $PVn, m-1_U$ | $PVn, m_U$ | $PVn, m+1_U$ | | | | |
| $PV6,1_U$ | | | $PVn+1, m-1_U$ | $PVn+1, m_U$ | $PVn+1, m+1_U$ | | | | |
| $PV7,1_U$ | | | | | | | | | |
| ... | | | | | | | | ... | |
| $PVN-1, 1_U$ | | | | | | | | $PVN-1, M-1_U$ | $PVN-1, M_U$ |
| $PVN,1_U$ | $PVN,2_U$ | $PVN,3_U$ | $PVN,4_U$ | $PVN,5_U$ | $PVN,6_U$ | $PVN,7_U$ | ... | $PVN, M-1_U$ | $PVN, M_U$ |

| $PV1,1_C$ | $PV1,2_C$ | $PV1,3_C$ | $PV1,4_C$ | $PV1,5_C$ | $PV1,6_C$ | $PV1,7_C$ | ... | | $PV1,M_C$ |
|---|---|---|---|---|---|---|---|---|---|
| $PV2,1_C$ | | | | | | | | | |
| $PV3,1_C$ | | | | | | | | | |
| $PV4,1_C$ | | | $PVn-1, m-1_C$ | $PVn-1, m_C$ | $PVn-1, m+1_C$ | | | | |
| $PV5,1_D$ | | | $PVn, m-1_C$ | $PVn, m_C$ | $PVn, m+1_C$ | | | | |
| $PV6,1_D$ | | | $PVn+1, m-1_C$ | $PVn+1, m_C$ | $PVn+1, m+1_C$ | | | | |
| $PV7,1_C$ | | | | | | | | | |

⋮                                                                       ⋮

| $PVN-1, 1_C$ | | | | | | | ... | $PVN-1, M-1_C$ | $PVN-1, M_C$ |
|---|---|---|---|---|---|---|---|---|---|
| $PVN,1_C$ | $PVN,2_C$ | $PVN,3_C$ | $PVN,4_C$ | $PVN,5_C$ | $PVN,6_C$ | $PVN,7_C$ | | $PVN, M-1$ | $PVN, M_C$ |

CCA ↗

Fig. 31

| HORIZONTALLY SCALED ARRAY HA | VERTICALLY SCALED ARRAY VA |
|---|---|
| $PVn,1_H$ | PVMAX |
| $PVn,2_H$ | PVMAX |
| ⋮ | ⋮ |
| $PVn,300_H$ | $PVn,300_V$ |
| $PVn,301_H$ | $PVn,301_V$ |
| $PVn,302_H$ | $PVn,301_V$ |
| $PVn,303_H$ | $PVn,301_V$ |
| $PVn,304_H$ | $PVn,301_V$ |
| $PVn,305_H$ | $PVn,302_V$ |
| $PVn,306_H$ | $PVn,302_V$ |
| $PVn,307_H$ | $PVn,302_V$ |
| $PVn,308_H$ | $PVn,303_V$ |
| $PVn,309_H$ | $PVn,304_V$ |
| $PVn,310_H$ | $PVn,305_V$ |
| $PVn,311_H$ | $PVn,305_V$ |
| $PVn,312_H$ | $PVn,306_V$ |
| $PVn,313_H$ | $PVn,307_V$ |
| $PVn,314_H$ | $PVn,309_V$ |
| $PVn,315_H$ | $PVn,310_V$ |
| $PVn,316_H$ | $PVn,311_V$ |
| ⋮ | ⋮ |
| $PVn,M-1_H$ | PVMAX |
| $PVn,M_H$ | PVMAX |

Fig. 40

| VERTICALLY SCALED ARRAY VA | CURVATURE CORRECTED ARRAY CCA |
|---|---|
| $PV1,m_V$ | PVMAX |
| $PV2,m_V$ | PVMAX |
| ⋮ | ⋮ |
| $PV200,m_V$ | $PV200,m_C$ |
| $PV201,m_V$ | $PV201,m_C$ |
| $PV202,m_V$ | $PV201,m_C$ |
| $PV203,m_V$ | $PV201,m_C$ |
| $PV204,m_V$ | $PV201,m_C$ |
| $PV205,m_V$ | $PV202,m_C$ |
| $PV206,m_V$ | $PV202,m_C$ |
| $PV207,m_V$ | $PV202,m_C$ |
| $PV208,m_V$ | $PV203,m_C$ |
| $PV209,m_V$ | $PV204,m_C$ |
| $PV210,m_V$ | $PV205,m_C$ |
| $PV211,m_V$ | $PV205,m_C$ |
| $PV212,m_V$ | $PV206,m_C$ |
| $PV213,m_V$ | $PV207,m_C$ |
| $PV214,m_V$ | $PV209,m_C$ |
| $PV215,m_V$ | $PV210,m_C$ |
| $PV216,m_U$ | $PV211,m_C$ |
| ⋮ | ⋮ |
| $PVN-1,m_V$ | PVMAX |
| $PVN,m_V$ | PVMAX |

| | | | | | | | | | |
|---|---|---|---|---|---|---|---|---|---|
| $PV1,M_H$ | | | | | | | ... | $PVN-1, M_H$ | $PVN, M_H$ |
| $PV1,M-1_H$ | | | | | | | ... | $PVN-1, M-1_H$ | $PVN, M-1_H$ |

| | | | | | | | | | |
|---|---|---|---|---|---|---|---|---|---|
| $PV1,7_H$ | | | | | | | ... | | $PVN,7_H$ |
| $PV1,6_H$ | | | | $PVn-1, m+1_H$ | $PVn, m+1_H$ | $PVn+1, m+1_H$ | | | $PVN,6_H$ |
| $PV1,5_H$ | | | | $PVn-1, m_H$ | $PVn, m_H$ | $PVn+1, m_H$ | | | $PVN,5_H$ |
| $PV1,4_H$ | | | | $PVn-1, m-1_H$ | $PVn, m-1_H$ | $PVn+1, m-1_H$ | | | $PVN,4_H$ |
| $PV1,3_H$ | | | | | | | | | $PVN,3_H$ |
| $PV1,2_H$ | | | | | | | | | $PVN,2_H$ |
| $PV1,1_H$ | $PV2,1_H$ | $PV3,1_H$ | $PV4,1_H$ | $PV5,1_H$ | $PV6,1_H$ | $PV7,1_H$ | ... | $PVN-1,1_H$ | $PVN,1_H$ |

HA

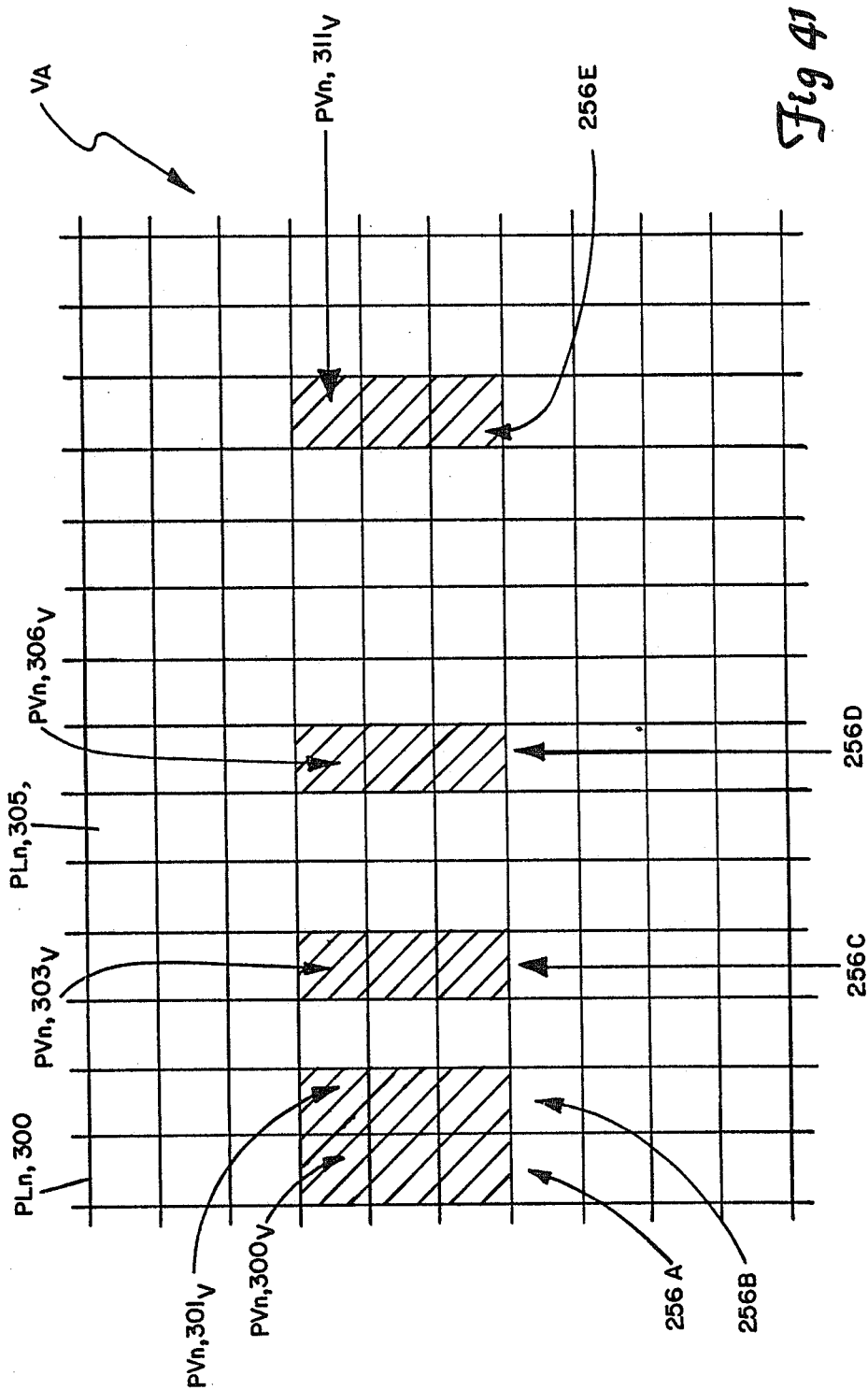

TENPRINTER Data Capture System       300

1. Clear system for new card.
2. Start fingerprint capture.
3. Enter/change demographic function.
4. Print card.
5. Options.

Enter number, then press RETURN key:

TENPRINTER Fingerprint Processing Choices

0. Exit.
1. Capture Prints.            *Fig.46*
2. Recapture Prints.
3. Options.

Enter number, then press RETURN key:

FIG 41

| | |
|---|---|
| Name: Last_____ First_____ Middle_____ | |
| Date of Birth (DOB)_____ Place of Birth_____ | |
| Sex___Race___Hgt_____ Wgt_____Eyes____ Hair_____ | |
| Aliases_____ Contributor (ORI)_____ | |
| Your no. (OCA)_____FBI no. (FBI)_____ | |
| SID no. (SID)_____Social Security no. (SOC)_____ | |
| Today's date_____ Date Arrested or Received (DOA)_____ | |
| Charge_____ Final Disposition_____ | |

| DEPARTMENT INFORMATION | DEMOGRAPHIC INFORMATION | | | |
|---|---|---|---|---|
| R. THUMB | R. INDEX | R. MIDDLE | R. RING | R. LITTLE |
| L. THUMB | L. INDEX | L. MIDDLE | L. RING | L. LITTLE |
| LEFT FOUR FINGERS SIMULTANEOUSLY | | L. THUMB | R. THUMB | RIGHT FOUR FINGERS SIMULTANEOUSLY |

METHODS FOR DIGITALLY NOISE AVERAGING AND ILLUMINATION EQUALIZING FINGERPRINT IMAGES

Reference is hereby made to co-pending applications entitled Optical Fingerprinting System and Optical Devices for Providing Fingerprint Images, filed on even date herewith.

BACKGROUND OF THE INVENTION

1. Field of the Invention.

The present invention relates to computer processing of fingerprint images

2. Description of the Prior Art.

Over the years, the most commonly used technique for obtaining fingerprints has been to apply ink to the tip of individual fingers and roll the inked fingertip at an appropriate location on an applicant card to produce the "rolled" fingerprint. Plain or "slap" prints, which are the simultaneous fingerprinting of the index, middle, ring, and little fingers of a hand, are taken by inking the tips of these fingers and simultaneous pressing the inked fingertips on the applicant card at the appropriate location. While these inking procedures will usually provide satisfactory images, they have their drawbacks. The inking procedure is messy. Several attempts are often required in order to obtain an acceptable fingerprint. Perhaps even a bigger drawback of this system is that the printed images are not easily adaptable to computerized storage and processing techniques, inhibiting cooperation and fingerprint data transfer between various police agencies.

Optical fingerprinting systems which optically generate fingerprint images are also in use. Several such optical fingerprinting systems are disclosed in the U.S. Pat. Nos. to Becker 3,482,498, McMahon 3,975,711, White 3,200,701, Schiller 4,544,267 and Marcus 4,553,387. However, for a variety of reasons, systems such as these have not gained widespread acceptance.

Due to the compound curved nature of the fingerprint on a finger, it is difficult to optically obtain an image corresponding to a rolled fingerprint. The Schiller U.S. Pat. No. 4,544,267 discloses an apparatus in which a finger pressed against a platen provides a fingerprint object which is scanned by an interrogating beam of collimated light that is linearly displaced across the platen thereby maintaining a constant angle between the interrogating light beam and the plane of the object being scanned. The Marcus U.S. Pat. No. 4,553,837 discloses finger processing apparatus which includes a cylindrical-segment platen which supports a finger. Optical scanning equipment scans the circumference of the platen in such a manner that the angle of incidence of a light beam on the fingerprint object remains constant. The Becker U.S. Pat. No. 3,482,498 discloses several embodiments of an optical apparatus for producing a rolled fingerprint image, both of which utilize a prism having a totally reflecting surface. The embodiment shown in FIG. 1a utilizes a plurality of prisms and light sources, and produces only an approximation of the ball and side ridges. The embodiment shown in FIGS. 2 and 3 utilize a mechanical system actuated by a rolling finger to move and position a light source.

While the fingerprinting systems disclosed in the Schiller and Marcus patents, and the second embodiment disclosed in the Becker patent, may be capable of optically providing a rolled fingerprint image, these systems are less than wholly desirable. Perhaps most important, it is not possible to review the image being captured in real-time to determine whether or not critical information required for classification is being captured. Furthermore, the mechanical aspects of these systems, are relatively complicated. As a result, maintaining focus during the time required to obtain the entire rolled fingerprint image can be difficult. Although the fingerprint image produced by the first embodiment of the invention disclosed in the Becker patent provides an image in real-time, this image only approximates the rolled fingerprint image.

Prisms such as those disclosed in the McMahon U.S. Pat. No. 3,975,711 and the White U.S. Pat. No. 3,200,701 utilize the optical principle of total internal reflection to produce a fingerprint image. As such, the "plane" of the fingerprint must be imaged at an observation angle which is not perpendicular to the plane. Vertical scale errors, or distortions of distances on the fingerprint image from their true distances along a Y-axis which is generally parallel to a longitudinal axis of the finger, are therefore inherent. When the surface of the prism on which the finger is inserted is grooved as illustrated in the McMahon patent, horizontal scale errors which are distance distortions on the fingerprint image from true distances along a X-axis generally perpendicular to the longitudinal axis of the finger on the fingerprint, are also inherent. Furthermore, curvature errors are also produced. As a result of the vertical and horizontal scale errors, and the curvature errors inherent in the use of a grooved total internal reflection prism such as that shown in McMahon, the fingerprint image provided thereby is severely distorted from a true rolled fingerprint of the same finger.

Prisms which have grooved finger receiving surfaces such as those disclosed in the McMahon patent will not provide optimum surface contact between the surface of a finger and therefore its fingerprint, and the prism. Portions of the fingerprint which it may be desired to obtain will therefore be lost. Illumination of the fingerprint through prisms such as that shown in the McMahon patent is often unequal, resulting in an image which has varying intensities throughout its area. Furthermore the contrast between ridges and valleys in the fingerprint image produced by these prisms is generally relatively low.

Many police departments including the FBI require both plain or slap fingerprint images and individual rolled fingerprint images as part of their standard fingerprinting process. Prior art optical fingerprinting systems, however, are incapable of optically generating both individual rolled fingerprints and slap fingerprint images.

It is evident that there is a continuing need for improved optical fingerprinting systems. A system having the capability of capturing both slap and rolled fingerprint images would be especially desirable. An operator should be able to easily interface with the system, and observe in real-time the quality of the fingerprint image before it is captured. A system which can capture fingerprints from fingers of varying sizes would also be useful.

It is also evident that there is room for improvement in the prisms utilized by optical fingerprinting systems. Grooves in these prisms should be contoured in a manner which permits optimum contact between the fingerprint and grooved surface. A prism which can capture slap fingerprint images is also needed. A prism which reduces horizontal and vertical scale errors, as well as curvature errors, would also be welcomed. Furthermore, a prism which produces a high contrast fingerprint image is also needed. Other techniques which can correct for vertical and horizontal scale errors, and curvature errors so as to produce an enhanced fingerprint image would also be desirable properties of an optical fingerprinting system.

SUMMARY OF THE INVENTION

The present invention is a method of operating programmable computing means to enhance fingerprint images. Using a noise average method, input pixel values of an array of input pixel values characteristic of the fingerprint image are processed to produce a noise averaged array of pixel values characteristic of a noise averaged image. An input array of pixel value characteristic of a fingerprint image is received. Noise averaging subarrays of input pixel values are selected. Each subarray includes an input pixel value to be noise averaged, and a plurality of input pixel values adjacent the pixel value to be noise averaged. Noise averaged pixel values are generated as a function of a weighted average of the input pixel values in the noise averaging subarrays. The noise averaged pixel values are then stored as an array of noise averaged pixel values characteristic of the image.

Using an illumination equalizing method, input pixel values of an array of input pixel values characteristic of a fingerprint image are processed to produce an illumination equalized array of pixel values characteristic of an illumination equalized image. An array of input pixel values characteristic of a fingerprint image is received. Equalizing subarrays of input pixel values are selected. Each subarray includes an input pixel value to be illumination equalized. Subarray average values are generated as a function of the pixel values within the equalizing subarrays. The subarray average values are subtracted from the corresponding pixel values being equalized to generate pixel difference values. A predetermined constant is added to the pixel difference values to generate intermediate illumination equalized pixel values. If intermediate illumination equalized pixel values are less than a predetermined minimum pixel value, the corresponding illumination equalized pixel values are set equal to the minimum pixel value. If intermediate illumination pixel values are greater than or equal to the minimum pixel value, and less than or equal to a predetermined maximum pixel value, the corresponding illumination equalized pixel values are set equal to the corresponding intermediate illumination equalized pixel values. If the intermediate illumination equalized pixel values are greater than the maximum pixel value, the corresponding illumination equalized pixel values are set equal to the maximum pixel value.

BRIEF DESCRIPTION OF THE DRAWINGS

FIG. 6 is a perspective view of an individual finger prism shown in FIG. 2.

FIG. 7 is a sectional view of the finger prism shown in FIG. 6.

FIG. 8 is a rear view of the finger prism shown in FIG. 6.

FIG. 9 is a side view of the finger prism shown in FIG. 6.

FIG. 10 is a top view of the finger prism shown in FIG. 6.

FIG. 11 is a bottom view of the finger prism shown in FIG. 6.

FIG. 12 is a graphic representation of the optical properties of the finger prism shown in FIG. 6, when a finger is not positioned within its groove.

FIG. 13 is a graphic representation of the optical properties of the prism shown in FIG. 6, when a finger is positioned within its groove.

FIG. 14 is a detailed view of a portion of the prism and finger shown in FIG. 13, graphically illustrating the optical properties of the prism in conjunction with a finger positioned thereon.

FIG. 15 is a graphic representation of a finger illustrating various characteristics of a fingerprint thereon.

FIG. 16 is a perspective view of an alternative embodiment of the slap print prism shown in FIG. 2.

FIG. 17 is a side view of the slap print prism shown in FIG. 16.

FIG. 20 is a block diagram representation of the processor subsystem of the optics/processor unit shown in FIG. 1, and illustrating its interconnection to other electrical elements of the fingerprinting system.

FIG. 21 is a graphic representation of an image array of image pixel values generated by the frame digitizer shown in FIG. 20.

FIG. 23 is a graphic representation of an illumination equalized array of illumination equalized pixel values generated by the processor subsystem shown in FIG. 20.

FIG. 27 is a detailed graphic representation of an illumination equalized array such as that shown in FIG. 26, illustrating the regular and offset subarrays utilized by the processor subsystem shown in FIG. 20 to produce the directional filtered array.

FIG. 29 is a graphic representation of an unhaired array of unhaired pixel values produced by the processor subsystem shown in FIG. 20.

FIG. 31 is a graphic representation of a curvature corrected array of curvature corrected pixel values generated by the processor subsystem shown in FIG. 20.

FIG. 38 is a graphic representation of a table of vertical scale correction data generated by the processor subsystem from the curvature corrected array shown in FIG. 37, and used to generate a vertically scaled array.

FIG. 39 is a graphic representation of a horizontally scaled array of horizontally scaled pixel values generated by the processor subsystem shown in FIG. 20.

FIG. 40 is a graphic representation of a table of horizontal scale correction data generated by processor subsystem from the image of the pattern of indicia shown in FIG. 32 and used to produce the vertically scaled array shown in FIG. 39.

FIG. 41 is a graphic representation of a vertically scaled array representative of the image of the pattern of indicia shown in FIG. 32.

FIG. 42 is an illustration of a Main Display menu generated and displayed by the data terminal shown in FIG. 1.

FIG. 43 is a detailed view of the display on the optics/processor unit shown in FIG. 1.

FIG. 45 is an illustration of a Demographic/Department Information menu generated and displayed by the data terminal shown in FIG. 1.

FIG. 46 is an illustration of a Processing Choices menu generated and displayed by the data terminal shown in FIG. 1.

FIG. 47 is a graphic representation of a booking or applicant card onto which fingerprint images, department information and demographic information can be printed by the printer shown in FIG. 1.

DETAILED DESCRIPTION OF THE PREFERRED EMBODIMENTS

Overall System and Optics Subsystem Description

Figure 1:
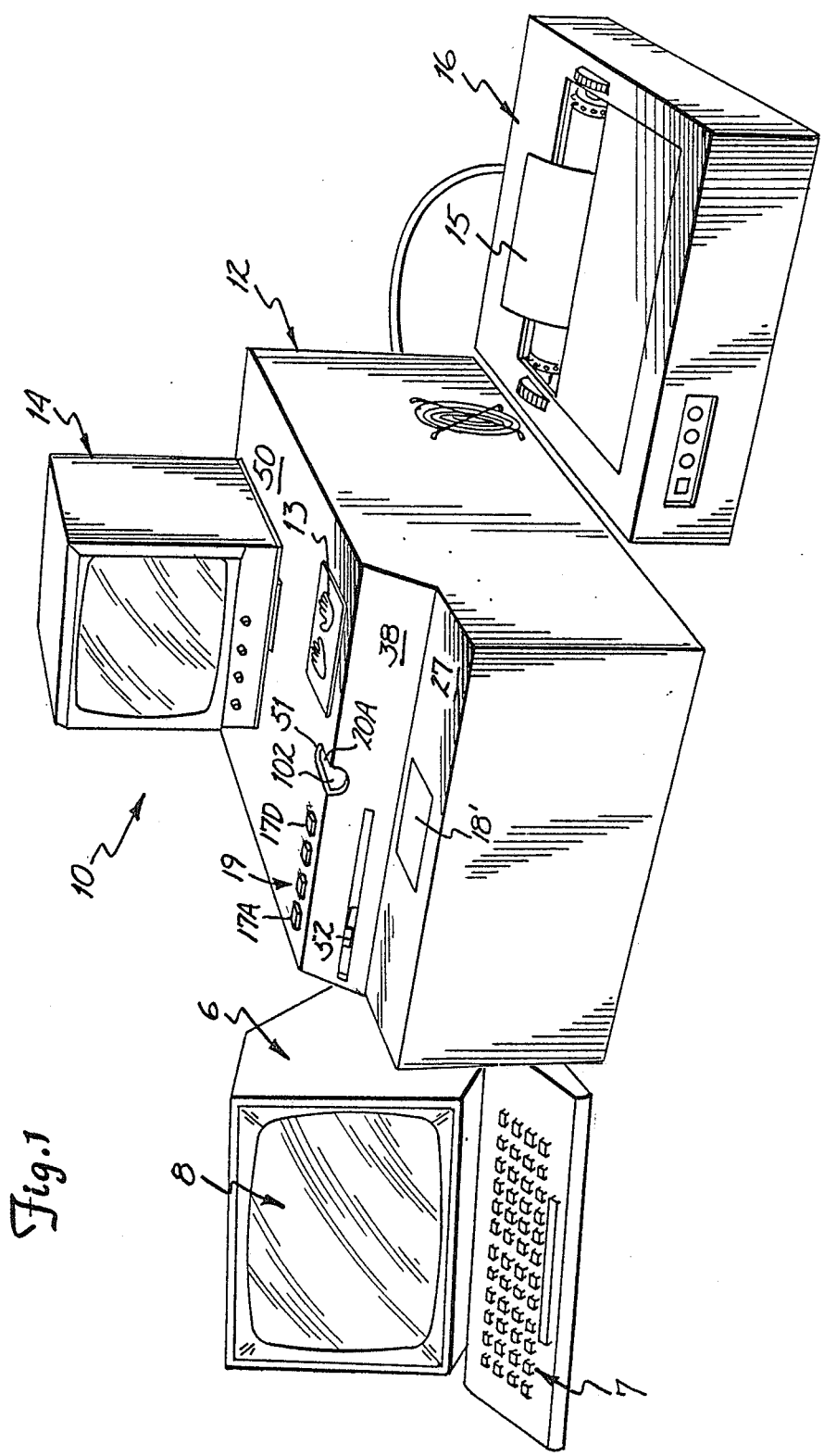
FIG. 1 illustrates elements of an optical fingerprinting system in accordance with the present invention.

An optical fingerprinting system 10 in accordance with the present invention is illustrated generally in FIG. 1. As shown, fingerprinting system 10 includes an optics/processor unit 12, video monitor 14, printer 16, and data terminal 6, which includes a keyboard 7 and monitor 8. Data terminal 6, monitor 14 and printer 16 are interfaced to optics/processor unit 12. Fingerprinting system 10 is capable of providing printed records of both plain or "slap" prints which are simultaneous impressions of the fingerprints of all fingers of a hand other than the thumb, and individual fingerprints.

To take a slap print, the person to be fingerprinted will position the fingertips of their index, middle, ring and little fingers on slap print prism 18'. Optics/processor unit 12 images the slap print and provides a real-time visual display thereof on monitor 14. When an operator observes a satisfactory slap print image on monitor 14, a key 17A–17D on key pad 19 is actuated causing optics/processor unit 12 to "freeze" the image by storing digital data representative thereof. This image is then enhanced when the digital data is processed by optics/processor unit 12 in accordance with image enhancement software. Data representative of the enhanced image is then stored. If it is desired to fingerprint an individual finger, the person to be fingerprinted will position their finger within groove 102 of an individual finger prism such as 20A. Optics/processor unit 12 will image the fingerprint, and provide a display thereof on monitor 14. This image can then be "frozen", and data representative thereof processed by optics/processor unit 12 and stored.

Demographic data characteristic of the person being fingerprinted and department data (or other relevant information) utilized by the organization doing the fingerprinting can be entered into system 10 by the operator through keyboard 7. This data, along with the stored fingerprint images, can then be printed at proper locations on a document such as a standard booking or applicant card 15 by printer 16. These procedures are all facilitated by system generated menus and prompts which are displayed on monitor 8 of data terminal 6, as well as by display 13 and illumination of buttons 17A–17D of key pad 19.

Figure 2:
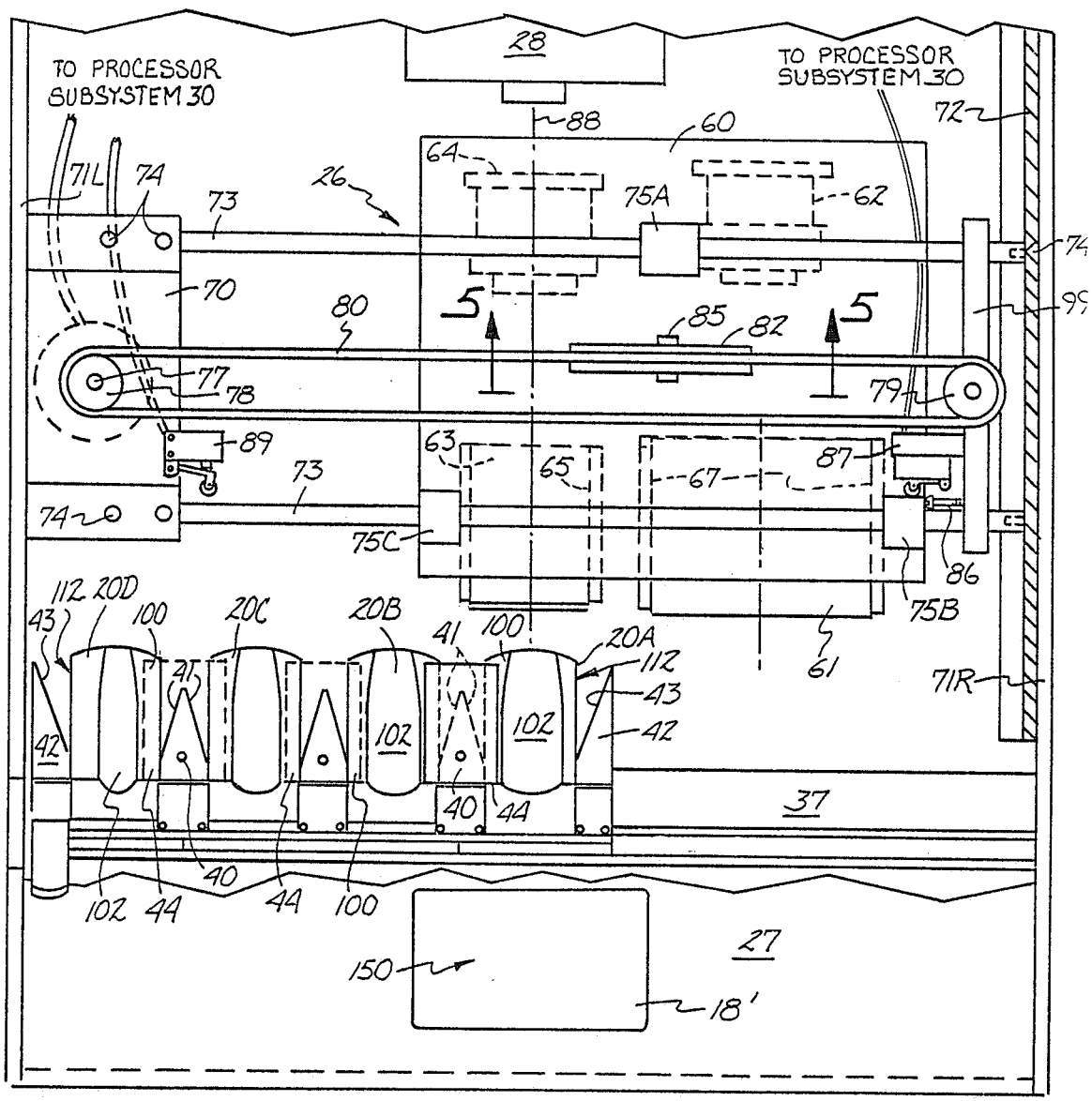
FIG. 2 is a view looking into the top of the optics/processor unit shown in FIG. 1.
Figure 3A:
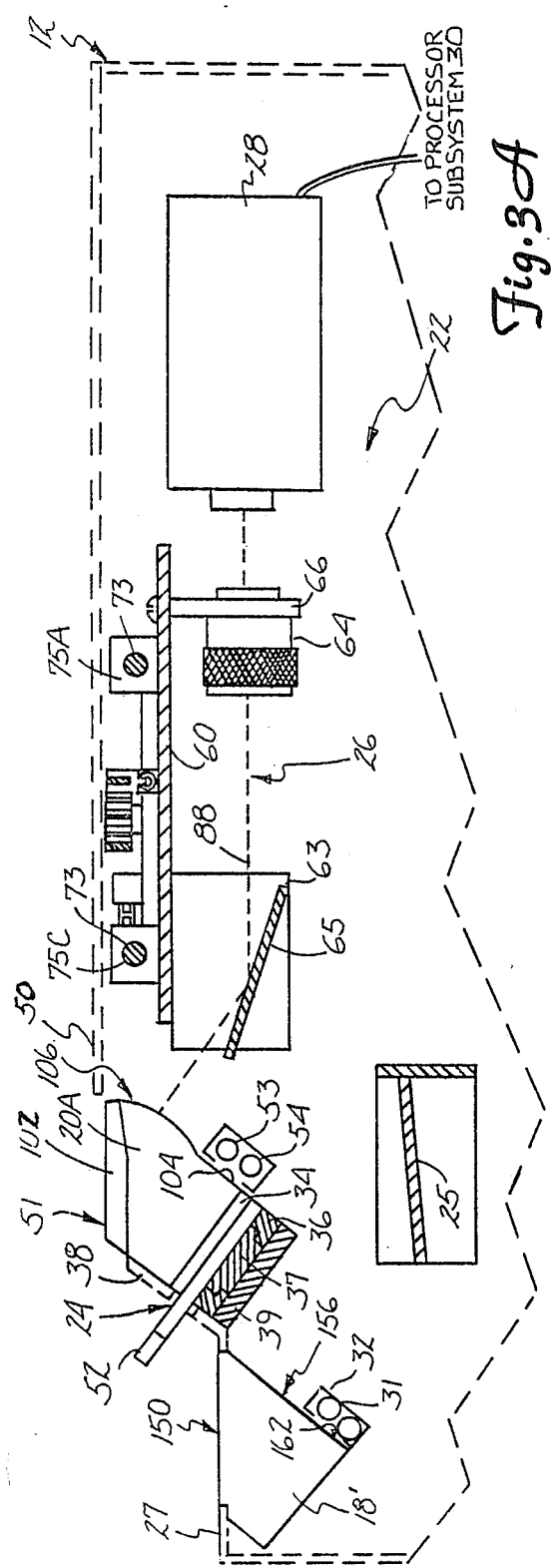
FIG. 3A is a side view of the optics subsystem shown in FIG. 2, illustrating the optical propagation of fingerprint images from the finger prism to the camera when the slap/image selection optics is positioned at its finger image position.
Figure 3B:
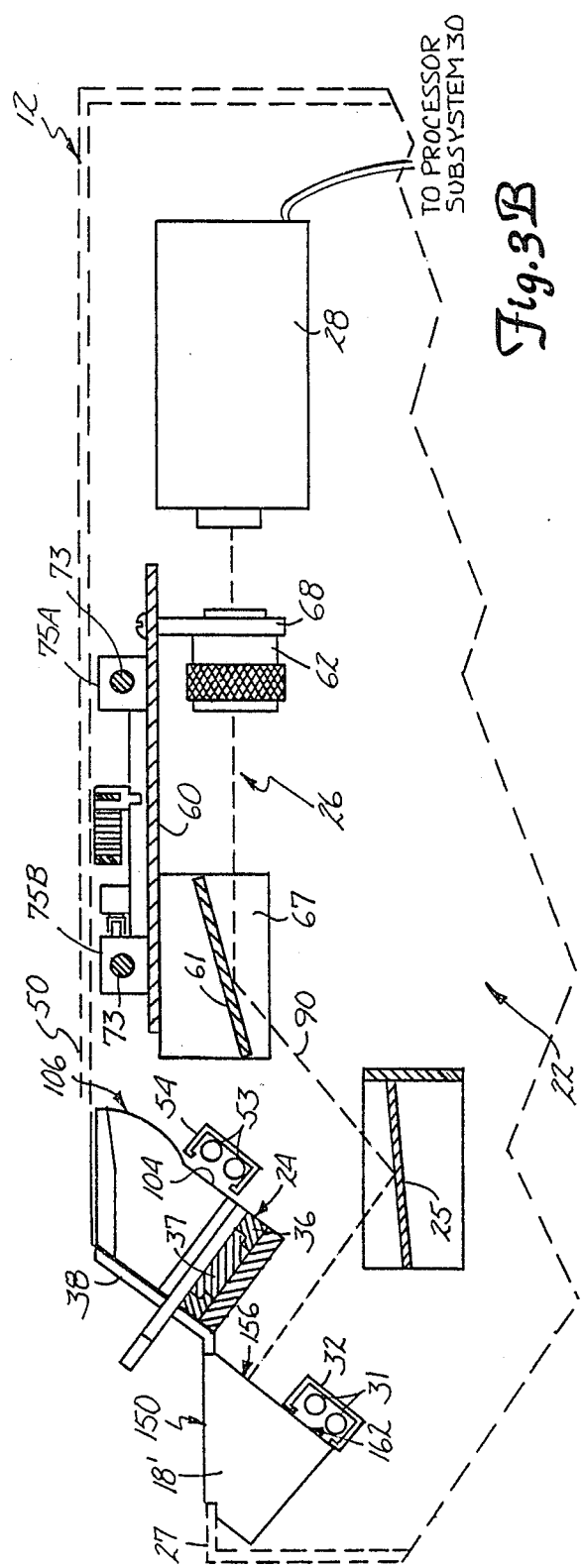
FIG. 3B is a side view of the optics subsystem shown in FIG. 2 illustrating the optical propogation of fingerprint images from the slap prism to the camera when the slap/image selection optics is positioned at its slap image position.

An optics subsystem 22 within optics/processor unit 12 is illustrated in greater detail in FIGS. 2, 3A and 3B. Optics subsystem 22 includes slap print prism 18', finger prism trolley 24, first slap image mirror 25, slap/finger image selection optics 26, and a sensor such as video camera 28. Slap print prism 18' is mounted in such a manner that its finger-receiving surface 150 is generally level and coplanar with a stepped top panel 32 of unit 12. First slap image mirror 25 is mounted with respect to slap print prism 18' so as to receive slap fingerprint images projected from image projection surface 156 of the prism, and to reflect these images to slap/finger image selection optics 26. Slap print prism 18' is illuminated by means of a light source such as lamp 31 which is positioned adjacent to a light-receiving surface 162 of the prism. In the embodiment shown, lamp 31 is a sideways oriented U-shaped fluorescent bulb having two legs which are shown in cross section. The two legs of lamp 31 extend across light-receiving surface 162 of prism 18', and are surrounded on a side opposite prism 18' by reflector 32.

Figure 4:
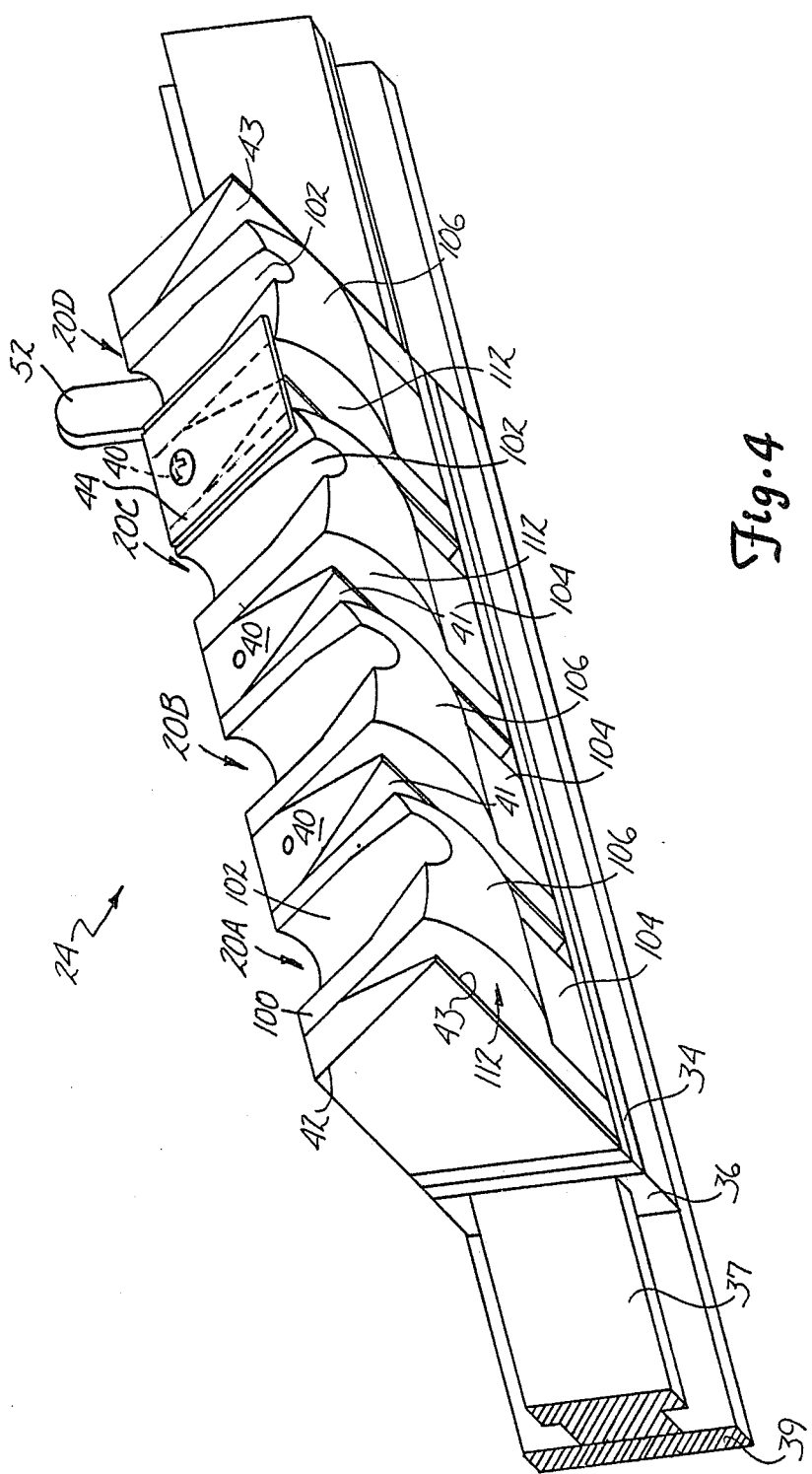
FIG. 4 is a detailed perspective view of the lens trolley shown in FIG. 2.
Figure 18:
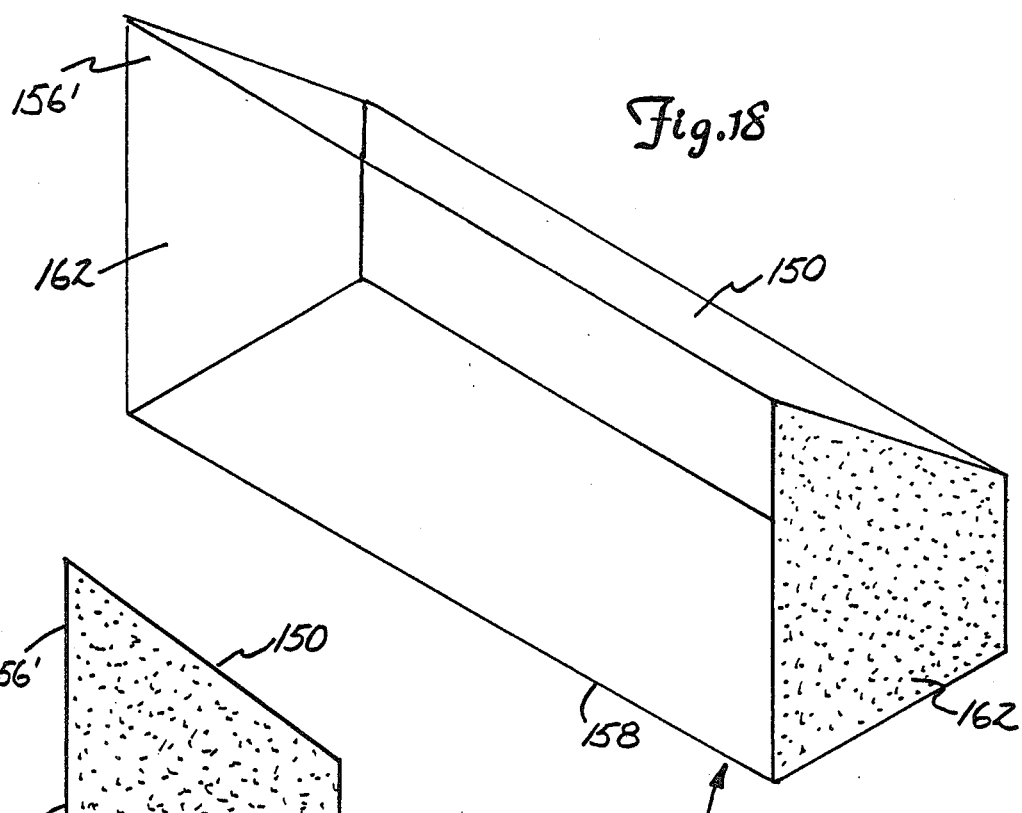
FIG. 18 is a perspective view of the slap print prism shown in FIG. 2.
Figure 19:
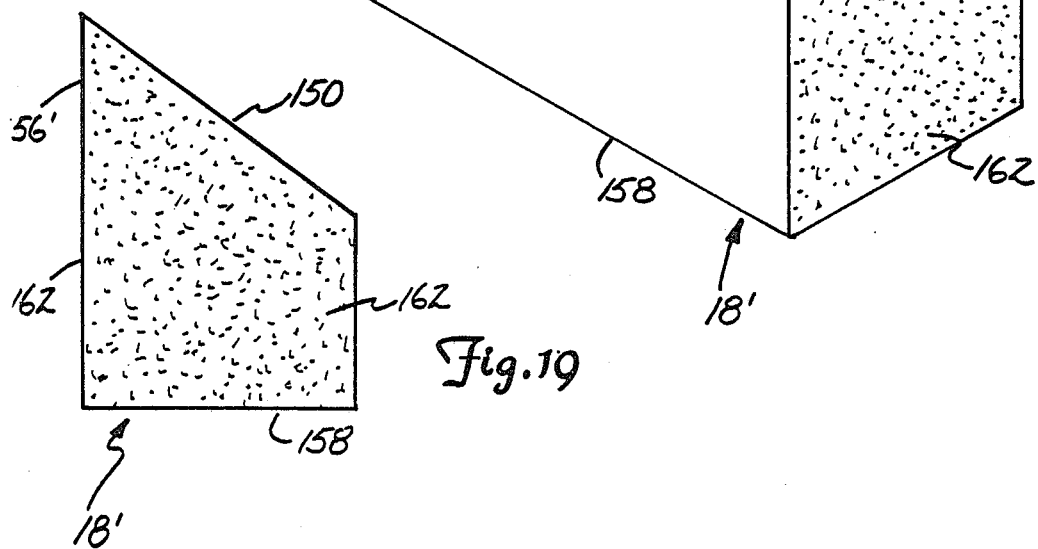
FIG. 19 is a side view of the slap print prism shown in FIG. 18.

Finger prism trolley 24, which is illustrated in greater detail in FIG. 4, includes a base 34 to which a plurality of individual finger prisms 20A-20D are mounted by screws or other suitable fasteners (not shown). Base 34 includes a track-follower section 36 which is slidably received upon a guide track 37. Guide track 37, in turn, is mounted with respect to a sloping front panel 38 of unit 12 by means of a mounting bracket 39. As shown in FIGS. 2 and 4, each finger prism 20A-20D has an upper surface 100 which includes a finger-receiving groove 102. Prisms 20A-20D are spaced from one another by triangular shaped mirror blocks 40 which have reflective or mirror side surfaces 41 which angle away from side surfaces 112 of prisms 20A-20D and intersect at a point toward slap/finger image selection optics 26. End mirror blocks 42 are positioned adjacent side surfaces 112 of prisms 20A and 20D which are opposite mirror blocks 40. End mirror blocks 42 also have a reflective side surface 43 which angles away from side surfaces 112 in a direction toward slap/finger selection optics 26. Mirror blocks 40 have their top surface covered by cover plates 44 (some of which are shown in phantom in FIG. 2) which extend between adjacent prisms 20A-20D.

Finger prism trolley 24 is mounted with respect to unit 12 at an angle in such a manner that finger-receiving grooves 102 of prisms 20A-20D are generally parallel with top panel 50 of the unit. As perhaps best shown in FIGS. 1, 3A and 3B, a finger-receiving cutout or aperture 51 extends through top panel 50 and sloping side panel 38 at a position adjacent trolley 24 to expose groove 102 of one of prisms 20A-20D. By means of trolley handle 52 which extends through panel 38, an operator can slide trolley 24 along guide track 37 in such a manner as to position groove 102 of a desired finger prism 20A-20D adjacent aperture 51. A lamp 53, which can be identical to lamp 31 previously described, is mounted with respect to unit 12 below aperture 51 and adjacent a light-receiving surface 104 of whichever prism 20A-20D has been positioned adjacent aperture 51. Light from lamp 53 will directly enter light-receiving surface 104, and be reflected by surfaces 41 and 43 of mirror blocks 40 and 42, respectively, into side walls 112 of the selected finger prism 20A-20D. A fingerprint image of a finger positione- within groove 102 of the selected prism 20A-20D will thereby be propagated from image propagation surface 106 toward slap/finger image selection optics 26.

Slap/finger image selection optics 26 includes a mounting plate 60 which has a second slap image mirror 61 and a slap image focusing lens assembly 62, as well as a finger image mirror 63 and finger image focusing lens assembly 64 mounted to a lower side thereof. Finger image mirror 63 is mounted to mounting plate 60 by means of mounting brackets 65, and is oriented at an angle so as to receive fingerprint images propagated from one of finger prisms 20A-20D and to reflect the fingerprint image to a lens (not separately visible) within finger image focus lens assembly 64. Lens assembly 64 is mounted to mounting plate 60 by means of mounting bracket 66. Second slap image mirror 61 is mounted to mounting plate 60 by mounting brackets 67 at a position adjacent finger image mirror 63. Mirror 61 is oriented at such an angle as to receive slap print images from first slap image mirror 25, and to reflect these images to a lens (not separately visible) within lens assembly 62. Lens assembly 62 is mounted to mounting plate 60 by means of mounting bracket 68. The lenses within lens assemblies 62 and 64 can be adjustably positioned along their optical axis to facilitate optical focusing adjustments of subsystem 22.

As shown in FIG. 2, a motor mounting bracket 70 is mounted to a left side panel 71L of unit 12, while a support bracket 72 is mounted to right side panel 71R. Mounted to and extending bbetween brackets 70 and 72 is a pair of guide rods 73. Guide rods 73 are mounted to brackets 70 and 72 by means of fasteners 74 in the embodiment shown. Mounting plate 60 is slidably suspended from guide rods 73 by means of slide bushings 75A-75C.

A motor 76 which is interfaced to processor subsystem 30 is mounted to a lower face (not. visible) of mounting bracket 70, and has a drive shaft 77 which extends through the bracket. A drive wheel 78 is mounted to shaft 77. An idler wheel 79 is rotatably mounted to an idler bracket 99. Idler bracket 99 is mounted acrossguide rods 73.

Looped between drive wheel 78 and idler wheel 79 is a drive belt 80.

Figure 5:
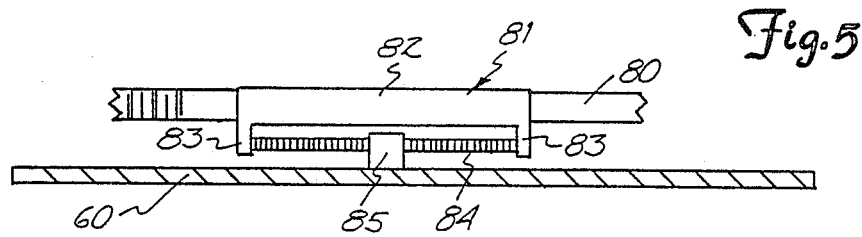
FIG. 5 is a detailed view of the fastening assembly shown in FIG. 2.

A flexible fastening assembly 81 for flexibly fastening belt 80 to mounting plate 60 is illustrated in FIG. 5. Fastening assembly 81 includes a clamp 82 which has a slot (FIG. 2) into which drive belt 80 is fixedly clamped. Clamp 82 also has a pair of downward extending arms 83 on its opposite sides. Ends of a flexible member such as stretched spring 84 are fastened to arms 83. A central portion of spring 84 is fastened to mounting plate 60 by means of clamp or bracket 85.

Motor 76 is interfaced to a processor subsystem 30 of optics/processor unit 12. In response to finger prism select signals from processor subsystem 30, motor 76 will rotate in a clockwise direction as viewed in FIG. 2, thereby driving mounting plate 60 (slap/finger image selection optics 26) along guide rods 73 to a rightmost or finger prism select position illustrated in FIGS. 2 and 3A. Mounting plate 60 is driven in this manner until slide bushing 75B is positioned against adjustable stop 86 and actuates microswitch 87. Microswitch 87 is interfaced to processor subsystem 30, and provides signals representative of the positioning of mounting plate 60 to the finger prism select positon.

With slap/finger image selection optics 26 in the finger prism select position, video camera 28, finger prism focus lens assembly 64, and finger image mirror 63 are all aligned with the finger prism 20A-20D with has been positioned adjacent aperture 51. Visual images of fingerprints of fingers positioned with groove 102 will thereby be propagated from image propagation surface 106 of the selected prism 20A-20D along finger image optical path 88, reflecte by mirror 63, focused by the lens within assembly 64, and imaged by camera 28.

In response to slap print prism select signals from processor subsystem 30, motor 76 will rotate in a counterclockwise direction, thereby pulling mounting plate 60 and slap/finger image selection optics 26 to a slap print select or leftmost position (not shown) when viewed from FIG. 2. Slide bushing 75C will then actuate microswitch 89, which in turn provides slap print positioning select signals to processor subsystem 30. Processor subsystem 30 then stops rotation of motor 76.

Figure 44:
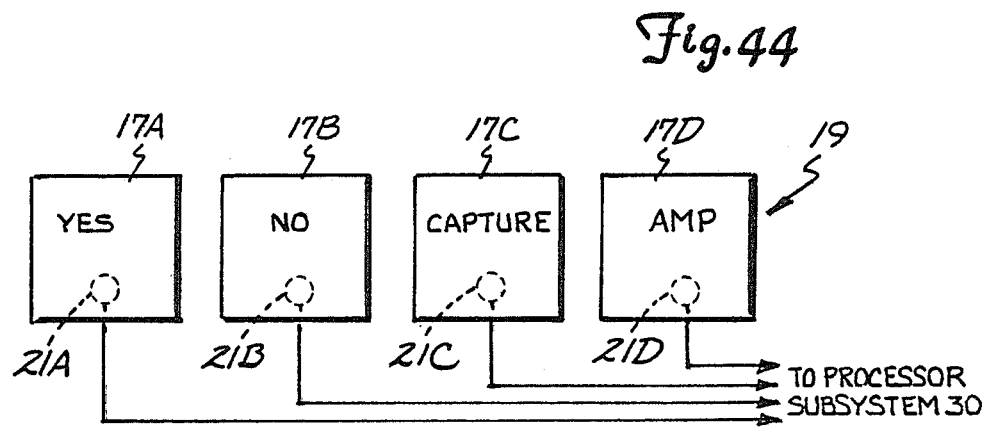
FIG. 44 is a detailed view of the key pad on the optics/processor unit shown in FIG. 1.

As illustrated in FIG. 3B, when selection optics 26 are properly positioned in the slap print select position, second slap image mirror 61 and slap print focusing lens assembly 62 will be aligned about a slap print optical path 90 between slap print prism 18', first slap image mirror 25, and camera 28. Slap print images of fingers positioned on slap print prism 18' will thereby be propagated from image propagation surface 156 of the prism along slap print optical path 90, reflected by mirrors 25 and 61, focused by the lens within assembly 62, and imaged by camera 28. Video signals representative of fingerprint images imaged by camera 28 are provided to processor subsystem 30. Key pad 19 is illustrated in FIGS. 1, 20, and 44. As perhaps best illustrated in FIG. 44, key pad 19 is formed by a YES key 17A, a NO key 17B, a CAPTURE key 17C, and an amputee or AMP Key 17D. Keys 17A-17D are preferably fabricated of a translucent material such as plastic, and have a light source such as LEDs 21A-21D, respectively, positioned thereunder. LEDs 21A-21D are each individually interfaced to processor subsystem 30 as shown, and can be individually lit or illuminated by the processor subsystem.

Display 13 is illustrated in greater detail in FIG. 43. As shown, display 13 includes a left hand representation or indicia 312, and a right hand indicia 314. Each finger of indicia 312 and 314 have a light such as LEDs 316A≅316E and 318A-318E associated therewith. In the embodiment illustrated in FIG. 43, LEDs 316A-316E are positioned in the thumb, index, middle, ring, and little fingers of left hand indicia 312. Leds 318A-318E are positioned in the thumb, index, middle, ring and little fingers of right hand indicia 314. Leds 316A-316E and 318A-318E are each interfaced (FIG. 20) individually to processor subsystem 30 so as to be capable of individual illumination thereby.

Individual Finger Prisms

Individual finger prism 20A, which is representative of individual finger prisms 20A-20D, is perhaps best described with reference to FIGS. 6-11. Prism 20A is an optical device fabricated of light-propagating material such as plastic which is characterized by an index of refraction. In one embodiment, prisms 20A-20D are machined from acrylic polymer, although they can also be molded from this or other materials.

As shown, prism 20A has a first or sloping upper surface 100 which has a finger-receiving groove 102 therein, and a front face which includes both a second or light-receiving surface 104 and a third or image propagation surface 106. Prism 20A also includes a fourth or bottom surface 108, a fifth or back surface 110, and two side faces or surfaces 112.

Prism 20A has a width of dimension D1, and an overall depth of dimension D2. Back surface 110 is perpendicular to bottom surface 108 and extends to a height of dimension D3 from the bottom surface. Upper surface 100 intersects back surface 110 at an angle A1 with respect to bottom surface 108. Light-receiving surface 104 extends perpendicularly from bottom surface 108 to a height of dimension D4. The magnitude of angle A1 will depend upon the index of refraction of the material from which prism 20A is manufactured. In one preferred embodiment in which prism 20A is manufactured of acrylic polymer, angle A1 is 35°. In this same embodiment, dimensions D1-D4 are 1.58 inches, 2.35 inches, 1.62 inches, and 0.95 inches, respectively.

As shown in FIGS. 6, 7, 8, and 10, groove 102 is elongated and contoured to receive a finger. Groove 102 includes both a fingerbody portion 113 and a fingertip portion 114. Fingerbody portion 113 and fingertip portion 114 of groove 102 both include a bottom wall 116 and side walls 118. As best shown in FIG. 7, the deepest part of bottom wall 116 of fingerbody portion 113 is at a constant depth of dimension D8 with respect to upper surface 100. The deepest part of bottom wall 116 of fingertip portion 114 slopes from its intersection with fingerbody portion 113 toward upper surface 100 at an angle A5 (45° in one embodiment) with respect to bottom surface 108. In the embodiment shown in FIG. 7, bottom wall 116 curves between portions 113 and 114 at a radius of curvature defined by dimension D6. In one preferred embodiment, dimension D6 is a 2.00 inch radius of curvature. This radius of curvature (dimension D6) is centered at a point displaced from the intersection of upper surface 100 and back surface 110 by length of dimension D7. Following the embodiment described above, dimension D8 is 0.50 inches while dimension D7 is 0.72 inches.

As perhaps best shown in FIG. 5, bottom wall 116 of groove 102 is semicircular having a radius of curvature characterized by dimension D8. This radius of curvature (dimension D8) can be constant throughout the length of groove 102. Side walls 118 are preferably planar, and form an angle A2 with respect to side surfaces 112 which are perpendicular to both upper surface 100 and bottom surface 108 of prism 20A. In one preferred embodiment, angle A2 is $22\frac{1}{2}°$.

The above-described characteristics of groove 102 have been found to permit the highest or optimum degree of contact between a finger (not shown in FIGS. 6-11) and the various surfaces of the groove. This feature is especially important for fingertip portion 114 of groove 102 so that an image of the largest possible area of the fingerprint on the tip of a finger is propagated from prism 20A. Dimensions D6, D7 and D8, as well as angle A2, will of course vary depending upon the size of the finger to be received by groove 102. As shown in FIGS. 2 and 4, the size of grooves 102 of each prism 20A-20D on trolley 24 is different so that a prism having a properly sized groove 102 can be selected as needed for the particular finger of a particular person being fingerprinted. In general, the larger the finger being fingerprinted, the larger the groove 102 of the selected prism 20A-20D. Dimension D1 of prism 20A will of course also have to increase for prisms 20A-20D with larger grooves 102 (dimension D8).

In the embodiment of prism 20A shown in FIGS. 6-11, image propagation surface 106 and light-receiving surface 104 are both curved so as to function as lenses. Light-receiving surface 104 forms a cylindrical lens and has a radius of curvature defined by dimension D9. This radius of curvature (dimension D9) is centered about a point of dimension $D\frac{1}{2}$ from side surfaces 112, and spaced from back surface 110 by a distance of dimension D10. In the embodiment of prism 20A described above, dimension D9 is 1.88 inches while dimension D10 is 0.25 inches. The radius of curvature or dimension D9 of lensed light-receiving surface 104 is therefore perpendicular to back surface 110 and parallel to bottom surface 108. Alternatively, light-receiving surface 104 can be characterized as being cylindrically curved about an imaginary vertical axis 105 which is perpendicular to bottom surface 108 and parallel to back surface 110.

Image propagation surface 106 is formed as a spherical convex lens in the embodiment shown, and has a radius of curvature of dimension D11 in both horizontal (X) and vertical (Y) directions. In the embodiment of prism 20A illustrated in FIGS. 6-11, radius of curvature or dimension D11 is centered at a distance of dimension D3 from bottom surface 108, halfway about back surface 110 (d½) and a distance of dimension D10 from back surface 110. In the embodiment described above, dimension D11 is 2.00 inches.

To increase the contrast of fingerprint images provided by or propagated from prism 20A, various surfaces are coated by an opaque substance to inhibit transmission of light. In the embodiment shown, bottom surface 108, back surface 110, and planar portions of upper surface 100 other than those of groove 102 are coated with an opaque substance. In addition, portions of side surfaces 112 adjacent back surface 110 (those portions at which mirror blocks 40 or 42 meet prisms 20A-20D as shown in FIG. 2) are also coated. Black paint can be applied to the above-identified surfaces to prevent transmission of light through absorption.

The optical properties of prism 20A (which are similar to those of prisms 20A-20D) are described with reference to FIGS. 12-14. Prism 20A is designed to utilize the optical principal of frustration of total internal reflection. Due to the relative indexes of refraction of air and the material of which the prism 20A is constructed, and the angles of upper surface 100 and surfaces 116 and 118 of groove 102 with respect to image propagation surface 106 and light-receiving surface 104, all light incident upon groove 102 when a finger is not present thereon is refracted downward toward bottom surface 108 or sideways toward side surfaces 112 upon its entry into prism 20A as illustrated in FIG. 12. Most importantly, virtually none of the light entering groove 102 will be directed out of image propagation surface 106. Virtually all of the light which strikes bottom surface 108 or the opaque portions of side surfaces 112 is absorbed due to the opaque coating, and not re-reflected.

Light from lamp 53 will enter prism 20A through light receiving surface 104, image propagation surface 106, and portions of side faces 112 which are not coated with opaque material. Light so entering which impinges upon groove 102 will either pass through the groove and exit prism 20A, or be internally reflected to one of the opaque surfaces such as bottom surface 108 or back surface 110, and absorbed. Virtually none of the light incident upon prism 20A from lamp 53 will exit image propagation surface 106. As a result, an observer looking into image propagation surface 106 will see only "black" when no finger is positioned on surfaces 116 or 118 of groove 102.

Characteristics of a finger 132 are described with reference to FIG. 15 for use throughout subsequent portions of this specification. As shown, the tip of finger 132 has a finger pad or base area which has a fingerprint 134 thereon. Fingerprint 134 is a pattern formed by ridges 136 (light areas) and valleys 138 (dark areas) of the finger pad.

Referring back to FIGS. 13 and 14, when finger 132 is positioned within groove 102, the total internal reflection properties of prism 20A are frustrated or destroyed at points at which ridges 136 of the fingerpad contact surfaces 116 and 118 of groove 102. As shown in detail in FIG. 14, portions of prism 20A at which ridges 136 contact a surface such as 116 of groove 102 are characterized by a skin-prism material boundary, while those portions at which valleys 138 are adjacent surface 116 are characterized by an air-prism material boundary as if a finger were never positioned in groove 102. At the areas at which ridges 136 contact surfaces 116 or 118 of groove 102, light which passes through the groove and into the skin will be partially absorbed by the skin and partially re-reflected back into prism 20A. Due to the different index of refraction of skin from that of air, this light which re-enters prism 20A at a skin-prism material boundary is refracted toward image propagation surface 106 and propagated therethrough. However, light which re-enters groove 102 at areas at which valleys 138 are adjacent surfaces 116 and 118 behaves as previously described due to the air-prism material interface between groove 102 and finger 132. When this light re-enters prism 20A, it is refracted downward and absorbed as previously described. These properties are illustrated graphically in FIG. 13. As a result, a visual image of fingerprint 134 (fingerprint image) is propagated through image propagation surface 106. This fingerprint image has "light" areas corresponding to ridges 136 of the fingerprint 134, and "dark" areas corresponding to valleys 138.

The fingerprint image of finger 132 propagated from prism 20A will be distorted from that of a planar "rolled" fingerprint image of the same finger. These distortions are broadly characterized as curvature errors, and size or scale errors, and are caused by different characteristics of finger 132, prism 20A, and their interaction.

As illustrated in FIG. 15, fingers such as 132 can be characterized by an imaginary longitudinal axis 139 which extends along the finger. The fingerpad on which fingerprint 134 is located is a compound curved surface in that it has base curvature about both an X-base curve axis 140 (generally referred to as an X-axis) and a Y-base curve axis 141 (generally referred to as a Y-axis). X-base curve axis 140 is oriented in a circumferential direction about longitudinal axis 139, and is formed by a locus of points which are perpendicular to a given point about the longitudinal axis.

Portions of fingerprint 134 about an X-base curve axis such as 140 would be colinear in a rolled fingerprint of fingerprint 134. However, the fingerprint image of fingerprint 134 propagated from image propagation surface 106 of prism 20A is planar, with an imaginary axis 142 which is perpendicular to the image plane (i.e., a plane "parallel" to image propagation surface 106) forming an observation angle OA with respect to longitudinal axis 139 of finger 132. Observation angle OA will be equal to angle A1 (FIG. 7) for those portions of the fingerprint image corresponding to portions of finger 132 which are positioned on fingerbody portion 113 of groove 102. Observation angle OA increases in accordance with the upwardly curved bottom wall 116 for those portions of the fingerprint image corresponding to portions of finger 132 which are positioned on fingertip portion 114 of groove 102. As a result of finger 132 being imaged at an observation angle OA which is between zero and ninety degrees and the curved nature of fingerprint 134 about X-base curve axis 140, portions of fingerprint 134 along an X-base curve axis such as 140 will appear as being curved upward in the fingerprint image, as opposed to being colinear if imaged at an observation angle OA of ninety degrees.

A graphic representation of these curvature errors inherently produced by prism 20A is illustrated in FIG.

32 where an image of a line 254 is curved about an X-base curve axis such as 140 and positioned in groove 102. Although in theory the amount of curvature error changes for portions of fingerprint 134 at different X-base curve axes such as 140 along Y-base curve axis 141, in practice the amount of curvature error variation over the relatively small part of finger 132 which is imaged is small. Curvature errors at all points of fingerprint 134 along Y-axis 141 are therefore essentially equal.

Scale errors are also caused by the fact that fingerprint 134 is on a compound curved surface of finger 132, and is imaged at an observation angle OA other than ninety degrees with respect to longitudinal axis 139. As a result of being imaged at an observation angle OA, true distances of portions of fingerprint 134 along a given Y-base curve axis such as 141 will be distorted. For example, in the fingerprint image, two ridges 136 which are actually separated about Y-base curve axis 141 on the finger by a given amount will appear to be compressed and separated by a distance less than the given amount. Furthermore, this Y-axis scale error is not constant about Y-base curve axis 141 since observation angle OA increases as bottom surface 116 in fingertip portion 114 of groove 102 curves upward toward surface 100 in the direction of image propagation surface 106.

For similar reasons, X-axis scale errors are inherent in portions of the fingerprint image which represent portions of the fingerprint about an X-base curve axis such as 140. These X-axis scale errors are also nonlinear due to curvature of fingerprint 134 along its X-base curve axis 140. For example, portions of fingerprint 134 at its center (i.e., opposite the fingernail), and portions on its side, which are separated by a given distance along X-base curve axis 140 will appear to be separated by different distances in the fingerprint image. Distances on the side of finger 132 will be compressed with respect to those in the center of the fingerprint.

The curved or lensed nature of image propagation surface 106 of prism 20A magnifies the fingerprint image of fingerprint 134 before it is propagated therefrom. Since groove 102 is actually an elongated and compound curved surface, different portions of the groove, and therefore different portions of fingerprint 134 when finger 132 is placed within the groove, will be at different distances from image propagation surface 106. This factor coupled with well known geometric optic principles results in different portions of fingerprint 134 being magnified to different degrees or amounts. Portions of fingerprint 134 near tip 145 of finger 132 will be nearest surface 106 and magnified the least amount. Portions of fingerprint 134 near back 143 of finger 132 will be positioned furthest from surface 106 and magnified the most. Portions of fingerprint 134 near sides 144 (only one side is visible in FIG. 15) will be magnified by an amount between the amount of those portions at back 143 and tip 145.

The result of these different amounts of magnification is to partially correct for curvature and scale errors described above. Curvature and scale errors in the fingerprint image which correspond to portions of fingerprint 134 at sides 144 of finger 132 are reduced due to the magnification (i.e., the inherent compression is expanded). Scale errors in the fingerprint image which correspond to portions of fingerprint 134 at back 143 of finger 132 are also reduced for similar reasons. In general, the magnification properties of image propagation surface 106 of prism 20A have been found to reduce the curvature and scale errors in the fingerprint image.

Slap Print Prism

A first embodiment of slap print prism 18 is illustrated in FIGS. 16 and 17. Like individual finger prism 20A, slap print prism 18 has a first or finger-receiving surface 150, a second or light-receiving surface 154, a third or image propagation surface 156, a fourth or bottom surface 158, back surface 160, and side surfaces 162. Bottom surface 158 has a depth of dimension D20, and a width of dimension D21. Light-receiving surface 154 and back surface 160 are perpendicular to and have a height of dimensions D22 and D23, respectively, from bottom surface 158. Finger receiving surface 150 is planar, and forms an angle A5 with respect to bottom surface 158. Image propagation surface 156 is curved to function as a cylindrical lens, and has a radius of curvature of dimension D24 centered about a point at a distance of dimension D25 above the intersection of finger-receiving surface 150 and back surface 160, and a distance of dimension D26 toward light-receiving surface 154 from back surface 160. Image propagation surface 156 can therefore be characterized as a cylindrical lens having a radius of curvature about an imaginary horizontal axis 151 which is parallel to both back surface 160 and bottom surface 158. Dimension D21 of slap print prism 18 must be sufficient so as to enable a plurality of fingers (e.g., four fingers of a hand less the thumb) to be positioned on finger-receiving surface 150. In one preferred embodiment, dimension D21 is five inches. In the same embodiment, dimension D20 is 1.75 inches, dimension D22 is 1.38 inches, dimension D23 is 1.25 inches, dimension D24 is 1.00 inches, dimension D25 is 0.75, and dimension D26 is 0.88 inches.

Slap print rism 18 utilizes and operates on the same optical principles as that of individual fingerprint prism 20A described above. Bottom surface 158, side surfaces 162, and back surface 160 are coated with black paint so as to make these surfaces opaque. Slap print images of the four fingers of a hand, excluding the thumb, which are positioned on finger-receiving surface 150 will be propagated through image propagation surface 156. Valleys 138 of a finger such as 132 (FIG. 15) will be "dark" in the image, while ridges 136 will be light. The curved nature of image propagation surface 156 causes this surface to function as a lens, and magnifies the image in a direction corresponding to that along the longitudinal axis (i.e., Y-base curve axis) of the finger. This magnification partially corrects for scale errors along Y-base curve axis 141 (FIG. 15) due to the observation angle OA at which fingerprint 134 is imaged. Since finger-receiving surface 150 is planar, fingerprint 134 of a finger such as 132 is forced into a planar orientation when positioned on surface 150. As a result, X-axis curvature and scale errors in fingerprint images provided by slap print lens 18 are negligible compared to those of images provided by finger prisms such as 20A.

A second or alternative embodiment of the slap print prism, that being slap print prism 18', is illustrated in FIGS. 3A, 3B, 18 and 19. Slap print lens 18' is identical to slap print lens 18 previously described in all respects except for image propagation surface 156' which is coplanar with light-receiving surface 162. Image propagation surface 156' does not, therefore, magnify fingerprint images of fingers such as 132 positioned on finger-receiving surface 150. As a result, Y-axis scaling errors are not partially corrected. Slap print lens 18' functions in all other regards exactly like that of slap print lens 18 previously described.

Processor Subsystem

Processor subsystem 30 and its interrelationship to video camera 28, video monitor 14, printer 16, data terminal 6, LEDs 316A–316E and 318A–318E of display 13, LEDs 21A–21D of key pad 19, motor 76 and microswitches 87 and 89 is best described with reference to FIG. 20. As shown, processor subsystem 30 includes programmable computing means such as computer 200, random access memory or RAM 202, read only memory or ROM 204, and frame digitizer 206.

Fingerprint images from optics subsystem 22 are imaged by camera 28 through its objective lens. In response, camera 28 generates video signals which are representative of the fingerprint image. The video signals are then distributed to both video monitor 14 and frame digitizer 206. Video monitor 14 (which will typically be interfaced to microprocessor 200 through a video driver which is not shown) can thereby provide a real-time display of the fingerprint image being imaged by camera 28. In one preferred embodiment, camera 28 and monitor 14 are commercially available devices which utilize a standard raster and standard frame rates. Computer 200 is preferably a commercially available 32-bit microprocessor.

When an operator of fingerprinting system 10 observes on monitor 14 a fingerprint image they wish to "freeze" or record, key pad 19 will be appropriately actuated. In response, computer 200 will cause frame digitizer 206 to digitize the video signals of the frame being displayed on monitor 14, and provide digital image data characteristic of the "captured" fingerprint image to computer 200. The fingerprint image data is temporarily stored in RAM 202. Computer 200 then retrieves the fingerprint image data and processes it in accordance with image enhancement software programs which can be stored in ROM 204. Computer 200 thereby generates enhanced fingerprint image data. In response to operator control through data terminal 6, computer 200 can retrieve the enhanced image data from RAM 202 and provide it to video monitor 14. The enhanced fingerprint image can thereby be visually displayed. Alternatively, the operator can cause the enhanced image data to be propagated to printer 16 which will print the enhanced fingerprint image. Printer 16 is preferably a high resolution laser printer.

Frame digitizer 206 provides the digital image data in the form of an array of pixel values representative of the intensity of the fingerprint image at corresponding discrete or pixel locations. An image array IA of pixel values $PVn,m_I$ is illustrated in FIG. 21. Image array IA is formed of N rows and M columns of pixel values $PVn,m_I$. In one embodiment, image array IA is formed of N equal to four hundred and eighty rows and M equal to five hundred and twelve columns of pixel values $PVn,m_I$. Pixel values $PVn,m_I$ are digital values representative of the intensity of the fingerprint image at corresponding pixel locations PLn,m of image array IA. In one embodiment frame digitizer 206 includes an eight-bit analog-to-digital converter which converts the video signals to eight-bit pixel values $PVn,m_I$ characteristic of image intensity at corresponding pixel locations PLn,m. In this embodiment, an eight-bit pixel value $PVn,m_I$ representative of a decimal zero (i.e. "00000000") is a minimum pixel value PVMIN and characterizes a lowest intensity or darkest pixel location PLn,m. A pixel value representative of a decimal two hundred and fifty-six (i.e., "11111111") is a maximum pixel value PVMAX and represents a highest intensity or whitest pixel location. A pixel value $PVn,m_I$ representative of a digital 128 (i.e., "10101010") represents a pixel location PLn,m having an intensity half-way between the lowest and highest intensities(i.e., grey).

Having been generated by frame digitizer 206, pixel values $PVn,m_I$ of image array IA will be stored within RAM 202 at indexed locations corresponding to pixel locations PLn,m. Computer 200 will then retrieve image array pixel values $PVn,m_I$ and process them in accordance with a Noise Average software algorithm stored in ROM 204 to produce a noise averaged array NAA of pixel values $PVn,m_N$ (FIG. 22. Noise averaged pixel values $PVn,m_N$ are then temporarily stored within RAM 202 prior to implementation of subsequent image processing software algorithms. Following this approach, computer 200 generates an illumination equalized array IEA of illumination equalized pixel values $PVn,m_E$ in accordance with an Illumination Equalize algorithm, a directional filtered array DFA of directional filtered pixel values $PVn,m_D$ in accordance with a Directional Filter algorithm, and an unhaired array UA of unhaired (artifact removed) pixel values $PVn,m_U$ in accordance with an Unhair algorithm. Unhaired pixel values $PVn,m_U$ are then translated in position in accordance with a Curvature Correction algorithm to generate a curvature corrected array CCA of curvature corrected pixel values $PVn,m_C$. Curvature corrected pixel values $PVn,m_C$ are then scaled or translated in position, first vertically to produce a vertically scaled array VA of vertically scaled pixel values $PVn,m_V$, and then horizontally to produce a horizontally scaled array HA of horizontally scaled pixel values $PVn,m_H$. This processing is done in accordance with Vertical Scaling and Horizontal Scaling algorithms, respectively. Finally, the horizontally scaled array HA of pixel values $PVn,m_H$ is thresholded to produce a threshold array of thresholded values $PVn,m_T$ characteristic of the enhanced fingerprint image. The thresholded array of pixel values are then stored in RAM 202, and can be utilized by printer 16 to produce a printed record of the fingerprint image.

A. Noise Average

Figure 22:
FIG. 22 is a graphic representation of a noise averaged array of noise averaged pixel values generated by the processor subsystem shown in FIG. 20.

To initiate image processing, computer 200 will retrieve pixel values $PVn,m_I$ of image array IA (FIG. 21) from RAM 202, and process these pixel values in accordance with a Noise Average program stored within ROM 204. As a result of this processing, computer 200 generates a noise averaged array NAA of noise averaged pixel values $PVn,m_N$ as illustrated in FIG. 22. The Noise Average program removes random variations, or noise, in imaged pixel values $PVn,m_I$ which can be introduced for various reasons such as electronic or electromagnetic noise.

Each noise averaged pixel value $PVn,m_N$ at pixel locations PLn,m of noise averaged array NAA is computed as a function of weighted average of the particular image pixel value $PVn,m_I$ at the same pixel location PLn,m of image array IA, and a plurality of image pixel values $PVn,m_I$ at pixel locations PLn,m surrounding or in the area of the particular pixel value $PVn,m_I$ being noise averaged. In a preferred embodiment described below, noise averaged pixel values $PVn,m_N$ are computed as a function of a weighted average of a given image pixel value $PVn,m_I$, and pixel values $PVn,m_I$ at pixel locations $PLn,m$ of image array IA immediately adjacent to the given pixel value. A formula for computing noise averaged pixel values $PVn,m_N$ in accordance with a preferred weighted average function is described by Equation 1 below. Other weighted average functions can of course also be used.

$$PVn,m_N = [4PVn,m_I + 2(PVn - 1,m_I + \qquad \text{Eq. 1}$$
$$PVn,m + 1_I + PVn + 1,m_I + PVn,m - 1_I) +$$
$$PVn - 1,m - 1_I + PVn - 1,m + 1_I + PVn + 1,m + 1_I +$$
$$PVn + 1,m - 1_I]/16$$

The weighted average function of Equation 1 assigns the center pixel value $PVn,m_I$ (the particular pixel value to be noise averaged) a weight of four, adjacent side pixel values a weight of two, and adjacent corner pixel values a weight of one. Equation 2 below describes as an example the application of Equation 1 to a particular image pixel value $PV2,2_I$ to be noise averaged.

$$PV2,2_N = [4PV2,2_I + 2(PV1,2_I + PV2,3_I + \qquad \text{Eq. 2}$$
$$PV3,2_I + PV2,1_I) + PV1,1_I + PV1,3_I + PV3,3_I + PV3,1_I]/16.$$

It is evident that the weighted average function described by Equation 1 is not applicable to pixel values $PVn,m_I$ at pixel locations $PLn,m$ at the edge of image array IA (i.e., pixel values $PVn,m_I$ for $n=1$ and $1 \leq m \leq M$, for $1 \leq n \leq N$ and $m=1$, for $n=N$ and $1 \leq m \leq M$, for $1 \leq n \leq N$ and $m=M$). The reason is that there are no "adjacent" pixel values beyond the edge of image array IA. In one embodiment these "edge" pixel values are ignored by the Noise Average program since they likely represent unimportant portions of the fingerprint image anyway. The noise averaged pixel values $PVn,m_N$ at these edges are simply set equal to their corresponding pixel values $PVn,m_I$ in the image array, as described by Equation 3.

$$PVn,m_N = PVn,m_I \text{ for: } n = 1, 1 \leq m \leq M; \qquad \text{Eq. 3}$$
$$1 \leq n \leq N, m = 1;$$
$$n = N, 1 \leq m \leq M; \text{ and}$$
$$1 \leq n \leq N, m = M$$

Having generated a noise averaged array NA of pixel values $PVn,m_N$ in accordance with the above-described approach, computer 200 will store the noise averaged pixel values at indexed locations within RAM 202 for subsequent processing.

B. Illumination Equalize

In practice, the manner in which slap print prism 18' and finger prisms 20A≅20D are illuminated by lamps 31 and 53, respectively, results in varying amounts of light being propagated by the prisms to different portions of a fingerprint such as 134 (FIG. 15) being imaged. As a result, the illumination intensity level over each fingerprint image imaged by camera 28 will vary. However, it is desirable that the fingerprint be illuminated with a constant intensity throughout. This is effectively performed by computer 200 which processes pixel values $PVn,m_N$ of noise averaged array NAA in accordance with an illumination Equalize program stored in ROM 204, and generates an illumination equalized array IEA of illumination equalized pixel values $PVn,m_E$ illustrated in FIG. 23.

Figure 24:
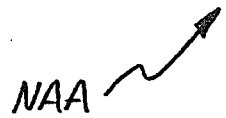
FIG. 24 is a graphic representation of the noise averaged array, illustrating a subarray of pixel values utilized by the processor subsystem to generate the illumination equalized array.

The generation of illumination equalized pixel values $PVn,m_E$ from noise averaged pixel values $PVn,m_N$ is described with reference to FIG. 24. For a particular pixel value $PVn,m_N$ at a particular pixel location $PLn,m$ that it is desired to illumination equalize, computer 200 first selects a subarray SA of pixel values which includes the pixel value to be illumination equalized. Although subarray SA has been chosen as a three-by-three subarray with the particular pixel value $PVn,m_N$ to be equalized in the center thereof for purposes of example in FIG. 24, subarrays of a larger size are preferred and can produce better results. In one embodiment, computer 200 selects an eight-by-eight subarray of pixel values surrounding the pixel value to be illumination equalized. However, the algorithm is fully described with the three-by-three subarray SA illustrated in FIG. 24.

Having selected a subarray $SAn,m$, for the particular pixel value $PVn,m_N$ to be equalized, computer 200 will sum all pixel values $PVn,m_N$ within the subarray, and divide by the number of pixel values summed, to generate a subarray average value $SAVn,m$. Equation 4 below mathematically describes this procedure for the general three-by-three subarray $SAn,m$ illustrated in FIG. 24.

$$SAVn,m = [PVn - 1,m - 1_N + PVn - 1,m_N + \qquad \text{Eq. 4}$$
$$PVn - 1,m + 1_N + PVn,m - 1_N + PVn,m_N + PVn,m + 1_N +$$
$$PVn + 1,m - 1_N + PVn + 1,m_N + PVn + 1,m + 1_N]/9$$

Computer 200 then computes the illumination equalized pixel value $PVn,m_E$ as a function of the particular noise averaged pixel value $PVn,m_N$ to be illumination equalized, the subarray average value $SAVn,m$ for the particular pixel value to be illumination equalized, and a constant K characteristic of an average illumination expected of pixel values of the image. Constant K (which can be stored in RAM 202 or ROM 204) is a threshold value and can be set as a function of noise in the fingerprint image. In one embodiment, constant K is representative of a pixel value $PVn,m$ having an intensity halfway between the lowest and highest intensities which can be displayed on monitor 14 (e.g., K=(PVMAX−PVMIN)/2). Following the above example which utilizes an eight-bit analog-to-digital converter in frame digitizer 206, K would equal one hundred and twenty-eight.

In the course of carrying out these computations, computer 200 first generates a pixel difference value $PDVn,m$ representative of the difference between the particular pixel value $PVn,m_N$ to be illumination equalized, and the subarray average value $SAVn,m$ of the subarray of which it is an element. This operation is mathematically described by Equation 5.

$$PDVn,m = PVn,m_N - SAVn,m. \qquad \text{EQ. 5}$$

Constant K is then added to pixel difference values $PVDn,m$ to generate an intermediate illumination equalized pixel value $IEPVn,m$ as described by Equation 6 below.

$$IEPVn,m = PDVn,m + K. \qquad \text{Eq. 6}$$

The illumination equalized pixel value $PVn,m_E$ is finally computed as a function of its corresponding intermediate illumination equalized pixel value IEPVn,m. If the intermediate illumination equalized pixel value IEPVn,m is less than the minimum pixel value PVMIN or greater than the maximum pixel value PVMAX, the illumination equalized pixel value $PVn,m_E$ is unconditionally set to PVMIN or PVMAX, respectively. The illumination equalized pixel value $PVn,m_E$ is set to the intermediate illumination equalized pixel value IEPVn,m if IEPVn,m is greater than or equal to the minimum pixel value PVMIN, and less than or equal to the maximum pixel value PVMAX. These relationships are mathematically described by Equations 7–9 below.

$$PVn,m_E = PVMIN \text{ if } IEPVn,m < PVMIN. \qquad \text{Eq. 7}$$

$$PVn,m_E = IEPVn,m \text{ if } PVMIN \leq IEPVn,m \leq PVMAX. \qquad \text{Eq. 8}$$

$$PVn,m_E = PVMAX \text{ if } IEPVn,m > PVMAX. \qquad \text{Eq. 9}$$

The procedures described above, including the selection of a subarray and the mathematical operations described by Equations 4–9, are carried out by computer 200 to generate an illumination equalized pixel value $PVn,m_E$ for each noise averaged pixel value $PVn,m_N$ to be illumination equalized. However, since subarrays SA are selected in such a manner that the pixel value $PVn,m_N$ to be illumination equalized is at or near its center, it is evident that this procedure cannot be used to illumination equalize pixel values $PVn,m_N$ near edges of noise averaged array NAA. For example, using the three-by-three subarray SA illustrated in FIG. 24, it will not be possible to illumination equalize the pixel values $PVn,m_N$ of the outermost rows and columns of noise averaged array NAA. Since these edge pixel values $PVn,m_N$ will likely represent unimportant parts of the fingerprint image, they are simply set equal to their noise averaged pixel values as described by Equation 10. A similar procedure is followed when using a subarray SA of larger size.

$$PVn,m_E = PVn,m_N \text{ for: } n = 1, 1 \leq m \leq M; \qquad \text{Eq. 10}$$
$$1 \leq n \leq N, m = 1;$$
$$n = N, 1 \leq m \leq M; \text{ and}$$
$$1 \leq n \leq N, m = M.$$

Following the above-described procedure, an entire illumination equalized array IEA of pixel values $PVn,m_E$ can be generated by computer 200. Computer 200 will store illumination equalized pixel values $PVn,m_E$ in RAM 202 for subsequent processing.

C. Directional Filter

Figure 25:
FIG. 25 is a graphic representation of a directional filtered array of directional filtered pixel values produced by the processor subsystem shown in FIG. 20.

The fingerprint image characterized by illumination equalized array IEA is formed by pixel values $PVn,m_E$ which represent relatively light curves characteristic of fingerprint ridges 136 (FIG. 15), and pixel values which represent relatively dark curves characteristic of fingerprint valleys 138. To enhance the fingerprint image represented by illumination equalized array IEA, it has been found advantageous to filter pixel values $PVn,m_E$ in such a way as to emphasize the directional aspects of portions of the array representing fingerprint ridges 136 and valleys 138. This directional filtering is performed by computer 200 in accordance with a Directional Filter program stored within ROM 204. The result is a directional filtered array DFA of directional filtered pixel values $PVn,m_D$ as illustrated in FIG. 25.

Generally stated, the Directional Filtering program is implemented by computer 200 in a multiple-step manner. First, for each particular pixel value $PVn,m_E$ for $1 < n < N$, $1 \leq m < M$ of illumination equalized array IEA (i.e., for all pixel values $pVn,m_E$ other than those in the top and bottom rows and rightmost column) computer 200 computes an absolute value of the difference between that particular pixel value and a horizontally adjacent pixel value (HorizDif), a vertically adjacent pixel value (VertDif), an adjacent pixel value at a positive slope (PosDif) and an adjacent pixel value at a negative slope (NegDif). This procedure is described generally by Equations 11–14 below.

$$HorizDifn,m = |PVn,m_E - PVn,m+1_E| \qquad \text{Eq. 11}$$

$$VertDifn,m = |PVn,m_E - PVn+1,m_E| \qquad \text{Eq. 12}$$

$$PosDifn,m = |PVn,m_E - PVn-1,m+1_E| \qquad \text{Eq. 13}$$

$$NegDifn,m = |PVn,m_E - PVn+1, m+1_E| \qquad \text{Eq. 14}$$

Horizontal difference values HorizDifn,m, vertical difference values VertDifn,m, positive difference values PosDifn,m and negative difference values NegDifn,m for pixel values $PVn,m_E$ for each $1 < n < N$ and $1 \leq m < M$ are stored at indexed locations within RAM 202.

Figure 26:
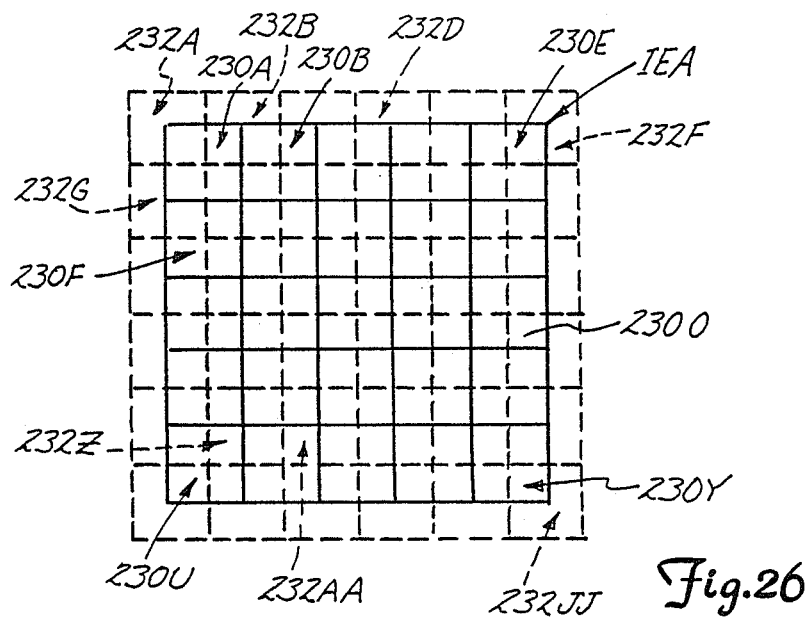
FIG. 26 is a graphic representation of an illumination equalized array illustrating the regular and offset subarrays utilized by the processor subsystem shown in FIG. 20 to produce the directional filtered array.

As illustrated graphically in FIG. 26, computer 200 next divides illumination equalized array IEA into a plurality of regular subarrays 230A–230Y (illustrated with solid lines) and offset subarrays 232A–232JJ (illustrated with broken lines). Offset subarrays 232A–232JJ are offset both horizontally and vertically with respect to regular subarrays 230A–230Y in the embodiment shown. All pixel values $PVn,m_E$ of illumination equalized array IEA will be located within both one of regular subarrays 230A–230Y and one of offset subarrays 232A–232JJ. Subarrays 230A–230Y and 232A–232JJ are sized so as to have more pixel values $PVn,m_E$ on a side than an expected width of a fingerprint ridge 136 (FIG. 15) or valley 138 as represented by the pixel values of the subarray. In one embodiment, computer 200 causes subarrays 230A–230Y and 232A–232JJ to be rectangular with 32 pixel values $PVn,m_E$ per side when processing an image from a finger prism such as 20A.

Computer 200 next determines a "dominant direction" of the portion of the fingerprint image represented by pixel values $PVn,m_E$ of each regular subarray 230A–230Y and each offset subarray 232A–232JJ. This is done as a function of the difference values HorizDifn,m, VertDifn,m, PosDifn,m, and NegDifn,m computed for the pixel values $PVn,m_E$ within that particular subarray 230A–230Y and 232A–232JJ. This is done by computing, for each subarray 230A–230Y and 232A–232JJ, a sum HDSum, VDSum, PDSum, and NDSum of the difference values HorizDifn,m, VertDifn,m, PosDifn,m, and NegDifn,m, respectively, which were previously computed for pixel values $PVn,m_E$ within that subarray. This procedure is mathematically described by Equations 15–22.

$HDSum_{230xx} = \Sigma HorizDifn,m$   Eq. 15   (For all $PVn,m_E$ of
$VDSum_{230xx} = \Sigma VertDifn,m$   Eq. 16   subarray 230xx for

| | | |
|---|---|---|
| PDSum$_{230xx}$ = ΣPosDifn,m | Eq. 17 | which difference values |
| NDSum$_{230xx}$ = ΣNegDifn,m | Eq. 18 | were computed) |
| HDSum$_{232xx}$ = ΣHorizDifn,m | Eq. 19 | (For all PVn,m$_E$ of |
| VDSum$_{232xx}$ = ΣVertDifn,m | Eq. 20 | subarray 232xx for |
| PDSum$_{232xx}$ = ΣPosDifn,m | Eq. 21 | which difference values |
| NDSum$_{232xx}$ = ΣNegDifn,m | Eq. 22 | were computed) |

An understanding of the operations described by Equations 15-22 is facilitated by FIG. 27, in which regular subarrays 230A-230Y and offset subarrays 232A-232JJ are sized to have four pixel values PVn,m$_E$ per side for purposes of example. It will be understood that for most subarrays 230A-230Y and 232A-232JJ (those which do not include pixel values PVn,m$_E$ in the top or bottom rows or rightmost column), difference values HorizDifn,m, VertDifn,m, PosDifn,m, and Neg-Difn,m for all pixel values PVn,m$_E$ within the subarray will have been computed and will be summed. However, for those subarrays which have pixel values PVn,m$_E$ in the top or bottom rows or rightmost column of illumination equalized array IEA, not all of the pixel values therein will have had difference values Horiz-Difn,m, VertDifn,m, PosDifn,m, and NegDifn,m, computed therefor. As a result, only those pixel values PVn,m$_E$ for which difference values were computed can be summed to contribute to difference value sums HDSum, VDSum, PDSum and HDSum of subarrays 230A-230Y and 232A-232JJ. As an example, for offset subarray 232A in FIG. 27, only pixel value PV2,2$_E$ had difference values computed therefor.

Following the above description, HDSum$_{232A}$=-HorizDif2,2, VDSum$_{232A}$=VertDif2,2, PDSum$_{232A}$=-PosDif2,2, and NDSum$_{232A}$=NegDif2,2. Also by way of example, for regular array 230A, HDSum$_{230A}$=-HorizDif2,2+HorizDif2,3+HorizDif2,4+HorizDif 3,2+HorizDif3,3+HorizDif3,4+HorizDif4,2+HorizDif4,3+HorizDif4,4.

Computer 200 next determines the dominant direction of each regular subarray 230A-230Y and offset subarray 232A-232JJ as a function of the difference value sums of that subarray. In particular, the dominant direction for a subarray 230xx is the direction or orientation associated with the lesser of HDSum$_{230xx}$, VDSum$_{230xx}$, PDSum$_{230xx}$ or NDSum$_{230xx}$ of that subarray 230xx. Similarly, the dominant direction of an offset subarray 232xx is the direction associated with the lesser of HDSum$_{232xx}$, VDSum$_{232xx}$, PDSum$_{232xx}$, or NDSum$_{232xx}$. In those cases in which more than one of the difference value sums are equal, the dominant direction is that direction which is 90° offset from the direction characterized by the greatest difference value sum.

Having determined the dominant directions, computer 200 performs a directional filter of each pixel value PVn,m$_E$ of image array IEA as a function of a weighted average of the particular pixel value and adjacent pixel values in the dominant direction the subarrays 230A-230Y, 232A-232JJ of which the particular pixel value is an element.

A preferred embodiment of this directional filtering is best described as follows. First, each pixel value PVn,m$_E$ is directional filtered as a function of the dominant direction of the regular subarray 230A-230Y of which it is a member to provide a regular subarray directional filtered pixel value RSPVn,m$_E$. Second, each pixel value is directional filtered as a function of the dominant direction of the offset subarray 232A-232JJ to provide an offset subarray directional filtered pixel value OSPVn,m$_E$ of which it is a member. Finally, the regular subarray directional filtered pixel value RSPVn,m$_E$ and offset subarray directional filtered pixel value OSPVn,m$_E$ are averaged to generate the corresponding directional filtered pixel value PVn,m$_D$ of directional filtered array DFA.

Preferred weighted average formulas for generating regular subarray directional filtered pixel values RSPVn,m$_E$ for a particular pixel value PVn,m$_E$ are described by equations 23-26.

| | | |
|---|---|---|
| RSPVn,m$_E$ = | (2 PVn,m$_E$ + PVn,m − 1$_E$ + PVn,m + 1$_E$)/4 (when the dominant direction of the regular subarray is horizontal) | Eq. 23 |
| RSPVn,m$_E$ = | (2 PVn,m$_E$ + PVn − 1,m$_E$ + PVn + 1,m$_E$)/4 (when the dominant direction of the regular subarray is vertical). | Eq. 24 |
| RSPVn,m$_E$ = | (2PVn,m$_E$ + PVn − 1, m + 1$_E$ + PVn + 1, m − 1$_E$)/4 (when the dominant direction of the regular subarray is positive slope). | Eq. 25 |
| RSPVn,m$_E$ = | (2PVn,m$_E$ + PVn − 1,m − 1$_E$ + PVn + 1,m + 1$_E$)/4 (when the dominant direction of the regular subarray is negative slope). | Eq. 26 |
| | Offset subarray directional filtered pixel values OSPVn,m$_E$ can be computed in a similar manner using equations 27-30. | |
| OSPVn,m$_E$ = | (2PVn,m$_E$ + PVn,m − 1$_E$ + PVn,m + 1$_E$)/4 (if the dominant direction of the offset subarray is horizontal). | Eq. 27 |
| OSPVn,m$_E$ = | (2PVn,m$_E$ + PVn − 1,m$_E$ + PVn + 1,m$_E$)/4 (if the dominant direction of the offset subarray is vertical). | Eq. 28 |
| OSPVn,m$_E$ = | (2PVn,m$_E$ + PVn − 1,m + 1$_E$ + PVn + 1,m − 1$_E$)/4 (if the dominant direction of the offset subarray is positive slope). | Eq. 29 |
| OSPVn,m$_E$ = | (2PVn,m$_E$ + PVn − 1,m − 1$_E$ + PVn + 1,m + 1$_E$)/4 (if the dominant direction of the offset subarray is negative slope). | Eq. 30 |

Directional filtered pixel values PVn,m$_D$ are generated by computer 200 by averaging corresponding regular subarray pixel values RSPVn,m$_E$ and offset subarray pixel values OSPVn,m$_E$. The procedure is described mathematically by Equation 31.

$$PVn,m_D = (RSPVn,m_E + OSPVn,m_E)/2 \qquad \text{Eq. 31}$$

Following the above-described procedure, computer 200 can generate a directional filtered array DFA of directional filtered pixel values $PVn,m_D$ as illustrated in FIG. 25. For pixel values $PVn,m_E$ in the top and bottom rows and rightmost column of illumination equalized array IEA which are not directional filtered, computer 200 sets their corresponding directional filtered pixel value equal to their illumination equalized pixel value, as described by equation 32 below. This procedure will not materially affect the image represented by directional filtered array DFA since these pixel values are on the edges.

$$PVn,m_D = PVn,m_E \text{ for: } \quad n = 1, 1 \leq m < M \qquad \text{Eq. 32}$$
$$n = N, 1 \leq m < M$$
$$1 \leq n \leq N, m = M$$

D. Unhair

The fingerprint image represented by directional filtered array DFA will typically include artifacts of "hairs" which are undesirable noise components of the image. Artifacts such as 240 are shown within fingerprint image 242 in FIG. 28. As is evident from FIG. 28, artifacts 240 typically are finer than or have a width which is less than either valleys 138 or ridges 136 of the fingerprint image. To enhance the image represented by directional filtered array DFA, computer 200 "unhairs" the image by processing this array in accordance with an Unhair program stored within ROM 204. The result is an artifact removed or unhaired array UA of unhaired pixel values $PVn,m_U$ illustrated in FIG. 29.

Figure 28:
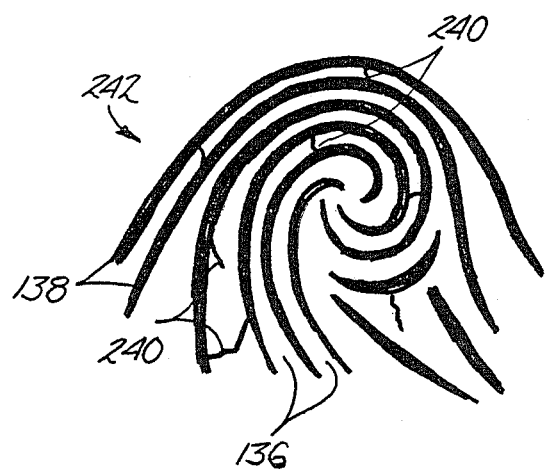
FIG. 28 is a graphic representation of a fingerprint image showing artifacts or hairs therein.
Figure 30:
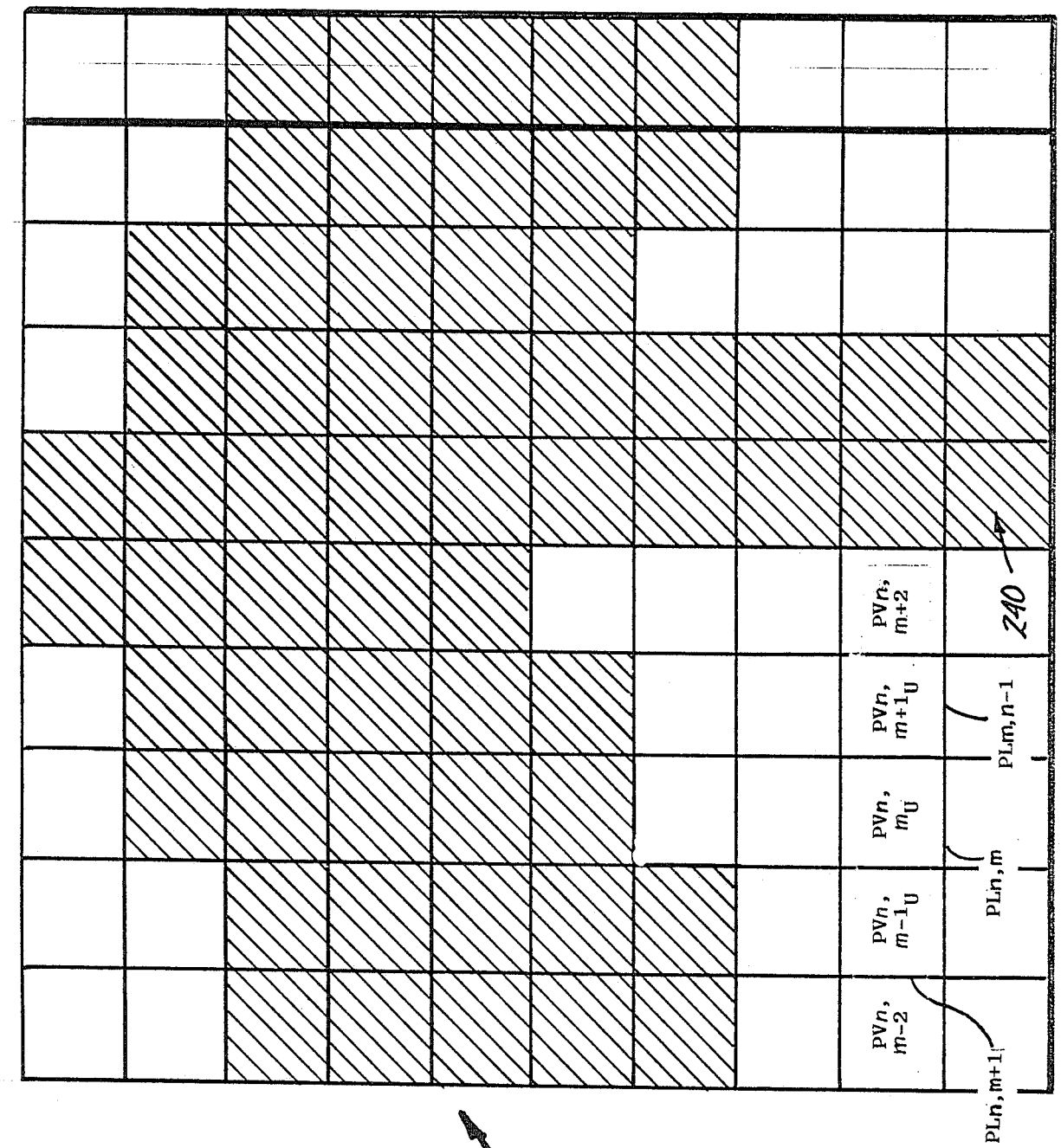
FIG. 30 is a graphic representation of a directional filtered array illustrating a portion of a fingerprint image having an artifact or hair therein.

The Unhair program implemented by computer 200 operates on the assumption that artifacts 240 will have a width which is less than the width of either valleys 138 or ridges 136 of a fingerprint image such as 242 illustrated in FIG. 28 (as represented by directional filtered array DFA). It is therefore assumed that the width of valleys 138 and ridges 136 will occupy a minimum number of adjacent pixel locations PLn,m of directional filtered array DFA, while the width of an artifact 240 will occupy less than the number of adjacent pixel locations of a valley or ridge. A graphic representation of a portion of directional filtered array DFA illustrating a valley 138 and artifact 240 is illustrated in FIG. 30. It must be understood that the shading in FIG. 30 is merely for purposes of illustration, and is actual representative of the magnitude of pixel values $PVn,m_D$ at the corresponding pixel locations PLn,m. In FIG. 30, artifact 240 is vertically oriented and has a width of two pixel locations PLn,m, while valley 138 has a minimum width of five "occupied" pixel locations PLn,m.

Data representative of the width of artifacts 240 that it is desired to remove, in terms of a number W of adjacent pixel locations PLn,m this width would occupy, is stored in RAM 202 or ROM 204. In one embodiment, it is assumed that a vertical "feature" of fingerprint image 242 which has a width less than W equals two pixel locations PLn,m is an artifact 240. Any vertically oriented features which are not more than W pixel locations PLn,m wide are deemed to be artifacts 240, and the pixel values $PVn,m_D$ representing these features are unconditionally set to a value of PVMAX so as to eliminate these features from the image.

Following the Unhair program to eliminate vertically oriented artifacts 240, computer 200 processes groups of $W+2$ horizontally adjacent pixel values $PVn,m_D$ of directional filtered array DFA, i.e., $PVn,m-1_D$, $PVn,m_D$, $PVn,m+1_D$, ... $PVn,m+W_D$. Each of these pixel values must be compared to an unhair threshold value UT to determine if it is representative of a dark portion image 242 (i.e., a valley 138 or artifact 240), or a light portion (i.e., a ridge 136). Pixel values $PVn,m_D$ which are less than threshold value UT are deemed to represent dark portions of image 242, while those greater than or equal to threshold value UT are deemed to represent light portions of the image. Threshold value UT can be stored in RAM 204, and be equal to (PVMAX − PVMIN)/2.

Computer 200 first looks to a group of W horizontally adjacent pixel values PVn,m to PVn,m+(W−1). If each of these values is less than the threshold value UT, then they are known to represent a dark feature of image 242. If this feature is a fingerprint valley 138, then one of the pixel values PVn,m adjacent to this group (i.e., one of PVn,m−1 or PVn,m+W) will also be dark, i.e., less than threshold UT. If this is the case, then the corresponding unhaired pixel value $PVn,m_U$ is set to the value of its corresponding directional filtered pixel value $PVn,m_D$. This relationship is mathematically described by Equation 32a below.

If the group of W adjacent pixel values PVn,m to PVn,m+(W−1) are all less than the threshold UT but both adjacent pixel values PVn,m−1 and PVn,m+W are greater than or equal to the threshold UT, the group of W adjacent pixel values represent an artifact, and computer 200 sets all pixel values $PVn,m-1_U$ to $PVn,m+W_U$ equal to PVMAX, thereby eliminating the artifact from the image. This relationship is mathematically described by Equation 32b and takes precedence over equation 32a. That is, a pixel value $PVn,m_U$ initially set in accordance with equation 32a can subsequently be set to PVMAX in accordance with equation 32b.

Finally, computer 200 will set pixel values $PVn,m_U$ equal to the corresponding value $PVn,m_D$ in directional filtered array DFA if not all W adjacent pixels PVn,m to PVn,m+(W−1) of the group are less than threshold UT. This relationship is described mathematically by equation 32a. Once the above procedure has been implemented for all pixel values PVn,m for $1 \leq n \leq N$, $2 \leq m \leq M - W$, an unhaired array UA is generated. The Unhair program is not performed on edge pixel values $PVn,m_D$ for $1 < n < N$, $M-W < m \leq M$. For these pixel values, $PVn,m_U$ are set equal to $PVn,m_D$ in accordance with Equation 32c.

For each PVn,m for $1 \leq n \leq N$, $2 \leq m \leq M - W$. If $PVn,m_D$ and $PVn,m+1_D$ . . . and $PVn,m+(W-1)_D < UT$ and: $PVn,m-1_D$ or $PVn,m+W_D < UT$
or if any of $PVn,m_D$, $PVn,m+1_D$, . . . $PVn,m+(W-1)_D > UT$ then:

$$PVn,m_U = PVn,m_D \qquad \text{Eq. 32a}$$

If $PVn,m_D$ and $PVn,m+1_D$, . . . and $PVn,m+(W-1)_D < UT$ and: $PVn,m-1_D$ and $PVn,m+W_D \geq UT$ then:

$$PVn,m-1_D, PVn,m_D, \ldots \text{ and}$$
$$PVn,m+W_D = PVMAX \qquad \text{Eq. 32b}$$

$$PVn,m_U = PVn,m_D \text{ for } 1 < n < N, M-W < m \leq M. \qquad \text{Eq. 32c}$$

Horizontally oriented artifacts can be removed in a similar manner using groups of W vertically adjacent pixel values $PVn,m_D$. However, experience has shown most artifacts 240 to be vertically oriented.

E. Curvature Correction

As previously discussed, since finger prisms 20A–20D provide fingerprint images which are taken at an observation angle OA with respect to a longitudinal axis 139 of finger 132 (FIG. 15), those portions of the fingerprint which are positioned adjacent one another about an X-base curve axis 140 at any given point about the longitudinal axis and which would be linearly positioned with respect to one another in a rolled fingerprint image, will actually be projected in such a manner as to appear to be curved in an upwardly arced manner within unhaired array UA. Computer 200 processes pixel vales $PVn,m_U$ of unhaired array UA in accordance with a Curvature Correction program to produce a curvature corrected array CCA (FIG. 31) of curvature corrected pixel values $PVn,m_C$ which characterize the fingerprint image in a curvature corrected manner. Basically, the Curvature Correction program causes unhaired pixel values $PVn,m_U$ to be translated vertically in position in acordance with tabulated curvature correction data characteristic of the curvature inherent in images provided by prisms 20A–20D.

Figure 32:
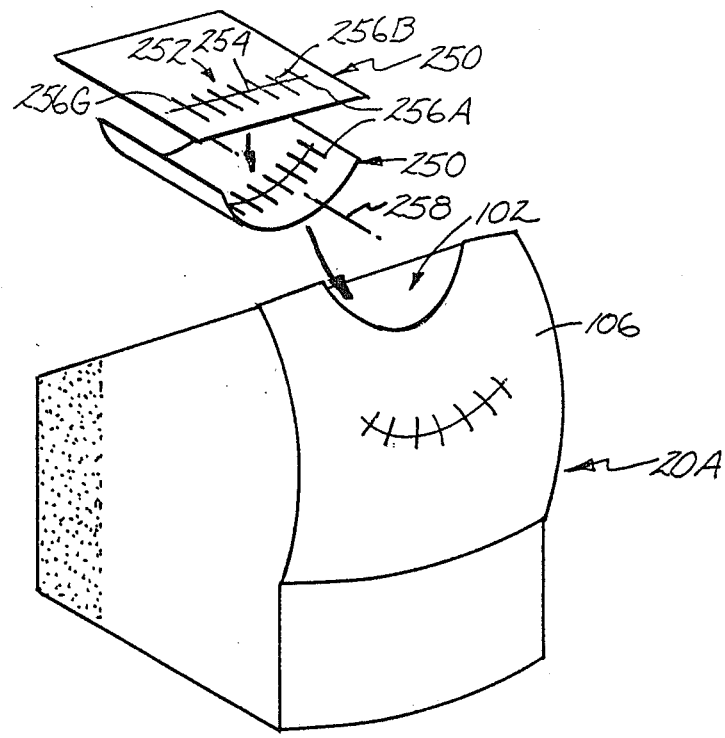
FIG. 32 is a view illustrating a template having a pattern of indicia thereon, and an image of the pattern of indicia when the template is positioned on the finger prism shown in FIG. 6.
Figures 33, 34:
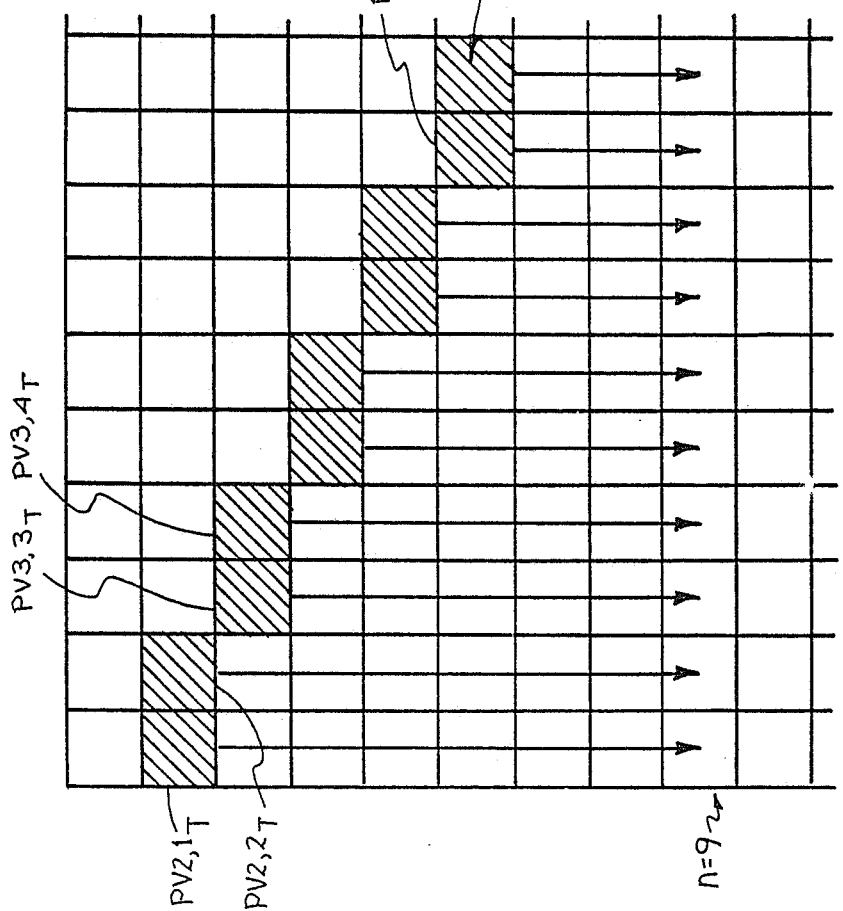
FIG. 33 is a qraphic repesentation of a curvature correction table of curvature correction data generated and used by the processor subsystem shown in FIG. 20 to produce the curvature corrected array shown in FIG. 31.
FIG. 34 is a graphic representation of a template image array of template image pixel values generated by the processor subsystem shown in FIG. 20 and representing an image of the pattern of indicia shown in FIG. 32.

Curvature correction data is generated by computer 200 through the use of a flexible template 250 as illustrated in FIG. 32. As shown, template 250 has a linear pattern of indicia 252 which can include a line 254 and hatch marks 256A–256G at known and preferably evenly spaced locations thereabout. Template 250 is shaped in such a manner as to correspond to the curvature of the finger, with line 254 oriented perpendicular to an imaginary axis 139 representing the longitudinal axis of finger 132. Line 254 will therefore be parallel to an X-base curve axis 140 of finger 132. Shaped template 250 is then positioned within groove 102 of prism 20A with pattern of indicia 252 oriented in the above-identified manner. As a result of the optical transfer function of prism 20A, the image of line 254 propagated from face 106 of prism 20A will be shaped in the form of an arc opening upward. A graphical illustration of this image as represented by template image array TIA is shown in FIG. 34. Although line 254 is graphically illustrated in FIG. 34, it is to be understood that the shading is actually represented by the magnitude pixel values $PVn,m_T$ at the particular pixel locations.

Curvature correction data is generated from template image array TIA in the following manner. All curvature distortion inherent in the transfer function of prism 20A occurs along a y-axis parallel to a vertical line through the longitudinal axis of the finger when positioned in groove 102 of prism 20A (and generally parallel to surface 106). Furthermore, it is assumed that all pixel values $PVn,m$ for any column $1 \leq m \leq M$ within template image array TIA are distorted by the same amount. That is, the amount of distortion for all pixel values $PV1 \leq n \leq N,M$, for example, are equal.

Were line 254 undistorted by the optical properties of prism 20A, the pixel values $PVn,m$ representing line 254 (e.g., $PV2,1_T$, $PV2,2_T$, $PV3,3_T$, $PV3,4_T$) would all be adjacent one another in the same row (e.g., n=9) within template image array TIA. Curvature correction data for pixel values $PVn,m_T$ for each column $1 \leq m \leq M$ can therefore be defined in terms of an offset OFFm from an expected position, where m is the column within array TIA. For purposes of example, it will be assumed that all of the pixel values illustrated in FIG. 34 which represent line 254 should actually be positioned in row n=9. Offsets OFFm can be expressed in terms of the number of pixel locations $PLn,m$ by which the pixel value $PVn,m_T$ is vertically displaced from its proper location (e.g. row n=9). Using the example shown in FIG. 32, OFF1 and OFF2 equal seven, OFF3 and OFF4 equal six and OFF9 and OFF10 equal three. Following this procedure, a curvature correction table of curvature correction or offset data OFF1–OFFM (illustrated in FIG. 33 for array TIA shown in FIG. 34) is generated by computer 200 and stored in RAM 202 or ROM 204.

Computer 200 utilizes the offset data in the curvature correction table to generate curvature corrected array CCA of curvature corrected pixel values $PVn,m_C$ from unhaired array UA. Computer 200 does this by determining pixel values $PVn,m_C$ of curvature corrected array CCA as a function of the pixel values $PVn,m_U$ in the unhaired array and offsets OFFm, as described by equation 33, below.

$$PVn,m_C = PVn - OFFm,m_U \qquad \text{Eq. 33.}$$

Using the offsets of the example illustrated in FIG. 32 and described above and in the table illustrated in FIG. 33, for example, $PV9,1_C = PV9-7,1_U = PV2,1_U$, $PV9,9_C = PV9-3,9_U = PV6,9_U$. Similarly $PV10,9_C = PV7,9_U$.

Following the above procedur a curvature corrected array CCA of curvature corrected pixel values $PVn,m_C$ can be produced. For those pixel values $PVn,m_C$ for $1 \leq n < OFFm$ of a given row $1 \leq m \leq M$ of curvature corrected array CCA there will obliously be no pixel values $PVh,m_U$ within unhaired array VA to "translate." These pixel values $PVn,m_C$ are simply set equal to PVMAX or PVMIN, as they define the edge of the fingerprint image represented by array CCA.

The above procedure has been described for finger prism 20A. However, due to the different characteristics of groove 102 of prisms 20A–20D, a separate table of curvature correction data such as that illustrated in FIG. 33 will be generated by computer 200 for each prism. Computer 200 will then utilize the table of curvature correction data corresponding to the particular prism 20A–20D from which the image being processed was propagated, to curvature correct the unhaired array UA representative of the image.

F. Vertical Scaling

As previously discussed, fingerprint images produced by finger prisms 20A–20D and slap print prisms 18 and 18′ will have vertical or Y-axis size or scale errors due to the observation OA at which fingerprint 134 of finger 132 is imaged (FIG. 15). This vertical scale error is compounded on fingerprint images produced by finger prisms 20A–20D since portions of fingerprint 134 near tip 145 curve upward, effectively increasing the observation angle at these locations. This vertical scale error can also be thought of a paralax error. Since the image is taken at an angle other than 90° with respect to the "plane" of the fingerprint, true distances along Y-axis 141 which are parallel to the longitudinal axis 139 of finger 132 are "compressed", along the vertical axis of the fingerprint image such as that represented by curvature corrected array CCA. In other portions of the image, distances about Y-axis 141 can be "expanded" from their true distance on the fingerprint.

Figure 35:
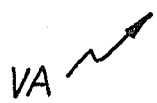
FIG. 35 is a graphic representation of a vertically scaled array of vertically scaled pixel values generated by the processor subsystem shown in FIG. 20.

To correct those vertical scale errors, computer 200 processes curvature corrected array CCA in accordance with a Vertical Scaling program to generate a vertically scaled array VA of vertically scaled pixel values $PVn,m_V$ as illustrated in FIG. 35. A table of vertical scale correction data is generated for each prism 20A–20D, 18 and 18' within system 10, and stored in either RAM 202 or ROM 204. Computer 200 utilizes the table of vertical scale correction data to generate vertically scaled array VA.

Figure 36:
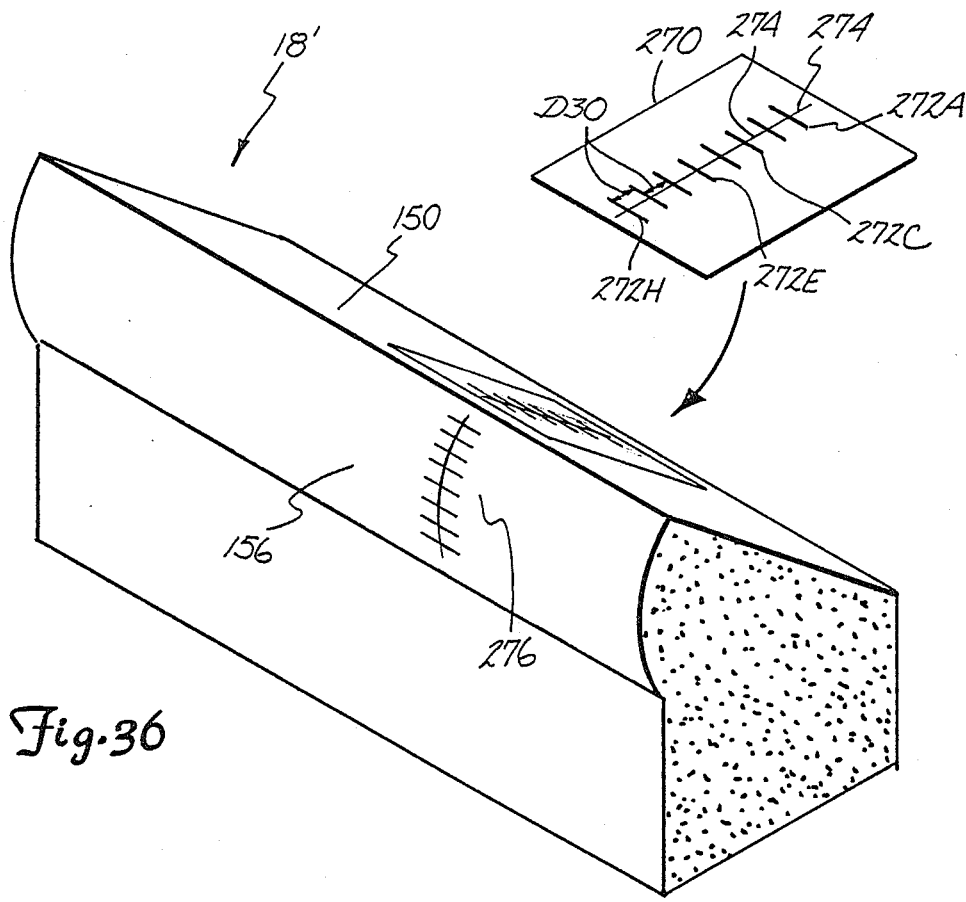
FIG. 36 is a view illustrating a template having a pattern of indicia thereon, and an image of the pattern of indicia when the template is positioned on the slap print prism shown in FIG. 16.

The generation of the table of vertical scale correction data for prism 18 (which is representative of a generation of vertical scaling correction data for prisms 20A–20D and 18') is described with reference to FIG. 36. As shown, a template 270 will have a pattern of indicia 272A–272H which are spaced about a Y-axis 274 by known and preferably equal distances D30. Template 270 is positioned on finger-receiving surface 150 of prism 18 with axis 274 oriented parallel to a longitudinal axis such as 139 of a finger such as 132 when positioned on prism 18. An image 276 of the pattern of indicia 272A–272H will be propagated from image propagation surface 156, imaged by camera 28 (FIG. 2), and the data representative of this image processed by computer 200 in accordance with the various programs described above until a curvature corrected array CCA of image 276 is generated.

Figure 37:
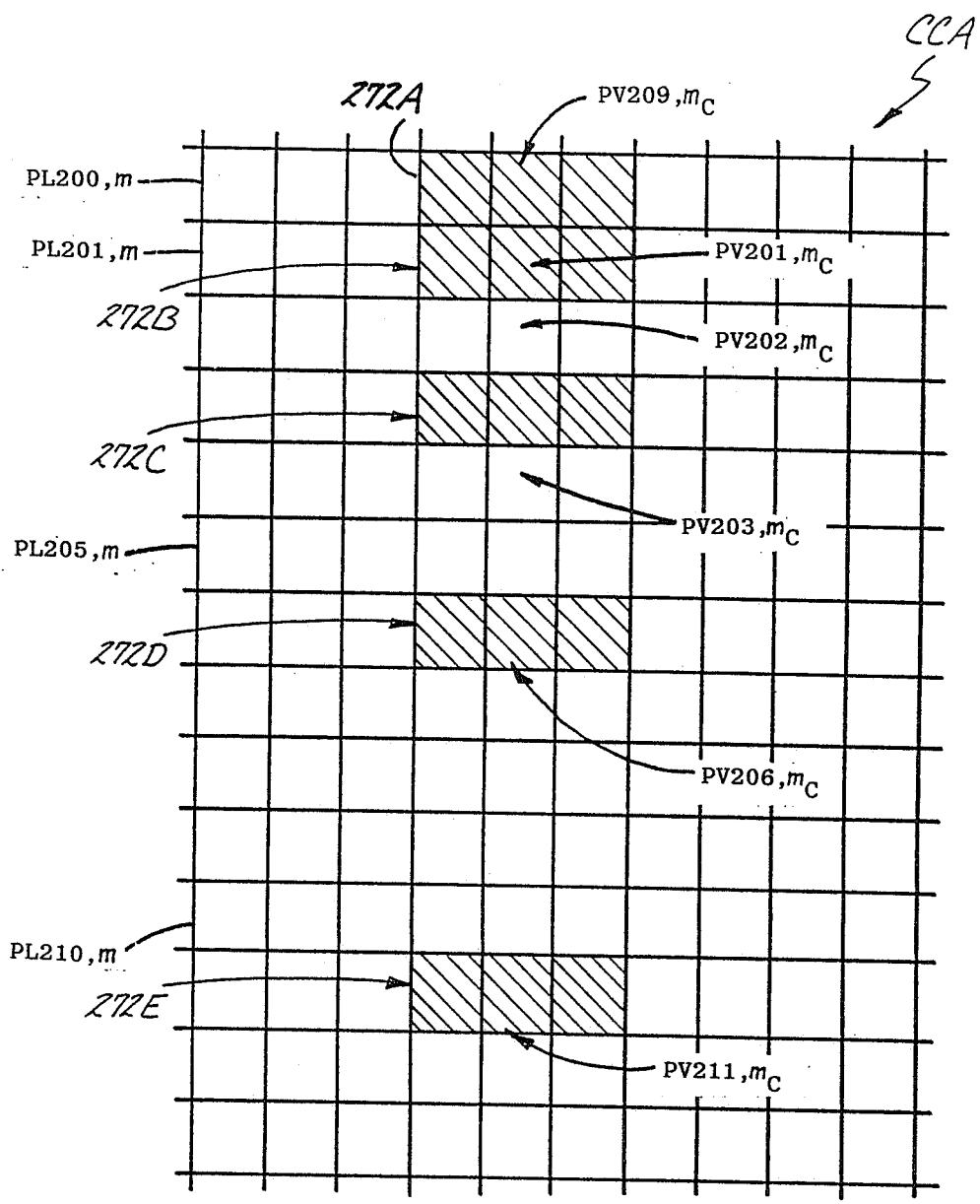
FIG. 37 is a graphic representation of a curvature corrected array generated by the processor subsystem shown in FIG. 20 and representative of the image of the pattern of indicia shown in FIG. 36.

A portion of a curvature corrected array CCA representative of image 276 and the pattern of indicia 272A–272H is illustrated diagramatically in FIG. 37. Indicia 272A–272E are illustrated graphically in FIG. 37 for purposes of example. However, it is to be understood that the magnitude of the image at the particular pixel locations of indicia 272A–272H in curvature corrected array CCA are actually represented by pixel values $PVn,m_C$.

Since indicia 272A–272H are separated by known distances on template 270, these known distances would correspond to predetermined numbers of pixel location PLn,m in the vertical or "n" direction of curvature corrected array CCA. In the embodiment of template 270 illustrated in FIG. 36, indicia 272A–272H are separated by equal known distances D30. Were there no vertical scale error, the representation of each indicia 272A–272H would be separated from each other in the vertical direction of array CCA by the same predetermined number (e.g., three) pixel locations PLn,m. However, due to the scale errors inherent in prism 18, indicia 272A–272H will be separated by differing numbers of pixel locations PLn,m. In the example shown in FIG. 37, indicia 272A and 272B are compressed, separated by no pixel locations PLn,m, and adjacent to one another. Indicia 272B and 272C are also compressed, but not quite as much, and are separated by one pixel location PLn,m. Indicia 272D and 272E, on the other hand, are vertically expanded from their normal positional relationship, and separated by four pixel locations PLn,m.

A table 280 of vertical scale correction data generated by computer 200 is illustrated graphically in FIG. 38. Data within table 280 characterizes locations of pixel values $PVn,m_V$ in vertically scaled array VA as a function of the vertical location within curvature corrected array CCA at which the pixel value should be taken. With respect to FIG. 37, for example, it is assumed that pixel values $PV200,m_C$ will be correctly positioned in the same row of vertically scaled array VA. That is, pixel values $PV200,m_V = PV200,m_C$. However, it is known that indicia 272B should be spaced from 72A by three pixel locations PLn,m in the example used above. Pixel values $PV201,m_C$ of curvature corrected array CCA should therefore be positioned in row 204 of vertically scaled array VA. Table 280, therefore, includes data which characterizes pixel values $PV204,m_V$ as being equal to pixel values $PV201,m_C$ of curvature corrected array CCA.

Since indicia 272A and 272B were compressed due to the optical transfer properties of prism 18, information therebetween is lost. Computer 200 thereby "fills in" this lost information by inserting or repeating pixel values $PV201,m_V - PV203,m_V$ of vertically scaled array VA with information at one of either pixel values $PV200,m_C$ or $PV201,m_C$ of the curvature corrected array CCA. In the embodiment shown in FIG. 38, all pixel values $PV201,m_V - PV203,m_V$ are set equal to pixel value $PV201,m_C$ of curvature corrected array CCA.

Following the above example, it is also known that indicia 272C should be spaced vertically from indicia 272B by three pixel locations PLn,m. All pixel values $PV203,m_C$ of the 203rd row in curvature corrected array CCA should therefore actually be positioned in the 208th row of vertically scaled array VA. Accordingly, computer 200 generates data within table 280 associating pixel values $PV203,m_C$ of curvature corrected array CCA with pixel values $PV208,m_V$ of the vertically scaled array VA. Portions of the image which were lost due to compression between indicia 272B and 272C are "filled in" by repeating pixel values $PV202,m_C$ of the curvature corrected array CCA at pixel values $PV205,m_V - PV207,m_V$ of vertically scaled array VA. Data characteristic of this filling in or repetition of pixel values is characterized in table 280. Procedures similar to those described above are repeated for pixel value $PV212,m_V$ of vertically scaled array VA which should actually be equal to pixel values $PV206,m_C$ in curvature corrected array CCA.

Indicia 272D and 272E would also be separated by three pixel locations PLn,m were no vertical scaling errors inherent in prism 18. However, indicia 272D and 272E have been "expanded" by the optical properties of prism 18, and they are actually separated by four pixel locations PLn,m. In other words, pixel values $PV211,m_C$ in curvature corrected array CCA should actually be spaced from pixel values $PV212,m_V$ of vertical scaled array VA (which correspond to pixel values $PV206,m_C$ in curvature corrected array CCA) by three pixel locations PLn,m. Accordingly, computer 200 causes data representative of the fact that pixel values $PV216,m_V$ of vertically scaled array VA should actually be equal to pixel values $PV211,m_C$ of curvature corrected array CCA in table 280.

Since indicia 272D and 272E were expanded, portions of the image therebetween are redundant and must be eliminated. In this particular example, one row of pixel values $PVn,m_C$ must be eliminated from the curvature corrected array CCA. In generating vertical scaling correction data in table 280, computer 200 has eliminated pixel values $PV208,m_C$ of curvature corrected array CCA.

The above procedure is carried out for all pixels $PV1,m_V - PVN,m_V$ of vertically scaled array VA to generate vertical scale correction data in table 280 which characterizes the row within curvature corrected array CCA from which each row of pixel values $PVn,m_V$ of vertically scaled array VA should be taken. It has been found, however, that by vertically scaling the image in this manner, that there will be no corresponding pixels $PVn,m_C$ in curvature corrected array CCA which are properly translated to positions near the top and bottom edges of vertically scaled array VA. These portions of vertically scaled array VA, typically for rows n less than 100 and n greater than 400 for a 512 pixel array, are set equal to PVMAX so they will be represented as white in the output image. Computer 200 causes data representative of this inherent feature to be stored in table 280 of vertical scaling correction data as illustrated in FIG. 38.

To generate vertically scaled array VA, computer 200 utilizes data stored in memory and representative of table 280 (vertical scale correction data) along with pixel values $PVn,m_C$ of curvature corrected array CCA. For each pixel value $PVn,m_V$ of vertically scaled array VA, computer 200 accesses table 280 to determine from which row of curvature corrected array CCA the pixel value $PVn,m_C$ should be taken. For example, to produce a vertically scaled array VA from curvature corrected array CCA shown in FIG. 31 utilizing vertical scale correction data in table 280, pixel values $PV200,m_V$ will be set equal to corresponding pixel values $PV200,m_C$ of curvature corrected array CCA. Pixel values $PV200,200_V$ of vertically scaled array VA will, for example, be set equal to pixel value $PV200,200_C$ of curvature corrected array CCA. Following a similar approach, pixel values $PV211,m_V$ of vertically scaled array VA will be said equal to corresponding pixel values $PV205,m_C$. Pixel value $PV211,200_V$ of vertically scaled array VA will, for example, be set equal to pixel value $PV205,200_C$ of curvature corrected array CCA. Utilizing the scaling data in table 280, all pixel values $PV1,m_V$ and $PVN,m_V$ are set equal to values PVMAX. Computer 200 will then store data representative of vertically scaled array VA in RAM 202.

G. Horizontal Scaling

As previously discussed, fingerprint images produced by finger prisms 20A–20D will have horizontal or X-axis size or scale errors due to the observation angle OA at which finger 134 of finger 132 is imaged, and the fact that portions of the fingerprint are positioned about a curved surface such as that represented by X-base curve axis 140 at sides 144 of fingerprint 143. Since the image is taken at an observation angle other than 90° with respect to the "plane" of the fingerprint at any particular point, two distances along X-axis 140 are "compressed" along the horizontal axis of the fingerprint image such as that represented by vertically scaled array VA. In other portions of the image, distances about X-axis 140 can be "expanded" from their true distance on the fingerprint.

To correct for these horizontal scale errors, computer 200 processes vertically scaled array VA in accordance with a Horizontal Scaling program to generate a horizontally scaled array HA of horizontally scaled pixel values $PVn,m_H$ as illustrated in FIG. 39. A table 310 of vertical scale correction data such as that illustrated in FIG. 40 is generated for each prism 20A–20D within system 10, and stored in either RAM 202 or ROM 204. Computer 200 utilizes the table such as 310 of horizontal scale correction data to generate horizontally scaled array HA.

The generation of a table 310 of horizontal scale correction data for prism 20A (which is representative of generation of tables of horizontal scale correction data for prisms 20A–20D) is described initially with reference to FIG. 32. As shown in FIG. 32, a template 250 has a pattern of indicia 252 which includes hatch marks 256A–256G spaced about a line 254 by known and preferably equal distances. Template 250 is then shaped to conform to groove 102 of prism 20A, and positioned within the group in such a manner that line 254 is perpendicular to a longitudinal axis of the groove. This procedure is performed in a manner identical to that previously described with reference to the Curvature Correction program. An image of pattern of indicia 252 and hatch marks 256A–256G will be propagated from image propagation surface 106, imaged by camera 28 (FIG. 2), and data representative of this image processed by computer 200 in accordance with the various programs described above until a vertically scaled array VA of the image is generated.

A portion of vertically scaled array VA representative of the image of hatch marks 256A–256E is illustrated diagrammatically in FIG. 41. Indicia 256A–256E are illustrated graphically in FIG. 41 for purposes of example. However, it is to be understood that the magnitude of the image at the particular pixel locations of indicia 256A–256E in vertically scaled array VA are actually represented by pixel values $PVn,m_V$.

Since hatch marks 256A–256E are separated by known distances on template 250, these known distances would correspond to predetermined numbers of pixel locations PLn,m in the horizontal or "m" direction of vertically scaled array VA. In the embodiment of template 250 illustrated in FIG. 32, hatch marks 256A–256G are separated by known distances. Were there are no horizontal scale error, the representation of each hatch mark 256A–256G would be separated from each other in the horizontal direction of array VA by the same predetermined number (e.g., three) pixel locations PLn,m. However, due to the scale errors inherent in prism 20A, hatch marks 256A–256G will be separated by differing numbers of pixel locations PLn,m. In the example shown in FIG. 41, hatch marks 256A and 256B are compressed, separated by no pixel locations PLn,m, and adjacent to one another. Hatch marks 256B and 256C are compressed, but not quite as much, and are separated by one pixel location PLn,m. Hatch marks 256D and 256E, on the other hand, are horizontally expanded from their normal positional relationship, and separated by four pixel locations PLn,m.

Data within table 310 characterizes locations of pixel values $PVn,m_H$ in horizontally scaled array HA as a function of the horizontal location within vertically scaled array VA at which the pixel value should be taken. With respect to FIG. 41, for example, it is assumed that pixel values $PVn,300_V$ will be correctly positioned in the same row of the horizontally scaled array HA. That is, pixel values $PVn,300,_H = PVn,300_V$. However, it is known that hatch mark 256B should be spaced from 256A by three pixel locations PLn,m in the example used above. Pixel values $PVn,301_V$ of vertically scaled array VA should therefore be positioned in column 304 of horizontally scaled array HA. Table 310, therefore, includes data which characterizes pixel values $PVn,304_H$ as being equal to pixel values $PVn,301_V$ of vertically scaled array VA.

Since hatch marks 256A and 256B were compressed due to the optical transfer properties of prism 20A, information therebetween is lost. Computer 200 thereby "fills in" this lost information by inserting or repeating pixel values $PVn,301_H - PVn,303_H$ of horizontally scaled array HA with information at one of either pixel values $PVn,300_V$ or $PVn,301_V$ of the vertically scaled array VA. In table 310, all pixel values $PVn,301_H$—$PVn,303_H$ are set equal to pixel values $PVn,301_V$ of vertically scaled array VA.

Following the above example, it is also known that hatch mark 256C should be spaced horizontally from hatch mark 256B by three pixel locations PLn,m. All pixel values $PVn,303_V$ of the 303rd column in the vertically scaled array VA should therefore actually be positioned in the 208th column of horizontally scaled array VA. Accordingly, computer 200 generates data within table 310 associating pixel values $PVn,303_V$ of vertically scaled array VA with pixel values $PVn,308_H$ of the horizontally scaled array HA. Portions of the image which were lost due to the compression between hatch marks 256B and 256C are "filled in" by repeating pixel values $PVn,302_V$ of the vertically scaled array VA at pixel values $PVn,305_H$—$PVn,307_H$ of horizontally scaled array HA. Data characteristic of this filling in or repetition of pixel values is characterized in table 310. Procedures similar to those described above are repeated for pixel values $PVn,312_H$ of horizontally scaled array HA which should actually be equal to pixel values $PVn,306_V$ of the vertically scaled array VA.

Hatch marks 256D and 256E would also be separated by three pixel locations PLn,m were no vertical scaling errors inherent in prism 20A. However, hatch marks 256D and 256E have been "expanded" by the optical properties of prism 20A, and they are actually separated by four pixel locations PLn,m. In other words, pixel values $PVn,311,_V$ in vertically scaled array VA should actually be spaced from pixel values $PVn,312_H$ of horizontally scaled array HA (which correspond to pixel values $PVn,306_V$ in vertically scaled array VA) by three pixel locations PLn,m. Accordingly, computer 200 causes data representative of the fact that pixel values $PVn,316,_H$ of horizontally scaled array HA should actually be equal to pixel values $PVn,311_V$ of vertically scaled array VA in table 310.

Since hatch marks 256D and 256E were expanded, portions of the image therebetween are redundant and must be eliminated. In this particular example, one column of pixel values $PVn,m_V$ must be eliminated from the vertically scaled array VA. In generating horizontal scale correction data in table 310, computer 200 has eliminated pixel values $PVn,308_V$ of vertically scaled array VA.

The above procedure is carried out for all pixel values $PVn,1_H$—$PVn,M_H$ of horizontally scaled array HA to generate horizontal scale correction data in table 310 which characterizes the column within vertically scaled array VA from which each column of pixel values $PVn,m_H$ of horizontally scaled array HA should be taken. It has been found, however, that by horizontally scaling the image in this manner, that there will be no corresponding pixel values $PVn,m_V$ which are properly translated to positions near the left and right edges of horizontally scaled array HA. These portions of horizontally scaled array HA, typically for columns m less than 100 and m greater than 400 for a 512 pixel array are set equal to PVMAX so that they will be represented as white in the output image. Computer 200 causes data representative of this inherent feature to be stored in table 310 of horizontal scale correction data as illustrated in FIG. 40.

To generate horizontally scaled array HA, computer 200 utilizes data stored in memory and representative of table 310 (horizontal scale correction data) along with pixel values $PVn,m_V$ of vertically scaled array VA. For each pixel value $PVn,m_H$ of horizontally scaled array HA, computer 200 accesses table 310 to determine from which column of vertically scaled array VA the pixel value $PVn,m_H$ should be taken. For example, to produce horizontally scaled array HA from vertically scaled array VA shown in FIG. 35 utilizing horizontal scale correction data in table 310, pixel values $PVn,300_H$ will be set equal to corresponding pixel values $PVn,300_V$ of vertically scaled array VA. Pixel values $PV300,300_H$ of horizontally scaled array HA will, for example, be set equal to pixel value $PV300,300_V$ of vertically scaled array VA. Following a similar approach, pixel values $PVn,311_H$ of horizontally scaled array HA will be set equal to corresponding pixel values $PVn,305_V$. Utilizing the scaling data in table 310, all pixel values $PVn,1_H$ and $PVn,M_H$ are set equal to values PVMAX. Computer 200 will then store data representative of horizontally scaled array HA and RAM 202.

H. Threshold

After the digital data representative of fingerprint 143 (FIG. 15) has been imaged by camera 28 and processed by computer 200 in accordance with the Noise Average, Illumination Equalization, Directional Filter, Unhair, Curvature Correction, and Vertical and Horizontal Scaling programs, a horizontally scaled array HA of horizontally scaled pixel values $PVn,m_H$ representative of the fingerprint image is stored in RAM 202. Each pixel value $PVn,m_H$ is an eight-bit digital value representing intensity of the image at that particular discrete or pixel location PLn,m. This data will be utilized by printer 16 to print an enhanced visual representation of the fingerprint image.

In one embodiment, printer 16 is a matrix printer capable of printing in a gray scale at discrete locations. When system 10 includes a printer 16 of this type, computer 200 retrieves pixel values $PVn,m_H$ of horizontally scaled array HA from RAM 202, maps these pixel values into a proper format, and transmits this data to the printer. Printer 16 will then print a visual representation of the fingerprint image with the intensity at each discrete printed location determined by the pixel value $PVn,m_H$.

In another embodiment, printer 16 is a dot matrix printer, and incapable of utilizing pixel values $PVn,m_H$ to print a gray scale image at discrete locations or dots. At each discrete location on applicant card 15, printer 16 can either leave the spot blank, or make it black. As a result, computer 200 implements a Threshold program to determine whether each pixel value $PVn,m_H$ of the horizontally scaled array HA should be represented as a white or black spot by printer 16 on card 15.

Implementing the Threshold program, computer 200 compares each pixel value $PVn,m_H$ to a print threshold value TP. If the pixel value $PVn,m_H$ is less than the threshold value TP, this pixel value is to represent a "black" or printed region on applicant card 15, and computer 200 accordingly sets the pixel value to zero or "0". If the pixel value $PVn,m_H$ is greater than or equal to threshold value TP, this particular pixel value is to represent a white portion of the image, and computer 200 accordingly sets a pixel value equal to one or "1". Threshold value TP can vary depending upon a desired appearance of the fingerprint image. In one embodiment, threshold value TP is a digital value representative of an intensity halfway between the two hundred and fifty-six (i.e. 128) possible intensity values which can be represented by eight-bit pixel values $PV_{n,m_H}$. If it is desired to have the black portions of the printed fingerprint image (valleys 138) to have a finer width, threshold value TP should be set to a value lower than 128. If it is desired to have the white portions of the image (ridges 136) to have a finer width, threshold value TP should be set to a level higher than 128.

Having generated a Thresholded array of enhanced pixel values $PV_{n,m_H}$, computer 200 stores these pixel values in RAM 202. In response to print signals, computer 200 will transmit these bits sequentially in a standard printer format to printer 16. In response, printer 16 will print the enhanced fingerprint image onto applicant card 15.

System Operation

Operation of fingerprinting system 10 is described with reference to FIGS. 1 and 42–47. Upon initial power-up, computer 200 will run a series of diagnostics which verify correct operation of computer 200, RAM 202, and ROM 204. After passing these diagnostics, data terminal 6 will generate a copyright notice which will be displayed on monitor 7 for several seconds. Following the copyright notice, data terminal 6 will generate and display on its monitor 8 a Main Display menu 300 illustrated in FIG. 42.

Having reviewed the available options presented on menu 300, an operator can select Option 1 by sequentially pressing the "1" and RETURN keys of keyboard 7 of data terminal 6 whenever a new booking is being processed. System 10 is then cleared of information from a previous booking, and reset so as to be ready to accept new information.

If it is desired to initiate fingerprint capture or recording, the operator can select option 2 by sequentially pressing the "2" and RETURN keys of keyboard 7. In response, data terminal 6 will generate and display Processing Choices menu 302 illustrated in FIG. 46. Having reviewed the available options presnted on menu 302, if the operator desires not to capture fingerprints, they will select Option 0 from menu 302 by sequentially pressing the "0" and RETURN keys of keyboard 7. Data terminal 8 will then redisplay Main Display menu 300. Should the operator desire to capture fingerprints, Option 1 from menu 302 will be selected by sequentially pressing the "1" and RETURN keys of keyboard 7. Option 2 from menu 302 is selected if it is desired to capture only one fingerprint. This is done if it is desired to test system capabilities, or to edit a poor previously captured print. Option 2 is selected when the operator sequentially presses the "2" and RETURN keys of keyboard 7.

If an operator desires to change capture options, Option 3 is selected by sequentially pressing the "3" and RETURN keys of keyboard 7. In response to this option, the operator will be asked a series of questions by means of prompts displayed on monitor 8 of data terminal 6. These questions are answered by pressing the "Y" key of keyboard 7 to answer "yes", or by pressing the "N" key to answer "no." Options which can be selected in this manner include a High Contrast Capture Option which allows a very quick capture of print, but with relatively low quality due to the high contrast. The operator can also get an enlarged printed copy of one of the prints if desired. If the Enlarged Print Option is selected, both a life-size and four times normal size image of a fingerprint can be printed by printer 16. Also, the operator is asked if they would like to approve the print twice. The first chance to approve the print comes after capture, and the second chance comes after the image has been visually enhanced by the image enhancement software programs. Typically, prints are approved only once, that being after processing has been completed.

When Option 1 from menu 302 is selected, system 10 enters a capture mode during which all ten individual fingerprints, plus slap prints from both the left and right hands, will be captured. This procedure is implemented with the assistance of key pad 19 and display 13 on optics/processor unit 12.

Having selected Option 1 from menu 302 when it is desired to capture fingerprints, computer 200 will first actuate motor 76 to drive slap/finger image selection optics 26 to the finger prism select position illustrated in FIG. 2 (if optics 26 is not already so positioned). Signals representative of this positioning are provided to computer 200 by microswitch 89, where upon actuation of motor 76 is terminated. Computer 200 wil then cause LED 316A of left hand indicia 312 to be lit, indicating a prompt that a fingerprint of the left thumb is to be captured. Simultaneously, computer 200 cause LEDs 21C and 21D to be lit, thereby illuminating keys 17C and 17D. The operator will then move trolley 42, using lever 52, to position a finger prism 20A–20D having the properly sized groove 102 for the thumb of the particular person being fingerprinted within aperture 51. The person being fingerprinted will then position their thumb within groove 102 of the selected prism 20A–20D, and adjust their finger within the groove while the operator observes image quality on monitor 14. When an image which it is desired to capture is displayed on monitor 14, the operator will actuate CAPTURE key 17C on key pad 19. This image is then "frozen", with digitizer 206 digitizing the data provided by TV camera 24. This data is then processed in accordance with the software programs described above to produce an array of data characterizing the enhanced fingerprint image. This data is then stored within RAM 202. If the person being fingerprinted was an amputee and did not have a left thumb, the operator would have actuated AMP key 17D. Computer 200 then stores data characteristic of this action.

If the "approve print twice" option was previously selected, the operator can further examine the image on monitor 14 prior to its being processed. If this option was selected, computer 200 will cause LEDs 21A and 21B to be lit, illuminating keys 17A and 17B to indicate that one of these keys is the correct response. If it is desired to continue processing this image, YES key 17A is actuated. If after further study, it is decided that this image is not acceptable, NO key 17B is actuated.

After the capture and processing of the left thumb fingerprint, computer 200 will cause LED 316B to be illuminated thereby prompting the operator that the left index finger is to be fingerprinted. The above described procedures are then repeated, with prompts for each of the ten fingers of the two hands of the person being fingerprinted being made.

After all ten fingers have been individually fingerprinted in the above-described manner, a prompt will be displayed on monitor 8 of data terminal 6 indicating that slap or plain prints for the left hand are to be taken. Computer 200 will also actuate motor 76 so as to drive mounting plate 60 to its slap print image selection position. Computer 200 will receive a signal from microswitch 87, and deactivate motor 76, when selection optics 26 are properly positioned at the slap image position illustrated in FIG. 3B. CAPTURE key 17C and AMP key 17D will also be lit. The person to be fingerprinted will then position the index, middle, ring and little fingers of the left hand on finger receving surface 150 of slap print prism 18'. When the operator observes a high quality image on monitor 14, they will press CAPTURE key 17C which "freezes" this image, and causes it to be processed by the image enhancement software of processor subsystem 30. Data representative of this slap print image is then stored in RAM 202. This procedure is then repeated for the slap or plain prints of the right hand.

After the slap prints have been taken, Main Display menu 300 which is shown in FIG. 42 will again be displayed on monitor 8 of data terminal 6. The operator can then select Option 3 to enter demographic information regarding the person whose fingerprints have just been taken as well as to enter department information used by the police or other organization performing the fingerprinting. When Option 3 is selected, data terminal 6 will display on its monitor 8 a Demographic/Department Information menu such as 320 (FIG. 45) which requests the operator to enter all necessary demographic and department information. The operator can then enter this demographic information using the various keys of keyboard 7 of data terminal 6 in a standard manner. Main Display menu 300 can then again be displayed when the operator presses the RETURN key once all demographic and department information has been entered into terminal 6.

After all fingerprints have been captured and demographic/department information entered, the operator can select Option 4 to have all of this information printed on a standardized booking or applicant card such as 15 illustrated in FIG. 47. Applicant card 15 has standardized locations for all the various fingerprints which have been capured, as well as the demographic information and department information which has been entered into terminal 6. Card 15 will be inserted into printer 16 in an indexed manner. When Option 4 is selected, computer 200 causes all of the information retrieved from RAM 202 and to be printed at the proper locations on card 15.

Conclusion

In conclusion, the optical fingerprinting system of the present invention offers a number of significant advantages over those of the prior art. Both individual fingerprint and slap print images can be optically obtained. A real-time display of the fingerprint being imaged can be observed and analyzed prior to its capture. Grooves within the finger prisms are contoured in such a manner as to provide an optimum amount of contact between the fingerprint and the prism. The lens trolley, which has finger prisms with a variety of different sized grooves, permits use of the system with a wide range of finger sizes. The lensed surface of the finger and slap prisms reduces vertical and horizontal scale errors, as well as curvature correction errors. Furthermore, remaining scale and curvature errors are eliminated, and other characteristics of the fingerprint image greatly enhanced, through the use of the Image Enhancement programs. The system is also designed to be very user friendly.

Although the present invention has been described with reference to preferred embodiments, workers skilled in the art will recognize that changes may be made in form and detail without departing from the spirit and scope of the invention.

```
                       Average - Aver   pixel with neighbors

Address Object        Statement xdef    Average 00000001              section 1 include macros.def        include macro definitions
         00000001              NOLIST
                               NOLIST include global.def        include global symbol definitions
                        ##     Global.def - global symbol definitions
                        #
                        #      Copyright (C) 1986, CFA Technologies, Inc.

Intensity level definitions.

00000000       L0     equ     0
         00000010       L1     equ     16
         00000020       L2     equ     32
         00000030       L3     equ     48
         00000040       L4     equ     64
```

```
Address Object    Statement.
00000050         L5       equ   80
00000060         L6       equ   96
00000070         L7       equ   112
00000080         L8       equ   128
00000090         L9       equ   144
000000A0         L10      equ   160
000000B0         L11      equ   176
000000C0         L12      equ   192
000000D0         L13      equ   208
000000E0         L14      equ   224
000000FF         L15      equ   255

****    Useful constants.

00000009         Yshift   equ   9                ; log 2 of X and Y coordinate bounds
000001FF         Border   equ   (1<<Yshift)-1    ; X and Y coordinate border

****    Character constants.

00000020         Space    equ   $20
00000007         Bel      equ   'G'-$40
00000008         BS       equ   'H'-$40
00000009         Tab      equ   'I'-$40
0000000A         LF       equ   'J'-$40
0000000C         FF       equ   'L'-$40
0000000D         CR       equ   'M'-$40
0000000E         SO       equ   'N'-$40
0000000F         SI       equ   'O'-$40
00000011         Xon      equ   'Q'-$40
00000013         Xoff     equ   'S'-$40
0000001B         Esc      equ   '['-$40
0000007F         Del      equ   $7f
00000019         CtrlY    equ   'Y'-$40

****    Constants used to control LEDs

* Legal codes for ButtonLight (SwitchOff also good for FingerLight)

00000000         SwitchOff    equ   0
00000001         YesAndNo     equ   1
00000002         Capture      equ   2
00000003         SwitchTest   equ   3

* Codes to control fluorescent lights

00000001         FluorRoll    equ   1
00000002         FluorSlap    equ   2

****    Assembly constants.

**      Background fill value.
```

| Address | Object | Statement | | | |
|---|---|---|---|---|---|
| | 000000FF | BackFill | equ | L15 | white |

```
**      Assembly options.

FFFFFFFF      StandardAverage equ    true      use (1,2,1) (2,4,2) (1,2,1) average
      00000000      HorizAverage    equ    false     use (0,0,0) (1,2,1) (0,0,0) average

****

***     Average - Average pixel with neighbors.
      *       Original version by M. S. Ransom.
      *       Implemented in 68000 assembly language and
      *       modified to run without buffers by D. E. Germann.
      *
      *       entry   (a1.l) = address of input image screen buffer
      *               NOTE: There MUST be free memory of size 2*(Border+1)
      *                     bytes before the input screen image.
      *
      *       exit    (a1.l) = address of averaged image.
      *
      *       uses    a - l
      *               d - none.
      *
      *       calls   none.

Average
1 000000 48E7F038                  movem.l  a2-a4/d0-d3,-(sp)    save registers
1 000004 2449                      move.l   a1,a2
1 000006 95FC00000400              sub.l    #2*(Border+1),a2     compute address of output image
1 00000C 2649                      move.l   a1,a3
1 00000E 284A                      move.l   a2,a4                copy input and output pointers
1 000010 D7FC000001FF              add.l    #Border,a3           set up for loop entry
1 000016 D9FC000001FF              add.l    #Border,a4
1 00001C 7600                      moveq    #0,d3                clear pixel register
1 00001E 323C01FD                  move.w   #Border-2,d1         y := 1 to Border-1 (d1 counts down)
1 000022 303C01FD         avg1     move.w   #Border-2,d0         x := 1 to Border-1 (d0 counts down)
1 000026 548B                      addq.l   #2,a3                point counters at next line
1 000028 548C                      addq.l   #2,a4
1 00002A 7400             avg2     moveq    #0,d2                clear sum ift       StandardAverage
                    +        IFNE      StandardAverage
1 00002C 1413                      move.b   (a3),d2              sum := 4 * pixel(x,y)
1 00002E D442                      add.w    d2,d2
1 000030 162BFFFF                  move.b   -1(a3),d3
1 000034 D443                      add.w    d3,d2                        + 2 * pixel(x-1,y)
1 000036 162B0001                  move.b   1(a3),d3
1 00003A D443                      add.w    d3,d2                        + 2 * pixel(x+1,y)
1 00003C 162BFE00                  move.b   -(Border+1)(a3),d3
1 000040 D443                      add.w    d3,d2                        + 2 * pixel(x,y-1)
1 000042 162B0200                  move.b   Border+1(a3),d3
```

```
Address Object        Statement.

1 000046 D443              add.w    d3,d2              + 2 * pixel(x,y+1)
1 000048 D442              add.w    d2,d2
1 00004A 162BFDFF          move.b   0-1-(Border+1)(a3),d3
1 00004E D443              add.w    d3,d2              + pixel(x-1,y-1)
1 000050 162BFE01          move.b   1-(Border+1)(a3),d3
1 000054 D443              add.w    d3,d2              + pixel(x+1,y-1)
1 000056 162B01FF          move.b   0-1+(Border+1)(a3),d3
1 00005A D443              add.w    d3,d2              + pixel(x-1,y+1)
1 00005C 162B0201          move.b   1+(Border+1)(a3),d3
1 000060 D443              add.w    d3,d2              + pixel(x+1,y+1)
1 000062 E84A              lsr.w    #4,d2              average := sum div 16
                           endc ift      HorizAverage
                  +        IFNE     HorizAverage
                           move.b   (a3),d2            sum := 2 * pixel(x,y)
                           add.w    d2,d2
                           move.b   -1(a3),d3
                           add.w    d3,d2              + pixel(x-1,y)
                           move.b   1(a3),d3
                           add.w    d3,d2              + pixel(x+1,y)
                           lsr.w    #2,d2              average := sum div 4
                           endc
1 000064 18C2              move.b   d2,(a4)+           store averaged pixel and advance
1 000066 528B              addq.l   #1,a3              advance to next input pixel
1 000068 51C8FFC0          dbra     d0,avg2            do next pixel
1 00006C 51C9FFB4          dbra     d1,avg1            do next raster line

**       Clear border areas that are garbage because average doesn't
                  *        operate on the whole image.

1 000070 70FF              moveq    #(BackFill<<24)+(BackFill<<16)+(BackFill<<8)+BackFill,d0
1 000072 323C007F          move.w   #((Border+1)/4)-1,d1
1 000076 224A              move.l   a2,a1
1 000078 22C0        avg3  move.l   d0,(a1)+           clear upper raster line
1 00007A 51C9FFFC          dbra     d1,avg3
1 00007E 323C007F          move.w   #((Border+1)/4)-1,d1
1 000082 224A              move.l   a2,a1
1 000084 D3FC00040000      add.l    #((Border+1)*(Border+1)),a1
1 00008A 2300        avg4  move.l   d0,-(a1)           clear lower raster line
1 00008C 51C9FFFC          dbra     d1,avg4
1 000090 224A              move.l   a2,a1
1 000092 323C01FF          move.w   #Border,d1
1 000096 1280        avg5  move.b   d0,(a1)            clear left side
1 000098 134001FF          move.b   d0,Border(a1)      clear right side
1 00009C D2FC0200          add.w    #Border+1,a1       position to next raster line
1 0000A0 51C9FFF4          dbra     d1,avg5
1 0000A4 224A              move.l   a2,a1              return output buffer address in a1
1 0000A6 4CDF1C0F          movem.l  (sp)+,a2-a4/d0-d3  restore registers and return
1 0000AA 4E75              rts
                           end 0 errors detected.
```

Equalize - perform area equalization on screen image.

| Address | Object | Statement | |
|---|---|---|---|
| | | xdef | Equalize |
| 00000001 | | section | 1 |
| | | | |
| | | include macros.def | ; include macro definitions |
| 00000001 | | NOLIST | |
| | | NOLIST | |
| | | | |
| | | include global.def | ; include global symbol definitions |
| | ;** | Global.def - global symbol definitions. | |
| | ;* | | |
| | ;* | Copyright (C) 1986, CFA Technologies, Inc. | |
| | | | |
| | ;*** | Intensity level definitions. | |
| 00000000 | L0 | equ | 0 |
| 00000010 | L1 | equ | 16 |
| 00000020 | L2 | equ | 32 |
| 00000030 | L3 | equ | 48 |
| 00000040 | L4 | equ | 64 |
| 00000050 | L5 | equ | 80 |
| 00000060 | L6 | equ | 96 |
| 00000070 | L7 | equ | 112 |
| 00000080 | L8 | equ | 128 |
| 00000090 | L9 | equ | 144 |
| 000000A0 | L10 | equ | 160 |
| 000000B0 | L11 | equ | 176 |
| 000000C0 | L12 | equ | 192 |
| 000000D0 | L13 | equ | 208 |
| 000000E0 | L14 | equ | 224 |
| 000000FF | L15 | equ | 255 |
| | | | |
| | ;*** | Useful constants. | |
| 00000009 | Yshift | equ | 9 ; log 2 of X and Y coordinate bounds |
| 000001FF | Border | equ | (1<<Yshift)-1 ; X and Y coordinate border |
| | | | |
| | ;*** | Character constants. | |
| 00000020 | Space | equ | $20 |
| 00000007 | Bel | equ | 'G'-$40 |
| 00000008 | BS | equ | 'H'-$40 |
| 00000009 | Tab | equ | 'I'-$40 |
| 0000000A | LF | equ | 'J'-$40 |
| 0000000C | FF | equ | 'L'-$40 |
| 0000000D | CR | equ | 'M'-$40 |
| 0000000E | SO | equ | 'N'-$40 |
| 0000000F | SI | equ | 'O'-$40 |

| Address Object | Statement | | | |
|---|---|---|---|---|
| 00000011 | Xon | equ | 'Q'-$40 | |
| 00000013 | Xoff | equ | 'S'-$40 | |
| 0000001B | Esc | equ | '['-$40 | |
| 0000007F | Del | equ | $7f | |
| 00000019 | CtrlY | equ | 'Y'-$40 | |

**** Constants used to control LEDs

* Legal codes for ButtonLight (SwitchOff also good for FingerLight)

| 00000000 | SwitchOff | equ | 0 |
|---|---|---|---|
| 00000001 | YesAndNo | equ | 1 |
| 00000002 | Capture | equ | 2 |
| 00000003 | SwitchTest | equ | 3 |

* Codes to control fluorescent lights

| 00000001 | FluorRoll | equ | 1 |
|---|---|---|---|
| 00000002 | FluorSlap | equ | 2 |

```
            include equalize.def      include Equalize's symbol definitions
   **       Equalize.def - Equalize's symbol definitions.
    *
```

| 00000003 | Grid | equ | 3 | size of left section of averaging grid |
|---|---|---|---|---|

**** Assembly options.

| 00000000 | LoopBackground | equ | false | use blankdist for background detection |
|---|---|---|---|---|
| FFFFFFFF | AvgBackground | equ | true | use average for background detection |

****

**** Assembly constants.

* For area equalization.

| 00000040 | TotalDots | equ | (Grid+1+(Grid+1))*(Grid+1+(Grid+1)) |
|---|---|---|---|

* For background detection using loop.

| 00000010 | BlankVal | equ | 11 | variation threshold for background |
|---|---|---|---|---|
| 00000003 | BlankDist | equ | Grid | how far to look for background |

* Background fill value for unequalized areas.

| 000000FF | BackFill | equ | 115 | white |
|---|---|---|---|---|

Address Object        Statement.

****

```
***     Equalize - perform area equalization on screen image.
*       Based on Pascal implementation by M. S. Ransom.
*       Converted to 68000 assembler by D. E. Germann.
*
*       Copyright (C) 1986, CFA Technologies, Inc.
*
*       entry    (a4.l) = input screen image address.
*                There MUST be free memory of size (Grid+1) * (Border+1)
*                before the input screen image.
*                (d0.w) = background level.
*
*       exit     image converted.
*                (a5.l) = output screen image address.
*
*       uses     a - 0, 1, 2, 3, 5, 6.
*                d - all.
*
*       calls    none.

VarBegin
00000000         +Voffset set     0
                              var.w    Background,1
FFFFFFFE         +            nolist
                              array.w  ColumnSum,0,Border,1
FFFFF8FE         +            nolist
                              VarEnd   EquRam
FFFFFBFE         +            nolist Equalize
1 000000 4E56FBFE              link     a6,#EquRam
1 000004 3D40FFFE              move.w   d0,Background(a6)      save background value
1 000008 2A4C                  move.l   a4,a5
1 00000A 9BFC00000800          sub.l    #(Grid+1)*(Border+1),a5 compute output image address
1 000010 7000                  moveq    #0,d0
1 000012 323C01FF              move.w   #Border,d1
1 000016 41EEFBFE              lea      ColumnSum(a6),a0
1 00001A 30C0          equ1    move.w   d0,(a0)+               ColumnSum[i] := 0
1 00001C 51C9FFFC              dbra     d1,equ1
1 000020 7206                  moveq    #Grid+(Grid+1)-1,d1    y := 0 (d1 counts down)
1 000022 204C                  move.l   a4,a0                  addr(ScreenIn[0,0])
1 000024 343C01FF      equ2    move.w   #Border,d2             x := 0 (d2 counts down)
1 000028 43EEFBFE              lea      ColumnSum(a6),a1
1 00002C 1018          equ3    move.b   (a0)+,d0               ScreenIn[x,y]
1 00002E D159                  add.w    d0,(a1)+               CS[x] := CS[x] + ScreenIn[x,y]
1 000030 51CAFFFA              dbra     d2,equ3
1 000034 51C9FFEE              dbra     d1,equ2
1 000038 7203                  moveq    #Grid,d1
1 00003A 7C09                  moveq    #Yshift,d6
1 00003C 7604          equ4    moveq    #Grid+1,d3
1 00003E D641                  add.w    d1,d3                  y + grid+1
```

| Address Object | | Statement | | |
|---|---|---|---|---|
| 1 000040 EDA3 | | | asl.l | d6,d3 | convert to y-coordinate |
| 1 000042 244C | | | move.l | a4,a2 | |
| 1 000044 D5C3 | | | add.l | d3,a2 | addr(ScreenIn[0,y+grid+1]) |
| 1 000046 343C01FF | | | move.w | #Border,d2 | x := 0 (d2 counts down) |
| 1 00004A 41EEFBFE | | | lea | ColumnSum(a6),a0 | |
| 1 00004E 101A | equ5 | move.b | (a2)+,d0 | ScreenIn[x,y+grid+1] |
| 1 000050 D158 | | | add.w | d0,(a0)+ | CS[x] := CS[x] + ScreenIn[x,y+grid+1] |
| 1 000052 51CAFFFA | | | dbra | d2,equ5 | |
| 1 000056 2A3C00000020 | | | move.l | #TotalDots/2,d5 | sum := TotalDots div 2 (0.5 to round) |
| 1 00005C 7606 | | | moveq | #Grid+(Grid+1)-1,d3 | i := 0 (d2 counts down) |
| 1 00005E 45EEFBFE | | | lea | ColumnSum(a6),a2 | |
| 1 000062 DA5A | equ6 | add.w | (a2)+,d5 | sum := sum + ColumnSum[i] |
| 1 000064 51CBFFFC | | | dbra | d3,equ6 | |
| 1 000068 45EEFC04 | | | lea | ColumnSum+(Grid*2)(a6),a2 | addr(ColumnSum[Grid]) |
| 1 00006C 2601 | | | move.l | d1,d3 | |
| 1 00006E EDA3 | | | asl.l | d6,d3 | |
| 1 000070 5683 | | | addq.l | #Grid,d3 | |
| 1 000072 224C | | | move.l | a4,a1 | |
| 1 000074 D3C3 | | | add.l | d3,a1 | addr(ScreenIn[Grid,Y]) |
| 1 000076 2640 | | | move.l | a5,a3 | |
| 1 000078 D7C3 | | | add.l | d3,a3 | addr(ScreenOut[Grid,y]) |
| 1 00007A 7403 | | | moveq | #Grid,d2 | x := grid |
| 1 00007C DA6A0008 | equ7 | add.w | 2*(Grid+1)(a2),d5 | sum := sum + ColumnSum[X+grid+1] |
| 1 000080 1011 | | | move.b | (a1),d0 | pixel := ScreenIn[x,y] |
| | | ifne | LoopBackground | | |
| | | moveq | #1,d3 | i := 1 (offset for x) |
| | | move.w | #1<<Yshift,d4 | (offset for y) |
| | equ8 | neg.w | d4 | |
| | | moveq | #0,d7 | |
| | | move.b | 0(a1,d4.w),d7 | ScreenIn[x,y-1] |
| | | sub.w | d0,d7 | pixel - ScreenIn[x,y-1] |
| | | bge.s | equ9 | |
| | | neg.w | d7 | abs(pixel - ScreenIn[x,y-1]) |
| | equ9 | cmp.w | #BlankVal,d7 | |
| | | bgt.s | equ13 | if abs() > BlankVal |
| | | neg.w | d4 | |
| | | moveq | #0,d7 | |
| | | move.b | 0(a1,d4.w),d7 | ScreenIn[x,y+1] |
| | | sub.w | d0,d7 | pixel - ScreenIn[x,y+1] |
| | | bge.s | equ10 | |
| | | neg.w | d7 | abs(pixel - ScreenIn[x,y+1]) |
| | equ10 | cmp.w | #BlankVal,d7 | |
| | | bgt.s | equ13 | if abs() > BlankVal |
| | | neg.w | d3 | |
| | | moveq | #0,d7 | |
| | | move.b | 0(a1,d3.w),d7 | ScreenIn[x-i,y] |
| | | sub.w | d0,d7 | pixel - ScreenIn[x-i,y] |
| | | bge.s | equ11 | |
| | | neg.w | d7 | abs(pixel - ScreenIn[x-i,y]) |
| | equ11 | cmp.w | #BlankVal,d7 | |
| | | bgt.s | equ13 | if abs() > BlankVal |
| | | neg.w | d3 | |
| | | moveq | #0,d7 | |
| | | move.b | 0(a1,d3.w),d7 | ScreenIn[x+i,y] |

| Address Object | Statement | | |
|---|---|---|---|
| | | sub.w | d0,d7 | pixel - ScreenIn[x+i,y] |
| | | bge.s | equ12 |
| | | neg.w | d7 | abs(pixel - ScreenIn[x+i,y]) |
| | equ12 | cmp.w | #BlankVal,d7 |
| | | bgt.s | equ13 | if abs() > BlankVal |
| | | addq.w | #1,d3 | i := i + 1 (offset for x) |
| | | add.w | #1<<Yshift,d4 | (offset for y) |
| | | cmp.w | #BlankDist,d3 |
| | | ble | equ8 | if i <= BlankDist |
| | | moveq | #0,d3 | BlankFlag := true |
| | | endc |

| 1 000082 7EFF | equ13 | moveq | #L15,d7 | preload background for blank areas |

| | | ifne | LoopBackground |
| | | tst.b | d3 |
| | | beq.s | equ14 | if BlankFlag |
| | | endc |

| 1 000084 2805 | | move.l | d5,d4 |

| | | ifeq | TotalDots-64 |
| 1 000086 EC4C | | lsr.w | #6,d4 | average := sum div TotalDots |
| | | endc |

| | | ifne | TotalDots-64 |
| | | ifeq | TotalDots-256 |
| | | lsr.w | #8,d4 | average := sum div TotalDots |
| | | endc |

| | | ifne | TotalDots-256 |
| | | divu | #TotalDots,d4 | average := sum div TotalDots |
| | | endc |
| | | endc |

| | | ifne | AvgBackground |
| 1 000088 B86EFFFE | | cmp.w | Background(a6),d4 |
| 1 00008C 6E16 | | bgt.s | equ14 | if average value is background |
| | | endc |

| 1 00008E 3600 | | move.w | d0,d3 |
| 1 000090 9644 | | sub.w | d4,d3 |
| 1 000092 D67C0080 | | add.w | #L8,d3 | pixel := pixel - average + L8 |
| 1 000096 B67C00FF | | cmp.w | #L15,d3 |
| 1 00009A 6E08 | | bgt.s | equ14 | if pixel > L15 then pixel := L15 |
| 1 00009C 7E00 | | moveq | #L0,d7 | preload L0 in case pixel < L0 |

| | | ifeq | L0 |
| 1 00009E 4A43 | | tst.w | d3 |
| | | endc |

| | | ifne | L0 |
| | | cmp.w | #L0,d3 |
| | | endc |

```
Address Object         Statement.
1 0000A0 6D02                blt.s    equ14              if pixel < L0 then pixel := L0
1 0000A2 3E03                move.w   d3,d7              output pixel is OK as it is
1 0000A4 16C7        equ14   move.b   d7,(a3)+           store output pixel
1 0000A6 9A6AFFFA            sub.w    -2%Grid(a2),d5     sum := sum - ColumnSum[x-grid]
1 0000AA 548A                addq.l   #2,a2              advance ColumnSum pointer
1 0000AC 5289                addq.l   #1,a1              advance screen pointer
1 0000AE 5242                addq.w   #1,d2              x := x + 1
1 0000B0 B47C01FB            cmp.w    #Border-(Grid+1),d2
1 0000B4 6FC6                ble      equ7               do next x value
1 0000B6 76FD                moveq    #-Grid,d3
1 0000B8 D681                add.l    d1,d3              y-grid
1 0000BA EDA3                asl.l    d6,d3
1 0000BC 224C                move.l   a4,a1
1 0000BE D3C3                add.l    d3,a1              addr(ScreenIn[0,y-grid])
1 0000C0 45EEFBFE            lea      ColumnSum(a6),a2
1 0000C4 343C01FF            move.w   #Border,d2         x := 0 (d2 counts down)
1 0000C8 1019        equ19   move.b   (a1)+,d0
1 0000CA 915A                sub.w    d0,(a2)+           CS[x] := CS[x] - ScreenIn[x,y-grid]
1 0000CC 51CAFFFA            dbra     d2,equ19
1 0000D0 5241                addq.w   #1,d1              y := y + 1
1 0000D2 B27C01FB            cmp.w    #Border-(Grid+1),d1
1 0000D6 6F00FF64            ble      equ4               do next y value

**      -Clear border areas that are garbage because Equalize doesn't
                     *        operate on the whole image.

1 0000DA 203CFFFFFFFF equ20  move.l   #(BackFill<<24)+(BackFill<<16)+(BackFill<<8)+BackFill,d0
1 0000E0 323C017F            move.w   #(((Border+1)/4)%(Grid))-1,d1
1 0000E4 224D                move.l   a5,a1
1 0000E6 22C0        equ21   move.l   d0,(a1)+           clear upper raster lines
1 0000E8 51C9FFFC            dbra     d1,equ21
1 0000EC 323C01FF            move.w   #(((Border+1)/4)%(Grid+1))-1,d1
1 0000F0 224D                move.l   a5,a1
1 0000F2 D3FC00040000        add.l    #((Border+1)%(Border+1)),a1
1 0000F8 2300        equ22   move.l   d0,-(a1)           clear lower raster lines
1 0000FA 51C9FFFC            dbra     d1,equ22
1 0000FE 224D                move.l   a5,a1
1 000100 323C01FF            move.w   #Border,d1
1 000104 7802        equ23   moveq    #Grid-1,d4
1 000106 13804000    equ24   move.b   d0,0(a1,d4.w)      clear this line's left side
1 00010A 51CCFFFA            dbra     d4,equ24
1 00010E D2FC0200            add.w    #Border+1,a1       position to next raster line
1 000112 7803                moveq    #Grid,d4
1 000114 7AFF                moveq    #-1,d5
1 000116 13805000    equ25   move.b   d0,0(a1,d5.w)      clear previous line's right side
1 00011A 5345                subq.w   #1,d5
1 00011C 51CCFFF8            dbra     d4,equ25
1 000120 51C9FFE2            dbra     d1,equ23
1 000124 4E5E                unlk     a6
1 000126 4E75                rts end
```

DirectionalFilter - Directional average.

Address Object       Statement xdef    DirectionalFilter 00000001             section 1 include macros.def        include macro definitions
00000001             NOLIST
                     NOLIST include global.def        include global symbol definitions
             ;*      Global.def - global symbol definitions.
             ;
             ;       Copyright (C) 1986, CFA Technologies, Inc.

;***    Intensity level definitions.

00000000             L0      equ     0
00000010             L1      equ     16
00000020             L2      equ     32
00000030             L3      equ     48
00000040             L4      equ     64
00000050             L5      equ     80
00000060             L6      equ     96
00000070             L7      equ     112
00000080             L8      equ     128
00000090             L9      equ     144
000000A0             L10     equ     160
000000B0             L11     equ     176
000000C0             L12     equ     192
000000D0             L13     equ     208
000000E0             L14     equ     224
000000FF             L15     equ     255

;***    Useful constants.

00000009             Yshift  equ     9                ; log 2 of X and Y coordinate bounds
000001FF             Border  equ     (1<<Yshift)-1    ; X and Y coordinate border ;***    Character constants.

00000020             Space   equ     $20
00000007             Bel     equ     'G'-$40
00000008             BS      equ     'H'-$40
00000009             Tab     equ     'I'-$40
0000000A             LF      equ     'J'-$40
0000000C             FF      equ     'L'-$40
0000000D             CR      equ     'M'-$40
0000000E             SO      equ     'N'-$40
0000000F             SI      equ     'O'-$40
00000011             Xon     equ     'Q'-$40

| Address | Object | Statement | | |
|---|---|---|---|---|
| | 00000013 | Xoff | equ | 'S'-$40 |
| | 0000001B | Esc | equ | '['-$40 |
| | 0000007F | Del | equ | $7f |
| | 00000019 | CtrlY | equ | 'Y'-$40 |

**** Constants used to control LEDs

* Legal codes for ButtonLight (SwitchOff also good for FingerLight)

| | | | | |
|---|---|---|---|---|
| 00000000 | SwitchOff | equ | 0 | |
| 00000001 | YesAndNo | equ | 1 | |
| 00000002 | Capture | equ | 2 | |
| 00000003 | SwitchTest | equ | 3 | |

* Codes to control fluorescent lights

| | | | | |
|---|---|---|---|---|
| 00000001 | FluorRoll | equ | 1 | |
| 00000002 | FluorSlap | equ | 2 | |

**** Assembly constants.

** Tunable parameters.

| | | | | |
|---|---|---|---|---|
| 00000005 | XGridLog | equ | 5 | log2(slope x-grid size) |
| 00000004 | YGridLog | equ | 4 | log2(slope y-grid size) |
| 00000001 | Step | equ | 1 | step distance when determining slopes |
| 000000FF | BackFill | equ | L15 | background fill value (white) |

** - Derived constants.

| | | | | |
|---|---|---|---|---|
| 00000020 | XGridSize | equ | 1<<XGridLog | size of x-grid to determine line slopes |
| 00000010 | YGridSize | equ | 1<<YGridLog | size of y-grid to determine line slopes |
| 00000010 | XOffset | equ | XGridSize/2 | x-displacement for offset slope grid |
| 00000008 | YOffset | equ | YGridSize/2 | y-displacement for offset slope grid |
| 0000000F | LastXGrid | equ | Border/XGridsize | index of last slope x-grid |
| 0000001F | LastYGrid | equ | Border/YGridsize | index of last slope y-grid |

****

```
**   DirectionalFilter - Directional average to bitmap.
*    Based on Pascal design by M. S. Ransom.
*    Implemented in 68000 assembler and modified to run
*    without buffers by D. E. Germann.
*
```

| Address | Object | | Statement | |
|---|---|---|---|---|
| | | ‡ | entry | (a1.1) = address of input image screen buffer. |
| | | ‡ | | NOTE: there must be 2*(Border+1) bytes of free memory |
| | | ‡ | | in front of the input image screen buffer. |
| | | ‡ | | |
| | | ‡ | exit | (a1.1) = address of output image screen buffer. |
| | | ‡ | | |
| | | ‡ | uses | a - 1. |
| | | ‡ | | d - none. |
| | | ‡ | | |
| | | ‡ | calls | none. |

```
                          VarBegin
00000000        +Voffset  set       0
                          Var.1     ScreenOut,1
FFFFFFFC        +         nolist
                          Array2.l  GridTotal,-1,LastYGrid,-1,LastXGrid,4
FFFFDE0C        +         nolist
                          Array2.l  OffTotal,-1,LastYGrid,-1,LastXGrid,4
FFFFBAFC        +         nolist
                          Array2.b  Slopes,-1,LastYGrid,-1,LastXGrid,1
FFFFB78D        +         nolist
                          Array2.b  OffSlopes,-1,LastYGrid,-1,LastXGrid,1
FFFFB58C        +         nolist
                          VarEnd    DirRam
FFFFB57A        +         nolist DirectionalFilter
1 000000 4E56B57A         link      a6,#DirRam
1 000004 48E7FFBC         movem.l   a0/a2-a5/d0-d7,-(sp)     save registers
1 000008 2049             move.l    a1,a0                    save input image address for later
1 00000A 2449             move.l    a1,a2
1 00000C 94FC0400       - sub.w     #2*(Border+1),a2         compute address of output image
1 000010 2D4AFFFC         move.l    a2,ScreenOut(a6)         save output image address ‡         Initialize.

1 000014 7000             moveq     #0,d0
1 000016 323C08C3         move.w    #((1+1+LastYGrid)*(1+1+LastXGrid)*4)-1,d1   longwords to clear
1 00001A 3401             move.w    d1,d2
1 00001C 43EEDCEC         lea       GridTotal-(1*(1+1+LastXGrid)*(4*4))-(4*4)(a6),a1
1 000020 22C0         dir2 move.l   d0,(a1)+                 GridTotal[*,*,*] := 0
1 000022 51C9FFFC         dbra      d1,dir2
1 000026 43EEB9DC         lea       OffTotal-(1*(1+1+LastXGrid)*(4*4))-(4*4)(a6),a1
1 00002A 22C0         dir3 move.l   d0,(a1)+                 OffTotal[*,*,*] := 0
1 00002C 51CAFFFC         dbra      d2,dir3

‡         Compute grid directional sums.

1 000030 7800             moveq     #0,d4                    clear pixel register
1 000032 7401             moveq     #1,d2                    y := 1
1 000034 2E02         dir4 move.l   d2,d7
```

```
Address Object      Statement.
1 000036 E847                asr.w    #YGridLog,d7            GridY := y div YGridSize ifeq     LastXGrid-15
1 000038 3607                move.w   d7,d3
1 00003A E947                asl.w    #4,d7                   * 16
1 00003C DE43                add.w    d3,d7                   GridY * (1 + 1 + LastXGrid)
                             endc ifne     LastXGrid-15
                             muls     #(1+1+LastXGrid),d7     GridY * (1 + 1 + LastXGrid)
                             endc 1 00003E E987                asl.l    #2+2,d7                 [GridY, 0]
1 000040 47EEDE0C            lea      GridTotal(a6),a3
1 000044 D7C7                add.l    d7,a3                   addr(GridTotal[GridY, 0])
1 000046 7EF8                moveq    #-YOffset,d7
1 000048 DE82                add.l    d2,d7                   y - Yoffset
1 00004A E847                asr.w    #YGridLog,d7            GridY2 := (y - YOffset) div YGridSize ifeq     LastXGrid-15
1 00004C 3607                move.w   d7,d3
1 00004E E947                asl.w    #4,d7                   * 16
1 000050 DE43                add.w    d3,d7                   GridY2 * (1 + 1 + LastXGrid)
                             endc ifne     LastXGrid-15
                             muls     #(1+1+LastXGrid),d7     GridY2 * (1 + 1 + LastXGrid)
                             endc 1 000052 E987                asl.l    #2+2,d7                 [GridY2, 0]
1 000054 49EEBAFC            lea      OffTotal(a6),a4
1 000058 D9C7                add.l    d7,a4                   addr(OffTotal[GridY2, 0])
1 00005A 98FC0010            sub.w    #4*4,a4                 addr(OffTotal[GridY2, -1])
1 00005E 7E09                moveq    #Yshift,d7
1 000060 2602                move.l   d2,d3
1 000062 EFA3                asl.l    d7,d3                   convert y to coordinate offset
1 000064 2A48                move.l   a0,a5
1 000066 DBC3                add.l    d3,a5                   addr(ScreenIn[0, y])
1 000068 7200                moveq    #0,d1                   x := 0
1 00006A 7C20                moveq    #XGridSize,d6           grid counter for GridTotal
1 00006C 7E10                moveq    #XGridSize/2,d7         grid counter for OffTotal
1 00006E 1015       dir5     move.b   (a5),d0                 pixel := ScreenIn[x, y]
1 000070 182D0001            move.b   1(a5),d4                dot := ScreenIn[x+1, y]
1 000074 9840                sub.w    d0,d4                   dot - pixel
1 000076 6C02                bge.s    dir6
1 000078 4444                neg.w    d4                      abs(dot - pixel)
1 00007A D99B       dir6     add.l    d4,(a3)+                add to horizontal sum
1 00007C D99C                add.l    d4,(a4)+
1 00007E 182D0201            move.b   1+(Border+1)(a5),d4     dot := ScreenIn[x+1, y+1];
1 000082 9840                sub.w    d0,d4                   dot - pixel
1 000084 6C02                bge.s    dir7
1 000086 4444                neg.w    d4                      abs(dot - pixel)
1 000088 D99B       dir7     add.l    d4,(a3)+                add to positive slope sum
```

| Address Object | | Statement. | | |
|---|---|---|---|---|
| 1 00008A D99C | | | add.l | d4,(a4)+ |
| 1 00008C 182D0200 | | | move.b | Border+1(a5),d4 | dot := ScreenIn[x, y+1]
| 1 000090 9840 | | | sub.w | d0,d4 | dot - pixel
| 1 000092 6C02 | | | bge.s | dir8 |
| 1 000094 4444 | | | neg.w | d4 | abs(dot - pixel)
| 1 000096 D99B | | dir8 | add.l | d4,(a3)+ | add to vertical sum
| 1 000098 D99C | | | add.l | d4,(a4)+ |
| 1 00009A 182DFE01 | | | move.b | 1-(Border+1)(a5),d4 | dot := ScreenIn[x+1, y-1]
| 1 00009E 9840 | | | sub.w | d0,d4 | dot - pixel
| 1 0000A0 6C000004 | | | bge | dir9 |
| 1 0000A4 4444 | | | neg.w | d4 | abs(dot - pixel)
| 1 0000A6 D993 | | dir9 | add.l | d4,(a3) | add to negative slope sum
| 1 0000A8 D994 | | | add.l | d4,(a4) |
| 1 0000AA 96FC000C | | | sub.w | #3*4,a3 | go back to start of array
| 1 0000AE 98FC000C | | | sub.w | #3*4,a4 |
| 1 0000B2 5241 | | | addq.w | #Step,d1 | x := x + Step
| 1 0000B4 5280 | | | addq.l | #Step,a5 | advance screen pointer
| 1 0000B6 5346 | | | subq.w | #Step,d6 | GTcounter := GTcounter - Step
| 1 0000B8 6E08 | | | bgt.s | dir9.1 | if more pixels in this grid
| 1 0000BA D6FC0010 | | | add.w | #4*4,a3 | go to next array entry
| 1 0000BE DC7C0020 | | | add.w | #XGridSize,d6 | update GTcounter
| 1 0000C2 5347 | | dir9.1 | subq.w | #Step,d7 | OTcounter := OTcounter - Step
| 1 0000C4 6E08 | | | bgt.s | dir9.2 | if more pixels in this grid
| 1 0000C6 D8FC0010 | | | add.w | #4*4,a4 | go to next array entry
| 1 0000CA DE7C0020 | | | add.w | #XGridSize,d7 | update OTcounter
| 1 0000CE B27C01FE | | dir9.2 | cmp.w | #Border-1,d1 |
| 1 0000D2 6F9A | | | ble | dir5 | if x <= (Border - 1)
| 1 0000D4 5242 | | dir10 | addq.w | #Step,d2 | y := y + Step
| 1 0000D6 B47C01FE | | | cmp.w | #Border-1,d2 |
| 1 0000DA 6F00FF58 | | | ble | dir4 | if y <= (Border - 1)

\*    Determine line slopes.

| 1 0000DE 43EEDCEC | | dir11 | lea | GridTotal-(1*(1+1+LastXGrid)*(4*4))-(1*(4*4))(a6),a1 | GT[-1,-1]
| 1 0000E2 45EEB9DC | | | lea | OffTotal-(1*(1+1+LastXGrid)*(4*4))-(1*(4*4))(a6),a2 | OT[-1,-1]
| 1 0000E6 47EEB7AB | | | lea | Slopes-(1*(1+1+LastXGrid))-1(a6),a3 | Slopes[-1,-1]
| 1 0000EA 49EEB57A | | | lea | OffSlopes-(1*(1+1+LastXGrid))-1(a6),a4 | OffSlopes[-1,-1]
| 1 0000EE 7420 | | | moveq | #LastYGrid+1+1-1,d2 | y := -1 to LastYGrid (d2 counts down)
| 1 0000F0 7210 | | dir12 | moveq | #LastXGrid+1+1-1,d1 | x := -1 to LastXGrid (d1 counts down)
| 1 0000F2 2E19 | | dir13 | move.l | (a1)+,d3 | min := GridTotal[y, x, Horizontal]
| 1 0000F4 7800 | | | moveq | #0*4,d4 | mindir := Horizontal
| 1 0000F6 2E19 | | | move.l | (a1)+,d7 | next := GridTotal[y, x, PositiveSlope]
| 1 0000F8 BE83 | | | cmp.l | d3,d7 |
| 1 0000FA 6C04 | | | bge.s | dir14 | if next >= min
| 1 0000FC 2607 | | | move.l | d7,d3 | min := next
| 1 0000FE 7804 | | | moveq | #1*4,d4 | mindir := PositiveSlope
| 1 000100 2E19 | | dir14 | move.l | (a1)+,d7 | next := GridTotal[y, x, Vertical]
| 1 000102 BE83 | | | cmp.l | d3,d7 |
| 1 000104 6C04 | | | bge.s | dir15 | if next >= min
| 1 000106 2607 | | | move.l | d7,d3 | min := next
| 1 000108 7808 | | | moveq | #2*4,d4 | mindir := Vertical
| 1 00010A 2E19 | | dir15 | move.l | (a1)+,d7 | next := GridTotal[y, x, NegativeSlope]
| 1 00010C BE83 | | | cmp.l | d3,d7 |

```
Address Object         Statement.
1 00010E 6C02              bge.s   dir16              if next >= min
1 000110 780C              moveq   #3*4,d4            mindir := NegativeSlope
1 000112 16C4      dir16   move.b  d4,(a3)+           Slopes[y, x] := mindir
1 000114 261A              move.l  (a2)+,d3           min := OffTotal[y, x, Horizontal]
1 000116 7800              moveq   #0*4,d4            mindir := Horizontal
1 000118 2E1A              move.l  (a2)+,d7           next := OffTotal[y, x, PositiveSlope]
1 00011A BE83              cmp.l   d3,d7
1 00011C 6C04              bge.s   dir17              if next >= min
1 00011E 2607              move.l  d7,d3              min := next
1 000120 7804              moveq   #1*4,d4            mindir := PositiveSlope
1 000122 2E1A      dir17   move.l  (a2)+,d7           next := OffTotal[y, x, Vertical]
1 000124 BE83              cmp.l   d3,d7
1 000126 6C04              bge.s   dir18              if next >= min
1 000128 2607              move.l  d7,d3              min := next
1 00012A 7808              moveq   #2*4,d4            mindir := Vertical
1 00012C 2E1A      dir18   move.l  (a2)+,d7           next := OffTotal[y, x, NegativeSlope]
1 00012E BE83              cmp.l   d3,d7
1 000130 6C02              bge.s   dir19              if next >= min
1 000132 780C              moveq   #3*4,d4            mindir := NegativeSlope
1 000134 18C4      dir19   move.b  d4,(a4)+           OffSlopes[y, x] := mindir
1 000136 51C9FFBA          dbra    d1,dir13           do next x
1 00013A 51CAFFB4          dbra    d2,dir12           do next y

*       Average image.

1 00013E 226EFFFC          move.l  ScreenOut(a6),a1
1 000142 D1FC000001FF      add.l   #Border,a0         set up for loop entry
1 000148 D3FC000001FF      add.l   #Border,a1
1 00014E 7400              moveq   #0,d2              clear pixel register
1 000150 7201              moveq   #1,d1              y := 1
1 000152 2801      dir20   move.l  d1,d4
1 000154 E844              asr.w   #YGridLog,d4       GridY := y div YGridSize ifeq    LastXGrid-15
1 000156 3A04              move.w  d4,d5
1 000158 E944              asl.w   #4,d4              * 16
1 00015A D845              add.w   d5,d4              GridY * (1+1+LastXGrid) { [GridY, 0] }
                           endc ifne    LastXGrid-15
                           muls    #(1+1+LastXGrid),d4  GridY * (1+1+LastXGrid) { [GridY, 0] }
                           endc 1 00015C 45EEB7B0          lea     Slopes(a6),a2
1 000160 D5C4              add.l   d4,a2              addr(Slopes[GridY, 0])
1 000162 78F8              moveq   #-YOffset,d4
1 000164 D881              add.l   d1,d4              y - Yoffset
1 000166 E844              asr.w   #YGridLog,d4       GridY2 := (y - Yoffset) div YGridSize ifeq    LastXGrid-15
1 000168 3A04              move.w  d4,d5
1 00016A E944              asl.w   #4,d4              * 16
1 00016C D845              add.w   d5,d4              GridY2 * (1+1+LastXGrid) { [GridY2, 0] }
```

| Address | Object | Statement | | |
|---|---|---|---|---|
| | | | endc | |
| | | | ifne | LastXGrid-15 |
| | | | muls | #(LastXGrid+1+1),d4 | GridY2 * (1+1+LastXGrid) ( [GridY2 0] ) |
| | | | endc | |
| 1 00016E | 47EEB58C | | lea | OffSlopes(a6),a3 | |
| 1 000172 | 07C4 | | add.l | d4,a3 | addr(OffSlopes[GridY2, 0]) |
| 1 000174 | 534B | | subq.w | #1,a3 | addr(OffSlopes[GridY2, -1]) |
| 1 000176 | 7001 | | moveq | #1,d0 | x := 1 |
| 1 000178 | 5488 | | addq.l | #2,a0 | point input screen pointer at next line |
| 1 00017A | 5489 | | addq.l | #2,a1 | point output screen pointer at next line |
| 1 00017C | 4BFA006A | | lea | SideComp(pc),a5 | |
| 1 000180 | 7E00 | | moveq | #0,d7 | |
| 1 000182 | 1E1A | | move.b | (a2)+,d7 | main grid slope for this grid |
| 1 000184 | 2C357000 | | move.l | 0(a5,d7.w),d6 | main grid component offsets |
| 1 000188 | 7820 | | moveq | #XGridSize,d4 | grid counter for GridSlopes |
| 1 00018A | 1E1B | | move.b | (a3)+,d7 | offset grid slope for this grid |
| 1 00018C | 2E357000 | | move.l | 0(a5,d7.w),d7 | offset grid component offsets |
| 1 000190 | 7A10 | | moveq | #XGridSize/2,d5 | grid counter for OffSlopes |
| 1 000192 | B743 | dir21 | eor.w | d3,d3 | sum := 0 |
| 1 000194 | 1618 | | move.b | (a0)+,d3 | |
| 1 000196 | D643 | | add.w | d3,d3 | |
| 1 000198 | D643 | | add.w | d3,d3 | sum := Screen[x, y] * 4 |
| 1 00019A | 143060FF | | move.b | -1(a0,d6.w),d2 | |
| 1 00019E | D642 | | add.w | d2,d3 | add side one |
| 1 0001A0 | 4846 | | swap | d6 | |
| 1 0001A2 | 143060FF | | move.b | -1(a0,d6.w),d2 | |
| 1 0001A6 | D642 | | add.w | d2,d3 | add side two |
| 1 0001A8 | 143070FF | | move.b | -1(a0,d7.w),d2 | |
| 1 0001AC | D642 | | add.w | d2,d3 | add side one |
| 1 0001AE | 4847 | | swap | d7 | |
| 1 0001B0 | 143070FF | | move.b | -1(a0,d7.w),d2 | |
| 1 0001B4 | D642 | | add.w | d2,d3 | add side two |
| 1 0001B6 | 5843 | | addq.w | #8/2,d3 | add in rounding factor |
| 1 0001B8 | E64B | | lsr.w | #3,d3 | average := round(sum / 8) |
| 1 0001BA | 12C3 | | move.b | d3,(a1)+ | ScreenOut[x, y] := average |
| 1 0001BC | 5240 | | addq.w | #1,d0 | x := x + 1 |
| 1 0001BE | 5344 | | subq.w | #1,d4 | GScounter := GScounter - 1 |
| 1 0001C0 | 6E08 | | bgt.s | dir23.1 | if more pixels in this grid |
| 1 0001C2 | 181A | | move.b | (a2)+,d4 | slope for next grid |
| 1 0001C4 | 2C3B4022 | | move.l | SideComp(pc,d4.w),d6 | main grid component offsets |
| 1 0001C8 | 7820 | | moveq | #XGridSize,d4 | |
| 1 0001CA | 5345 | dir23.1 | subq.w | #1,d5 | OScounter := OScounter - 1 |
| 1 0001CC | 6E08 | | bgt.s | dir23.2 | if more pixels in this grid |
| 1 0001CE | 1A1B | | move.b | (a3)+,d5 | slope for next grid |
| 1 0001D0 | 2E3B5016 | | move.l | SideComp(pc,d5.w),d7 | offset grid component offsets |
| 1 0001D4 | 7A20 | | moveq | #XGridSize,d5 | |
| 1 0001D6 | B07C01FE | dir23.2 | cmp.w | #Border-1,d0 | |
| 1 0001DA | 6FB6 | | ble.s | dir21 | if x <= (Border - 1) |
| 1 0001DC | 5241 | | addq.w | #1,d1 | y := y + 1 |
| 1 0001DE | B27C01FE | | cmp.w | #Border-1,d1 | |
| 1 0001E2 | 6F00FF6E | | ble | dir20 | if y <= (Border - 1) |

| Address | Object | | Statement | | |
|---|---|---|---|---|---|
| 1 0001E6 | 6010 | | bra.s | dir30 | clean up borders and exit |

```
**    Side component offsets.
*

SideComp
1 0001E8 FFFF0001        dc.w    -1,1                        horizontal
1 0001EC F0FF0201        dc.w    0-1-(Border+1),1+(Border+1) positive slope
1 0001F0 FE000200        dc.w    -(Border+1),Border+1        vertical
1 0001F4 01FFFE01        dc.w    0-1+(Border+1),1-(Border+1) negative slope

**    Clear border areas that are garbage because directional
*     filter doesn't operate on the whole image.

1 0001F8 203CFFFFFFFF  dir30  move.l  #(BackFill<<24)+(BackFill<<16)+(BackFill<<8)+BackFill,d0
1 0001FE 323C007F             move.w  #((Border+1)/4)-1,d1
1 000202 226EFFFC             move.l  ScreenOut(a6),a1
1 000206 22C0          dir31  move.l  d0,(a1)+               clear upper raster line
1 000208 51C9FFFC             dbra    d1,dir31
1 00020C 323C007F             move.w  #((Border+1)/4)-1,d1
1 000210 226EFFFC             move.l  ScreenOut(a6),a1
1 000214 D3FC00040000         add.l   #((Border+1)*(Border+1)),a1
1 00021A 2300          dir32  move.l  d0,-(a1)               clear lower raster line
1 00021C 51C9FFFC             dbra    d1,dir32
1 000220 226EFFFC             move.l  ScreenOut(a6),a1
1 000224 323C01FF             move.w  #Border,d1
1 000228 1280          dir33  move.b  d0,(a1)                clear left side
1 00022A 134001FF             move.b  d0,Border(a1)          clear right side
1 00022E D2FC0200             add.w   #Border+1,a1           position to next raster line
1 000232 51C9FFF4             dbra    d1,dir33
1 000236 4CDF3DFF             movem.l (sp)+,a0/a2-a5/d0-d7   restore registers
1 00023A 226EFFFC             move.l  ScreenOut(a6),a1       return output image address
1 00023E 4E5E                 unlk    a6
1 000240 4E75                 rts end
```

0 errors detected.

Unhair - remove  from image.

Address Object     Statement.

```
                xdef    Unhair include macros.def         macro definitions
00000001        NOLIST
                NOLIST include global.def         global symbol definitions
```

| Address | Object | Statement | | |
|---|---|---|---|---|
| | | ** | Global.def - global symbol definitions. | |
| | | * | | |
| | | * | Copyright (C) 1986, CFA Technologies, Inc. | |
| | | | | |
| | | **** | Intensity level definitions. | |
| 00000000 | | L0 | equ | 0 |
| 00000010 | | L1 | equ | 16 |
| 00000020 | | L2 | equ | 32 |
| 00000030 | | L3 | equ | 48 |
| 00000040 | | L4 | equ | 64 |
| 00000050 | | L5 | equ | 80 |
| 00000060 | | L6 | equ | 96 |
| 00000070 | | L7 | equ | 112 |
| 00000080 | | L8 | equ | 128 |
| 00000090 | | L9 | equ | 144 |
| 000000A0 | | L10 | equ | 160 |
| 000000B0 | | L11 | equ | 176 |
| 000000C0 | | L12 | equ | 192 |
| 000000D0 | | L13 | equ | 208 |
| 000000E0 | | L14 | equ | 224 |
| 000000FF | | L15 | equ | 255 |
| | | **** | Useful constants. | |
| 00000009 | | Yshift | equ | 9    ; log 2 of X and Y coordinate bounds |
| 000001FF | | Border | equ | (1<<Yshift)-1   ; X and Y coordinate border |
| | | **** | Character constants. | |
| 00000020 | | Space | equ | $20 |
| 00000007 | | Bel | equ | 'G'-$40 |
| 00000008 | | BS | equ | 'H'-$40 |
| 00000009 | | Tab | equ | 'I'-$40 |
| 0000000A | | LF | equ | 'J'-$40 |
| 0000000C | | FF | equ | 'L'-$40 |
| 0000000D | | CR | equ | 'M'-$40 |
| 0000000E | | SO | equ | 'N'-$40 |
| 0000000F | | SI | equ | 'O'-$40 |
| 00000011 | | Xon | equ | 'Q'-$40 |
| 00000013 | | Xoff | equ | 'S'-$40 |
| 0000001B | | Esc | equ | '['-$40 |
| 0000007F | | Del | equ | $7f |
| 00000019 | | CtrlY | equ | 'Y'-$40 |

**** Constants used to control LEDs

* Legal codes for ButtonLight (SwitchOff also good for FingerLight)

| Address | | Object | Statement | |
|---|---|---|---|---|
| 00000000 | | SwitchOff | equ | 0 |
| 00000001 | | YesAndNo | equ | 1 |
| 00000002 | | Capture | equ | 2 |
| 00000003 | | SwitchTest | equ | 3 |

* Codes to control fluorescent lights

| Address Object | Statement. | | |
|---|---|---|---|
| 00000001 | FluorRoll | equ | 1 |
| 00000002 | FluorSlap | equ | 2 | include section.def     section number definitions

Section definitions.

| | | | |
|---|---|---|---|
| 00000001 | CodeSect | equ | 1 | code and pc-relative constants |
| 00000002 | DataSect | equ | 2 | read/write data area |
| 00000003 | RODataSect | equ | 3 | read only data area |

Assembly options.

| | | | | |
|---|---|---|---|---|
| 00000000 | FillRidges | equ | false | fill in "holes" in ridges too |

00000001        section CodeSect

```
Unhair - remove hairs from image.

#     Algorithm by G. M. Fishbine.
#     Implemented in 68000 assembly language by D. E. Germann.

#     Copyright (C) 1986, CFA Technologies, Inc.

#     entry   (a0.l) = screen buffer address.
#             (d0.w) = hair width in dots.
#             (d1.b) = black/white threshold.

#     exit    hairs removed from image
#             optionally (assembly time), ridge "holes" filled in, too.

#     uses    a - none.
#             d - none.

#     calls   none.
```

```
1 000000 48E7FF40        Unhair  movem.l a1/d0-d7,-(sp)
1 000004 1E01                    move.b  d1,d7          put threshold into a safe register
1 000006 3200                    move.w  d0,d1
1 000008 D241                    add.w   d1,d1          2n
1 00000A 3401                    move.w  d1,d2
1 00000C D440                    add.w   d0,d2
1 00000E 5342                    subq.w  #1,d2          3n-1
1 000010 283C000001FF            move.l  #Border,d4     y := Border downto 0
1 000016 2C04            unh1    move.l  d4,d6
1 000018 7609                    moveq   #Yshift,d3
1 00001A E7A6                    asl.l   d3,d6          convert y-coord to screen offset
1 00001C 2248                    move.l  a0,a1
1 00001E D3C6                    add.l   d6,a1          addr(Screen[0, y])
1 000020 363C01FF                move.w  #Border,d3
```

| Address Object | | Statement | | |
|---|---|---|---|---|
| 1 000024 9642 | | | sub.w | d2,d3 | x := 0 to Border-(3n-1) (d3 counts down)
| 1 000026 BE11 | unh2 | | cmp.b | (a1),d7 |

```
                    ift     FillRidges
              +     IFNE    FillRidges
                    bhi.s   unh4              if Screen[x, y] is a dark pixel
                    endc iff     FillRidges
              +     IFEQ    FillRidges
1 000028 625A       bhi.s   unh8              if Screen[x, y] is a dark pixel
                    endc 1 00002A BE311000           cmp.b   0(a1,d1.w),d7
1 00002E 6254               bhi.s   unh8              if Screen[x+2n, y] is a dark pixel
1 000030 7C01               moveq   #1,d6             i := 1
1 000032 B046               cmp.w   d6,d0
1 000034 6718               beq.s   unh3.5            if n = 1, skip loops
1 000036 3A06               move.w  d6,d5
1 000038 DA41               add.w   d1,d5             i + 2n
1 00003A BE316000   unh3    cmp.b   0(a1,d6.w),d7
1 00003E 6244               bhi.s   unh8              if Screen[x+i, y] is a dark pixel
1 000040 BE315000           cmp.b   0(a1,d5.w),d7
1 000044 623E               bhi.s   unh8              if Screen[x+i+2n, y] is a dark pixel
1 000046 5246               addq.w  #1,d6             i := i + 1
1 000048 5245               addq.w  #1,d5             update i + 2n, too
1 00004A BC40               cmp.w   d0,d6
1 00004C 6DEC               blt.s   unh3              if i < n
1 00004E 7AFF       unh3.5  moveq   #L15,d5           filler := L15
1 000050 6026               bra.s   unh6              make inner pixels match outer pixels 1 000052 BE311000   unh4    cmp.b   0(a1,d1.w),d7
1 000056 632C               bls.s   unh8              if Screen[x+2n, y] is a light pixel
1 000058 7C01               moveq   #1,d6             i := 1
1 00005A B046               cmp.w   d6,d0
1 00005C 6718               beq.s   unh5.5            if n = 1, skip loops
1 00005E 3A06               move.w  d6,d5
1 000060 DA41               add.w   d1,d5             i + 2n
1 000062 BE316000   unh5    cmp.b   0(a1,d6.w),d7
1 000066 631C               bls.s   unh8              if Screen[x+i, y] is a light pixel
1 000068 BE315000           cmp.b   0(a1,d5.w),d7
1 00006C 6316               bls.s   unh8              if Screen[x+i+2n, y] is a light pixel
1 00006E 5246               addq.w  #1,d6             i := i + 1
1 000070 5245               addq.w  #1,d5             update i + 2n, too
1 000072 BC40               cmp.w   d0,d6
1 000074 6DEC               blt.s   unh5              if i < n
1 000076 7A00       unh5.5  moveq   #L0,d5            filler := L0
1 000078 3C00       unh6    move.w  d0,d6             i := n
1 00007A 13856000   unh7    move.b  d5,0(a1,d6.w)     Screen[x+i, y] := filler
1 00007E 5246               addq.w  #1,d6             i := i + 1
1 000080 BC41               cmp.w   d1,d6
1 000082 6DF6               blt.s   unh7              if i < 2n
1 000084 5289       unh8    addq.l  #1,a1             x := x + 1
1 000086 51C8FF9E           dbra    d3,unh2           do next x
1 00008A 51CCFF8A           dbra    d4,unh1           do next y
```

```
1 00008E 4CDF02FF        moves.l (sp)+,a1/d0-d7
1 000092 4E75             rts end 0 errors detected.

program FixCurvatureOffsetGen;  ( for assembly source )

const Vertical = false;

var I, Column: integer;
    Inp, Result: text;
    Offsets: array [0..511] of integer;
    Xold, Yold, X, Y, Min, Max: integer;
    Going: boolean;
    TrayName, FileName: string [20];

const Tab = ^I;

procedure XYMove(XZ, YZ, XN, YN: integer);

( ACM Algorithm 162: X/Y move plotting )

var A, B, D, E, F, T, I, Move: integer;
        Xp, Yp: integer;

function Code(J: integer): integer;
      begin
        if J = 15 then Code := 1
        else Code := J - ((J div 4) * 2);
      end;

procedure Plot(Move: integer);
      var Dir, Pixel, I: integer;
      const OffsetX: array [0..7] of integer = ( 1, 1, 0,-1,-1,-1, 0, 1);
            OffsetY: array [0..7] of integer = ( 0, 1, 1, 1, 0,-1,-1,-1);
      begin
        if Move <= 3 then Dir := 3 - Move
        else Dir := 11 - Move;
        Xp := Xp + OffsetX[Dir];
        Yp := Yp + OffsetY[Dir];
        if Vertical then begin
           Offsets[Yp] := Xp;
           if Xp < Min then Min := Xp;
           end
        else begin
           Offsets[Xp] := Yp;
           if Yp > Max then Max := Yp;
           end;
      end;

begin ( XYMove )
       Xp := XZ;
       Yp := YZ;
```

```
            if (XZ <> XN) or (YZ <> YN) then begin
               A := XN - XZ;
               B := YN - YZ;
               D := A + B;
               T := B - A;
               I := 0;
               if B >= 0 then I := 2;
               if D >= 0 then I := I + 2;
               if T >= 0 then I := I + 2;
               if A >= 0 then I := 8 - I else I := I + 10;
               A := abs(A);
               B := abs(B);
               F := A + B;
               D := B - A;
               if D >= 0 then begin T := A; D := -D; end else T := B;
               E := 0;
               Move := Code(I-1);
               I := Code(I);
               repeat
                  A := D + E;
                  B := T + E + A;
                  if B >= 0 then begin E :=      F := F - 2; Plot(I); end
                  else begin E := E + T; F := F - 1; Plot(Move); end;
               until F <= 0;
            end;
      end;

begin
   for I:=0 to 511 do Offsets[I] := 0;
   Going := false;
   write('Tray name: ');
   readln(TrayName);
   FileName := TrayName + '.cur';
   assign(Inp,FileName);
   reset(Inp);
   while not eof(Inp) do begin
      readln(Inp,X,Y);
      if Going then XYMove(Xold,Yold,X,Y)
      else begin
         if Vertical then begin
            Offsets[Y] := X;
            Min := X;
            end
         else begin
            Offsets[X] := Y;
            Max := Y;
            end;
         end;
      Xold := X;
      Yold := Y;
      Going := true;
      end;
   for I:=0 to 511 do begin
      if Offsets[I] > 0 then begin
         if Vertical then
            Offsets[I] := Offsets[I] - Min
         else
```

```
      Offsets[I] := Max - Offsets[I];
    end;
  end;
FileName := TrayName + '.inc';
assign(Result,FileName);
rewrite(Result);
writeln(Result,TrayName);
Column := 0;
for I:=0 to 511 do begin
   if Column = 0 then write(Result,Tab,'dc w',Tab);
   write(Result,Offsets[I]);
   Column := Column + 1;
   if (I = 511) or (Column )= 10) then begin
      writeln(Result);
      Column := 0;
    end
   else
      write(Result,',');
   end;
writeln(Result);
close(Result);
end
```

FixCurvature - correct curvature in image.

Address Object        Statement.

```
                xdef    FixCurvature 00000001        section 1 include global.def       global symbol definitions
        **      Global.def - global symbol definitions.
        *
        *       Copyright (C) 1986, CFA Technologies, Inc.

****    Intensity level definitions.

00000000        L0      equ     0
00000010        L1      equ     16
00000020        L2      equ     32
00000030        L3      equ     48
00000040        L4      equ     64
00000050        L5      equ     80
00000060        L6      equ     96
00000070        L7      equ     112
00000080        L8      equ     128
00000090        L9      equ     144
000000A0        L10     equ     160
000000B0        L11     equ     176
000000C0        L12     equ     192
000000D0        L13     equ     208
```

| Address Object | Statement | | |
|---|---|---|---|
| 000000E0 | L14 | equ | 224 |
| 000000FF | L15 | equ | 255 |

**** Useful constants.

| | | | | |
|---|---|---|---|---|
| 00000009 | Yshift | equ | 9 | ; log 2 of X and Y coordinate bounds |
| 000001FF | Border | equ | (1<<Yshift)-1 | ; X and Y coordinate border |

**** Character constants.

| | | | |
|---|---|---|---|
| 00000020 | Space | equ | $20 |
| 00000007 | Bel | equ | 'G'-$40 |
| 00000008 | BS | equ | 'H'-$40 |
| 00000009 | Tab | equ | 'I'-$40 |
| 0000000A | LF | equ | 'J'-$40 |
| 0000000C | FF | equ | 'L'-$40 |
| 0000000D | CR | equ | 'M'-$40 |
| 0000000E | SO | equ | 'N'-$40 |
| 0000000F | SI | equ | 'O'-$40 |
| 00000011 | Xon | equ | 'Q'-$40 |
| 00000013 | Xoff | equ | 'S'-$40 |
| 0000001B | Esc | equ | '['-$40 |
| 0000007F | Del | equ | $7f |
| 00000019 | CtrlY | equ | 'Y'-$40 |

**** Constants used to control LEDs

* Legal codes for ButtonLight (SwitchOff also good for FingerLight)

| | | | |
|---|---|---|---|
| 00000000 | SwitchOff | equ | 0 |
| 00000001 | YesAndNo | equ | 1 |
| 00000002 | Capture | equ | 2 |
| 00000003 | SwitchTest | equ | 3 |

* Codes to control fluorescent lights

| | | | |
|---|---|---|---|
| 00000001 | FluorRoll | equ | 1 |
| 00000002 | FluorSlap | equ | 2 |

**** Assembly constants

| | | | | |
|---|---|---|---|---|
| 000000FF | Background | equ | L15 | background fill value |

```
***   FixCurvature - correct curvature in image.
*     Based on Pascal implementation by M. S. Ransom.
*     Converted to 68000 assembler by D. E. Germann.
*
*     Copyright (C) 1986, CFA Technologies, Inc.
*
*     entry  (a5.l) = screen image address.
```

```
Address Object           Statement.
                         ‡            (d0.w) = tray number.
                         ‡
                         ‡    exit    image corrected.
                         ‡
                         ‡    uses    a - none.
                         ‡            d - none.
                         ‡
                         ‡    calls   none.

FixCurvature
1 000000 B07C0005            cmp.w    #4+1,d0
1 000004 6700005C            beq      fix30                        if slap prints, skip decurve
1 000008 48E7E7A0            movem.l  a0/a2/d0-d2/d5-d7,-(sp)      save registers
1 00000C 45FA0056            lea      Offsets(pc),a2               offset pointer table address
1 000010 E540                asl.w    #2,d0                        convert tray number to table offset
1 000012 247200FC            move.l   -4(a2,d0.w),a2               get table address for this tray ‡      if desired, this is the place for a test for horiz/vert decurve.
                         ‡      Horizontal decurve.

1 000016 D5FC00000400  fix10  add.l    #(Border+1)*2,a2            move past end of table
1 00001C 2E3C00000200         move.l   #1<<Yshift,d7               y-increment
1 000022 7C09                 moveq    #Yshift,d6
1 000024 7AFF                 moveq    #Background,d5              fill value for end of lines
1 000026 303C01FF             move.w   #Border,d0                  x := Border downto 0
1 00002A 7400          fix11  moveq    #0,d2
1 00002C 3422                 move.w   -(a2),d2                    off := Offsets[x]
1 00002E 6F2A                 ble.s    fix14                       if not correcting this column
1 000030 323C01FF             move.w   #Border,d1
1 000034 9242                 sub.w    d2,d1                       y := Border downto off
1 000036 207C0003FE00         move.l   #Border<<Yshift,a0
1 00003C D1CD                 add.l    a5,a0                       Screen[0, Border]
1 00003E D0C0                 add.w    d0,a0                       Screen[x, Border]
1 000040 EDA2                 asl.l    d6,d2                       convert offset to y-coordinate address
1 000042 4482                 neg.l    d2                          generate -offset value
1 000044 10B02800      fix12  move.b   0(a0,d2.l),(a0)             Screen[x, y] := Screen[x, y-off]
1 000048 91C7                 sub.l    d7,a0                       y := y - 1
1 00004A 51C9FFF8             dbra     d1,fix12                    if more pixels to move in this column
1 00004E 3412                 move.w   (a2),d2                     off := Offsets[x]
1 000050 5342                 subq.w   #1,d2                       i := off-1 downto 0
1 000052 1085          fix13  move.b   d5,(a0)                     clear pixel
1 000054 91C7                 sub.l    d7,a0                       y := y - 1
1 000056 51CAFFFA             dbra     d2,fix13                    if more pixels to clear in this column
1 00005A 51C8FFCE      fix14  dbra     d0,fix11                    if more columns to decurve
1 00005E 4CDF05E7      fix20  movem.l  (sp)+,a0/a2/d0-d2/d5-d7     restore registers
1 000062 4E75          fix30  rts 1 000064 000000740000  Offsets dc.l    Curve1,Curve2,Curve3,Curve4
         047400000874
         00000C74 nolist end 0 errors detected.
```

```pascal
program ChangeXConstantGen;  { for assembler source }
const Tab = 'I;
      Border = 511;
var I, Column, tray, MeetPoint: integer;
    Numerator, Denominator, LeftEdge, RightEdge: integer;
    Result: text;
    X, OldX, OldMiddle, NewMiddle: integer;
    Offsets: array [0..511] of integer;
    Answer: char;
    Linear, AlignEdge, Shrinking: boolean;

procedure GenerateOffsets;
  var I, OldX, Y, NewX, PreviousOldX, Xincrement, Alignment: integer;
      Going: boolean;
      CoordFile: text;
      FileName: string [80];

procedure XYMove(XZ, YZ, XN, YN: integer);

{ ACM Algorithm 162: X/Y move plotting } var A, B, D, E, F, T, I, Move: integer;
          Xp, Yp: integer;

function Code(J: integer): integer;
        begin
          if J = 15 then Code := 1
          else Code := J - ((J div 4) * 2);
        end;

procedure Plot(Move: integer);
        var Dir, Pixel, I: integer;
        const OffsetX: array [0..7] of integer = ( 1, 1, 0,-1,-1,-1, 0, 1);
              OffsetY: array [0..7] of integer = ( 0, 1, 1, 1, 0,-1,-1,-1);
        begin
          if Move <= 3 then Dir := 3 - Move
          else Dir := 11 - Move;
          Xp := Xp + OffsetX[Dir];
          Yp := Yp + OffsetY[Dir];
          if (Yp >= 0) and (Yp <= Border) then
              Offsets[Yp] := Xp;
        end;

begin  { XYMove }
        Xp := XZ;
        Yp := YZ;
        if (XZ <> XN) or (YZ <> YN) then begin
            A := XN - XZ;
            B := YN - YZ;
            D := A + B;
            T := B - A;
            I := 0;
            if B >= 0 then I := 2;
            if D >= 0 then I := I + 2;
            if T >= 0 then I := I + 2;
            if A >= 0 then I := 3 - I else I := I + 10;
            A := abs(A);
```

```
              B := abs(B);
              F := A + B;
              D := B - A;
              if D >= 0 then begin T := A; D := -D; end else T := B;
              E := 0;
              Move := Code(I-1);
              I := Code(I);
              repeat
                 A := D + E;
                 B := T + E + A;
                 if B >= 0 then begin E := A; F := F - 2; Plot(I); end
                 else begin E := E + T; F := F - 1; Plot(Move); end;
              until F <= 0;
           end;
        end;

begin  { GenerateOffsets }
  write('Enter X increment, in dots:        ');
  readln(Xincrement);
  write('Enter coordinate file name:        ');
  readln(FileName);
  assign(CoordFile,FileName);
  reset(CoordFile);
  for I:=0 to 511 do Offsets[I] := -1;
  Going := false;
  NewX := 0;
  while not eof(CoordFile) do begin
     readln(CoordFile,OldX,Y);
     if Going then begin
        XYMove(PreviousOldX,NewX,OldX,NewX+Xincrement);
        NewX := NewX + Xincrement;
        end
     else begin
        Offsets[NewX] := OldX;
        LeftEdge := OldX;
        end;
     PreviousOldX := OldX;
     Going := true;
     end;
  close(CoordFile);
  if NewX > Border then NewX := Border;
  Shrinking := (NewX < (Offsets[NewX] - LeftEdge));
  if not AlignEdge then begin
     I := 0;
     while (I < NewX) and (Offsets[I] < OldMiddle) do I := I + 1;
     if ((I = 0) and (Offsets[I] > OldMiddle)) or
        (Offsets[I] < OldMiddle) then
        begin
        writeln('Old middle is outside picture bounds.');
        Alignment := 0;
        end
     else Alignment := NewMiddle - I;
     if Alignment >= 0 then begin
        for I:=NewX downto 0 do begin
           Offsets[I+Alignment] := Offsets[I];
           end;
```

```
            for I:=Alignment-1 downto 0 do
                Offsets[I] := -1;
            end;
        else begin
            for I:=-Alignment to NewX do begin
                Offsets[I+Alignment] := Offsets[I];
                end;
            for I:=NewX+Alignment+1 to NewX do
                Offsets[I] := -1;
            end;
        end;
    end; { GenerateOffsets } begin
 assign(Result,'changex.def');
 rewrite(Result);
 writeln(Result);
 writeln(Result,'Shrinking',Tab,'equ',Tab,'-4',Tab,
    'offset of shrink or expand flag');
 writeln(Result,'MeetPoint',Tab,'equ',Tab,'-2',Tab,'offset of MeetPoint');
 close(Result);
 assign(Result,'changex.inc');
 rewrite(Result);
 for tray := 1 to 5 do begin
    writeln('Tray ', tray:1, ': ');
    write('Linear or Non-linear change?         ');
    readln(Answer);
    Linear := ((Answer = 'L') or (Answer = 'l'));
    write('Align on left edge or middle?        ');
    readln(Answer);
    AlignEdge := ((Answer = 'l') or (Answer = 'L'));
    if not AlignEdge then begin
        write('Enter old middle X coordinate:       ');
        readln(OldMiddle);
        write('Enter new middle X coordinate:       ');
        readln(NewMiddle);
        end;
    if not Linear then GenerateOffsets
    else begin
        write('Enter ratio numerator and denominator: ');
        readln(Numerator,Denominator);
        Shrinking := (Numerator < Denominator);
        write('Enter Left and Right edge coordinates: ');
        readln(LeftEdge,RightEdge);
        if AlignEdge then begin
            for X:=0 to Border do begin
                OldX := round(((X+0.0) * Denominator / Numerator) + LeftEdge);
                if OldX < LeftEdge then OldX := -1;
                if OldX > RightEdge then OldX := -1;
                Offsets[X] := OldX;
                end;
            end
        else begin
            for X:=0 to Border do begin
                OldX := round((((X-NewMiddle)+0.0) * Denominator) / Numerator)
```

```
                    + OldMiddle);
            if OldX < LeftEdge then OldX := -1;
            if OldX > RightEdge then OldX := -1;
            Offsets[X] := OldX;
          end;
      end;
   end;
X := 0;
while (X < Border) and (X <> Offsets[X]) do begin
   if Offsets[X] >= 0 then begin
      if (Shrinking and (X > Offsets[X])) or
         ((not Shrinking) and (X < Offsets[X])) then
         MeetPoint := Border
      else
         MeetPoint := -1;
      end;
   X := X + 1;
   end;
if X = Offsets[X] then MeetPoint := X;

writeln(Result);
writeln(Result,'#',Tab,'Tray ',tray:1);
writeln(Result);
if Shrinking then
   writeln(Result,Tab,'dc.w',Tab,'$ff',Tab,'shrinking')
else
   writeln(Result,Tab,'dc.w',Tab,'0',Tab,'not shrinking');
writeln(Result,Tab,'dc.w',Tab,MeetPoint);
writeln(Result,'Off',tray:1);
   Column := 0;
   for I:=0 to Border do begin
      if Column = 0 then write(Result,'dc.w',Tab);
      write(Result,Offsets[I]);
      Column := Column + 1;
      if (I = Border) or (Column >= 10) then begin
         writeln(Result);
         Column := 0;
         end
      else
         write(Result,',');
      end;
   writeln(Result);
   end;
writeln(Result);
writeln(Result,'Offsets');
for tray := 1 to 5 do
   writeln(Result,Tab,'dc.l',Tab,'Off',tray:1);
close(Result);
end.
```

ChangeX - change in X direction.

Address Object    Statement.

xdef    ChangeX 00000001          section 1 include global.def          global symbol definitions
                  ;*      Global.def - global symbol definitions.
                  ;
                  ;       Copyright (C) 1986, CFA Technologies, Inc.

;***    Intensity level definitions.

00000000          L0      equ     0
00000010          L1      equ     16
00000020          L2      equ     32
00000030          L3      equ     48
00000040          L4      equ     64
00000050          L5      equ     80
00000060          L6      equ     96
00000070          L7      equ     112
00000080          L8      equ     128
00000090          L9      equ     144
000000A0          L10     equ     160
000000B0          L11     equ     176
000000C0          L12     equ     192
000000D0          L13     equ     208
000000E0          L14     equ     224
000000FF          L15     equ     255

;***    Useful constants.

00000009          Yshift  equ     9               ; log 2 of X and Y coordinate bounds
000001FF          Border  equ     (1<<Yshift)-1   ; X and Y coordinate border ;***    Character constants.

00000020          Space   equ     $20
00000007          Bel     equ     'G'-$40
00000008          BS      equ     'H'-$40
00000009          Tab     equ     'I'-$40
0000000A          LF      equ     'J'-$40
0000000C          FF      equ     'L'-$40
0000000D          CR      equ     'M'-$40
0000000E          SO      equ     'N'-$40
0000000F          SI      equ     'O'-$40
00000011          Xon     equ     'Q'-$40
00000013          Xoff    equ     'S'-$40
0000001B          Esc     equ     '['-$40

| Address | Object | Statement |
|---|---|---|
| | 0000007F | Del    equ    $7f |
| | 00000019 | CtrlY  equ    'Y'-$40 |

Constants used to control LEDs

\# Legal codes for ButtonLight (SwitchOff also good for FingerLight)

| | 00000000 | SwitchOff   equ   0 |
|---|---|---|
| | 00000001 | YesAndNo    equ   1 |
| | 00000002 | Capture     equ   2 |
| | 00000003 | SwitchTest  equ   3 |

\# Codes to control fluorescent lights

| | 00000001 | FluorRoll   equ   1 |
|---|---|---|
| | 00000002 | FluorSlap   equ   2 |

```
            include changex.def         changex symbol definitions
```

| FFFFFFFC | Shrinking   equ   -4    offset of shrink or expand flag |
|---|---|
| FFFFFFFE | MeetPoint   equ   -2    offset of MeetPoint |

Assembly constants.

| 000000FF | Background   equ   L15    background fill value |
|---|---|

```
ChangeX - change image in X direction.
#     Based on Pascal implementation by M. S. Ransom.
#     Converted to 68000 assembler by D. E. Germann.

#     Copyright (C) 1986, CFA Technologies, Inc.

#     entry  (a0.l) = screen image address.
#            (d0.w) = tray number.

#     exit   image corrected.

#     uses   a - none.
#            d - none.

#     calls  move.
```

| 1 000000 | 48E7FE30  | ChangeX movem.l  a2-a4/d0-d6,-(sp)    save registers |
|---|---|---|
| 1 000004 | 45FA14A4  |         lea      Offsets(pc),a2        offset pointer table address |
| 1 000008 | E540      |         asl.w    #2,d0                 convert tray number to table offset |
| 1 00000A | 247200FC  |         move.l   -4(a2,d0.w),a2        get table address for this tray |
| 1 00000E | 4A6AFFFC  |         tst.w    Shrinking(a2) |

```
Address Object      Statement.
1 000012 6722                    beq.s    chx2              if expanding image
1 000014 302AFFFE                move.w   MeetPoint(a2),d0  initial x := MeetPoint
1 000018 7200                    moveq    #0,d1             final x := 0
1 00001A 74FF                    moveq    #-1,d2            count down
1 00001C 8041                    cmp.w    d1,d0
1 00001E 6D02                    blt.s    chx1              if nothing to do on this side
1 000020 613A                    bsr.s    move              compress left half of image
1 000022 302AFFFE      chx1      move.w   MeetPoint(a2),d0
1 000026 5240                    addq.w   #1,d0             initial x := MeetPoint+1
1 000028 323C01FF                move.w   #Border,d1        final x := Border
1 00002C 7401                    moveq    #1,d2             count up
1 00002E 8041                    cmp.w    d1,d0
1 000030 6E24                    bgt.s    chx4              if nothing to do on this side
1 000032 6128                    bsr.s    move              compress right half of image
1 000034 6020                    bra.s    chx4

1 000036 7000        chx2        moveq    #0,d0             initial x := 0
1 000038 322AFFFE                move.w   MeetPoint(a2),d1  final x := MeetPoint
1 00003C 7401                    moveq    #1,d2             count up
1 00003E 8041                    cmp.w    d1,d0
1 000040 6E02                    bgt.s    chx3              if nothing to do on this side
1 000042 6118                    bsr.s    move              expand left half of image
1 000044 303C01FF    chx3        move.w   #Border,d0        initial x := Border
1 000048 322AFFFE                move.w   MeetPoint(a2),d1
1 00004C 5241                    addq.w   #1,d1             final x := MeetPoint+1
1 00004E 74FF                    moveq    #-1,d2            count down
1 000050 8041                    cmp.w    d1,d0
1 000052 6002                    blt.s    chx4              if nothing to do on this side
1 000054 6106                    bsr.s    move              expand right half of image
1 000056 4CDF1C7F    chx4        movem.l  (sp)+,a2-a4/d0-d6 restore registers
1 00005A 4E75                    rts
```

```
**      move - expand or compress portion of image.
*
*       entry   (a0.l) = screen address.
*               (a2.l) = offset table base address.
*               (d0.w) = initial x.
*               (d1.w) = final x.
*               (d2.w) = x increment (+/- 1).
*
*       exit    screen portion expanded or compressed
*
*       uses    a - 3, 4.
*               d - 0, 1, 3, 5, 6.
*
*       calls   none.

1 00005C D242         move       add.w    d2,d1             final value + increment
1 00005E 287C00000200            move.l   #1<<Yshift,a4     y increment
1 000064 7AFF                    moveq    #Background,d5    preload background value
1 000066 3C3C01FF     mov1       move.w   #Border,d6        y := 0 to Border (d6 counts down)
1 00006A 2648                    move.l   a0,a3             Screen[0, y]
```

```
Address Object         Statement.
1 00006C 3600                    move.w  d0,d3
1 00006E D643                    add.w   d3,d3
1 000070 36323000                move.w  0(a2,d3.w),d3        OldX := Offset[x]
1 000074 6B14                    bmi.s   mov4                 if this column is to be cleared
1 000076 17B330000000    mov2    move.b  0(a3,d3.w),0(a3,d0.w) Screen[x, y] := Screen[OldX, y]
1 00007C 07CC                    add.l   a4,a3                y := y + 1
1 00007E 51CEFFF6                dbra    d6,mov2              if more pixels to move in this column
1 000082 0042            mov3    add.w   d2,d0                x := x + increment
1 000084 B041                    cmp.w   d1,d0
1 000086 66DE                    bne.s   mov1                 if more columns to process
1 000088 4E75                    rts 1 00008A 17850000        mov4    move.b  d5,0(a3,d0.w)        Screen[x, y] := Background
1 00008E 07CC                    add.l   a4,a3                y := y + 1
1 000090 51CEFFF8                dbra    d6,mov4              if more pixels to clear in this column
1 000094 60EC                    bra.s   mov3
``` nolist end 0 errors detected.

```
program ChangeYConstantGen;  { for assembler source }
const Tab = ^I;
      Border = 511;
var I, Column, tray: integer;
    Result: text;
    Y, OldY, MeetPoint: integer;
    ExpansionFactor: real;
    Numerator, Denominator, OldMiddle, NewMiddle, TopEdge, BottomEdge: integer;
    Offsets: array [0..511] of integer;
    Answer: char;
begin
 write('Expansion coefficient: ');
 readln(ExpansionFactor);
 assign(Result,'changey.def');
 rewrite(Result);
 writeln(Result,'Numerator',Tab,'equ',Tab,'-6',Tab,'offset of Numerator');
 writeln(Result,'Denominator',Tab,'equ',Tab,'-4',Tab,'offset of Denominator');
 writeln(Result,'MeetPoint',Tab,'equ',Tab,'-2',Tab,'offset of MeetPoint');
 close(Result);
 assign(Result,'changey.inc');
 rewrite(Result);
 for tray := 1 to 5 do begin
    write('Numerator and denominator for tray ', tray:1, ': ');
    readln(Numerator, Denominator);
    Numerator := round(Numerator * ExpansionFactor);
    write('Enter Top and Bottom edge coordinates: ');
```

```
readln(TopEdge,BottomEdge);
write('Align on top edge or middle?        ');
readln(Answer);
if (Answer = 't') or (Answer = 'T') then begin
    for Y:=0 to Border do begin
        OldY := round(((Y+0.0) * Denominator / Numerator) + TopEdge);
        if OldY < TopEdge then OldY := -1;
        if OldY > BottomEdge then OldY := -1;
        Offsets[Y] := OldY;
        end;
    if (Numerator-Denominator) > 0 then begin
        if ((TopEdge+0.0)*Numerator) > ((Border+0.0)*(Numerator-Denominator))
            then MeetPoint := Border
        else if TopEdge < 0 then MeetPoint := -1
        else MeetPoint :=
            round((TopEdge+0.0) * Numerator / (Numerator-Denominator));
        end
    else if (Numerator-Denominator) < 0 then begin
        if ((TopEdge+0.0)*Numerator) < ((Border+0.0)*(Numerator-Denominator))
            then MeetPoint := Border
        else if TopEdge > 0 then MeetPoint := -1
        else MeetPoint :=
            round((TopEdge+0.0) * Numerator / (Numerator-Denominator));
        end
    else begin
        if TopEdge >= 0 then MeetPoint := Border
        else MeetPoint := -1;
        end;
    end
else begin
    write('Enter old middle Y coordinate:         ');
    readln(OldMiddle);
    write('Enter new middle Y coordinate:         ');
    readln(NewMiddle);
    for Y:=0 to Border do begin
        OldY := round((((Y-NewMiddle)+0.0) * Denominator) / Numerator)
            + OldMiddle);
        if OldY < TopEdge then OldY := -1;
        if OldY > BottomEdge then OldY := -1;
        Offsets[Y] := OldY;
    end;
if (Numerator-Denominator) > 0 then begin
    if ((OldMiddle+0.0)*Numerator - (NewMiddle+0.0)*Denominator >
        ((Border+0.0)*(Numerator-Denominator))
        then MeetPoint := Border
    else if ((OldMiddle+0.0)*Numerator) < ((NewMiddle+0.0)*Denominator)
        then MeetPoint := -1
    else MeetPoint :=
        round( ((OldMiddle+0.0)*Numerator - (NewMiddle+0.0)*Denominator) /
            (Numerator - Denominator) );
    end
else if (Numerator-Denominator) < 0 then begin
    if ((OldMiddle+0.0)*Numerator - (NewMiddle+0.0)*Denominator) <
        ((Border+0.0)*(Numerator-Denominator))
        then MeetPoint := Border
    else if ((OldMiddle+0.0)*Numerator) > ((NewMiddle+0.0)*Denominator)
        then MeetPoint := -1
```

```
      else MeetPoint :=
         round( ((OldMiddle+0.0)*Numerator - (NewMiddle+0.0)*Denominator) /
            (Numerator - Denominator) );
       end
     else begin
        if NewMiddle > OldMiddle then MeetPoint := -1
        else MeetPoint := Border;
        end;
      end;
   if MeetPoint < 0 then MeetPoint := -1;
   if MeetPoint > Border then MeetPoint := Border;
   writeln(Result);
   writeln(Result,'*',Tab,'Tray ',tray:1,': ');
   writeln(Result);
   writeln(Result,Tab,'dc.w',Tab,Numerator,',',Denominator);
   writeln(Result,Tab,'dc.w',Tab,MeetPoint);
   writeln(Result,'Off',tray:1);
   Column := 0;
   for I:=0 to Border do begin
      if Column = 0 then write(Result,Tab,'dc.w',Tab);
      write(Result,Offsets[I]);
      Column := Column + 1;
      if (I = Border) or (Column >= 10) then begin
         writeln(Result);
         Column := 0;
         end
      else
         write(Result,',');
      end;
    writeln(Result);
   end;
 writeln(Result);
 writeln(Result,'Offsets');
 for tray := 1 to 5 do
    writeln(Result,Tab,'dc.l',Tab,'Off',tray:1);
 close(Result);
end.
```

ChangeY - change in Y direction

Address Object     Statement.

xdef    ChangeY 00000001           section 1 include global.def        global symbol definitions
            **     Global.def - global symbol definitions.
            *
            *      Copyright (C) 1986, CFA Technologies, Inc.

****   Intensity level definitions.

00000000    L0     equ    0

```
00000010        L1      equ     16
00000020        L2      equ     32
00000030        L3      equ     48
00000040        L4      equ     64
00000050        L5      equ     80
00000060        L6      equ     96
00000070        L7      equ     112
00000080        L8      equ     128
00000090        L9      equ     144
000000A0        L10     equ     160
000000B0        L11     equ     176
000000C0        L12     equ     192
000000D0        L13     equ     208
000000E0        L14     equ     224
000000FF        L15     equ     255

****    Useful constants.

00000009        Yshift  equ     9               ; log 2 of X and Y coordinate bounds
000001FF        Border  equ     (1<<Yshift)-1   ; X and Y coordinate border

****    Character constants.

00000020        Space   equ     $20
00000007        Bel     equ     'G'-$40
00000008        BS      equ     'H'-$40
00000009        Tab     equ     'I'-$40
0000000A        LF      equ     'J'-$40
0000000C        FF      equ     'L'-$40
0000000D        CR      equ     'M'-$40
0000000E        SO      equ     'N'-$40
0000000F        SI      equ     'O'-$40
00000011        Xon     equ     'Q'-$40
00000013        Xoff    equ     'S'-$40
0000001B        Esc     equ     '['-$40
0000007F        Del     equ     $7f
00000019        CtrlY   equ     'Y'-$40

****    Constants used to control LEDs

* Legal codes for ButtonLight (SwitchOff also good for FingerLight)

00000000        SwitchOff       equ     0
00000001        YesAndNo        equ     1
00000002        Capture         equ     2
00000003        SwitchTest      equ     3

* Codes to control fluorescent lights

00000001        FluorRoll       equ     1
00000002        FluorSlap       equ     2 include changey def              changey symbol definitions
FFFFFFFA        Numerator       equ     -6      offset of Numerator
FFFFFFFC        Denominator     equ     -4      offset of Denominator
FFFFFFFE        MeetPoint       equ     -2      offset of MeetPoint
```

```
****   Assembly constants.

FFFFFFFF      Background     equ      $FFFFFFFF      background fill value

***    ChangeY - change image in Y direction.
 *     Based on Pascal implementation by M. S. Ransom.
 *     Converted to 68000 assembler by D. E. Germann.
 *
 *     Copyright (C) 1986, CFA Technologies, Inc.
 *
 *     entry   (a0.l) = screen image address.
 *             (d0.w) = tray number.
 *
 *     exit    image corrected.
 *
 *     uses    a - none.
 *             d - none.
 *
 *     calls   move.

Address Object          Statement.
1 000000 48E7FE38       ChangeY   movem.l   a2-a4/d0-d6,-(sp)      save registers
1 000004 45FA14B4                 lea       Offsets(pc),a2         offset pointer table address
1 000008 E540                     asl.w     #2,d0                  convert tray number to table offset
1 00000A 247200FC                 move.l    -4(a2,d0.w),a2         get table address for this tray
1 00000E 3C2AFFFA                 move.w    Numerator(a2),d6
1 000012 BC6AFFFC                 cmp.w     Denominator(a2),d6
1 000016 6C22                     bge.s     chy2                   if expanding image
1 000018 302AFFFE                 move.w    MeetPoint(a2),d0       initial y := MeetPoint
1 00001C 7200                     moveq     #0,d1                  final y := 0
1 00001E 74FF                     moveq     #-1,d2                 count down
1 000020 B041                     cmp.w     d1,d0
1 000022 6D02                     blt.s     chy1                   if nothing to do on this side
1 000024 613A                     bsr.s     move                   compress top half of image
1 000026 302AFFFE       chy1      move.w    MeetPoint(a2),d0
1 00002A 5240                     addq.w    #1,d0                  initial y := MeetPoint+1
1 00002C 323C01FF                 move.w    #Border,d1             final y := Border
1 000030 7401                     moveq     #1,d2                  count up
1 000032 B041                     cmp.w     d1,d0
1 000034 6E24                     bgt.s     chy4                   if nothing to do on this side
1 000036 6128                     bsr.s     move                   compress bottom half of image
1 000038 6020                     bra.s     chy4

1 00003A 7000          chy2       moveq     #0,d0                  initial y := 0
1 00003C 322AFFFE                 move.w    MeetPoint(a2),d1       final y := MeetPoint
1 000040 7401                     moveq     #1,d2                  count up
1 000042 B041                     cmp.w     d1,d0
1 000044 6E02                     bgt.s     chy3                   if nothing to do on this side
1 000046 6118                     bsr.s     move                   expand top half of image
1 000048 303C01FF      chy3       move.w    #Border,d0             initial y := Border
1 00004C 322AFFFE                 move.w    MeetPoint(a2),d1
1 000050 5241                     addq.w    #1,d1                  final y := MeetPoint+1
1 000052 74FF                     moveq     #-1,d2                 count down
1 000054 B041                     cmp.w     d1,d0
```

| Address Object | | Statement | | |
|---|---|---|---|---|
| 1 000056 6D02 | | | blt.s chy4 | if nothing to do on this side |
| 1 000058 610E | | | bsr.s move | expand bottom half of image |
| 1 00005A 4CDF1C7F | | chy4 | movem.l (sp)+,a2-a4/d0-d6 | restore registers |
| 1 00005E 4E75 | | | rts | |

```
*       move - expand or compress portion of image.
*
*       entry   (a0.l) = screen address.
*               (a2.l) = offset table base address.
*               (d0.w) = inital y.
*               (d1.w) = final y
*               (d2.w) = y increment (+/- 1).
*
*       exit    screen portion expanded or compressed.
*
*       uses    a - 3, 4
*               d - 0, 1, 3, 4, 5, 6.
*
*       calls   none.
```

| | | | | |
|---|---|---|---|---|
| 1 000060 D242 | | move | add.w d2,d1 | final value + increment |
| 1 000062 7AFF | | | moveq #Background,d5 | preload background value |
| 1 000064 7809 | | | moveq #Yshift,d4 | |
| 1 000066 3C3C0080 | | mov1 | move.w #(Border+1)/4,d6 | x := 0 to Border (d6 counts down) |
| 1 00006A 7600 | | | moveq #0,d3 | |
| 1 00006C 3600 | | | move.w d0,d3 | |
| 1 00006E E9A3 | | | asl.l d4,d3 | convert to coordinate offset |
| 1 000070 2648 | | | move.l a0,a3 | |
| 1 000072 D7C3 | | | add.l d3,a3 | Screen[0, y] |
| 1 000074 7600 | | | moveq #0,d3 | |
| 1 000076 3600 | | | move.w d0,d3 | |
| 1 000078 D643 | | | add.w d3,d3 | |
| 1 00007A 36323000 | | | move.w 0(a2,d3.w),d3 | OldY := Offset[y] |
| 1 00007E 6B14 | | | bmi.s mov4 | if this row is to be cleared |
| 1 000080 E9A3 | | | asl.l d4,d3 | convert to coordinate offset |
| 1 000082 2848 | | | move.l a0,a4 | |
| 1 000084 D9C3 | | | add.l d3,a4 | Screen[0, OldY] |
| 1 000086 26DC | | mov2 | move.l (a4)+,(a3)+ | Screen[x, y] := Screen[x, OldY] |
| 1 000088 51CEFFFC | | | dbra d6,mov2 | if more pixels to move in this row |
| 1 00008C D042 | | mov3 | add.w d2,d0 | y := y + increment |
| 1 00008E B041 | | | cmp.w d1,d0 | |
| 1 000090 66D4 | | | bne.s mov1 | if more rows to process |
| 1 000092 4E75 | | | rts | |
| 1 000094 26C5 | | mov4 | move.l d5,(a3)+ | Screen[x, y] := Background |
| 1 000096 51CEFFFC | | | dbra d6,mov4 | if more pixels to clear in this row |
| 1 00009A 60F0 | | | bra.s mov3 | |

```
        nolist end
```

0 errors detected.

Bitmap - convert grey-scale image to b&w bitmap

```
Address Object      Statement.

xdef    Bitmap 00000001            section 1 include global.def          include global symbol definitions
                    ;*      Global.def - global symbol definitions.
                    ;
                    ;       Copyright (C) 1986, CFA Technologies, Inc.

;***    Intensity level definitions.

00000000            L0      equ     0
00000010            L1      equ     16
00000020            L2      equ     32
00000030            L3      equ     48
00000040            L4      equ     64
00000050            L5      equ     80
00000060            L6      equ     96
00000070            L7      equ     112
00000080            L8      equ     128
00000090            L9      equ     144
000000A0            L10     equ     160
000000B0            L11     equ     176
000000C0            L12     equ     192
000000D0            L13     equ     208
000000E0            L14     equ     224
000000FF            L15     equ     255

;***    Useful constants.

00000009            Yshift  equ     9                   ; log 2 of X and Y coordinate bounds
000001FF            Border  equ     (1<<Yshift)-1       ; X and Y coordinate border ;***    Character constants.

00000020            Space   equ     $20
00000007            Bel     equ     'G'-$40
00000008            BS      equ     'H'-$40
00000009            Tab     equ     'I'-$40
0000000A            LF      equ     'J'-$40
0000000C            FF      equ     'L'-$40
0000000D            CR      equ     'M'-$40
0000000E            SO      equ     'N'-$40
0000000F            SI      equ     'O'-$40
00000011            Xon     equ     'Q'-$40
00000013            Xoff    equ     'S'-$40
0000001B            Esc     equ     '['-$40
0000007F            Del     equ     $7F
```

| Address | Object | Statement | | | |
|---|---|---|---|---|---|
| 00000019 | | CtrlY | equ | 'Y'-$40 | |

Constants used to control LEDs

Legal codes for ButtonLight (SwitchOff also good for FingerLight)

| | | | | |
|---|---|---|---|---|
| 00000000 | SwitchOff | equ | 0 | |
| 00000001 | YesAndNo | equ | 1 | |
| 00000002 | Capture | equ | 2 | |
| 00000003 | SwitchTest | equ | 3 | |

Codes to control fluorescent lights

| | | | | |
|---|---|---|---|---|
| 00000001 | FluorRoll | equ | 1 | |
| 00000002 | FluorSlap | equ | 2 | |

| | | | | |
|---|---|---|---|---|
| 00000040 | BitBytes | equ | (Border+1)/8 | number of bytes/line in bitmap image |

```
Bitmap - convert grey-scale image to b&w bitmap.
#       Implemented in 68000 assembler by D. E. Germann.

#       Copyright (C) 1986, CFA Technologies, Inc.

#       entry   (a1.l) = input screen image address, 512 x 512 x 8.
#               (a2.l) = output bitmap address, 512 x 512 x 1, packed.
#               (d0.b) = black/white threshold.

#       exit    image packed.

#       uses    a - none
#               d - none

#       calls   none.
```

| | | | | | |
|---|---|---|---|---|---|
| 1 000000 48E7F760 | Bitmap | movem.l | a1-a2/d0-d3/d5-d7,-(sp) | save registers | |
| 1 000004 1600 | | move.b | d0,d3 | | |
| 1 000006 7CFF | | moveq | #-1,d6 | initialize bit accumulator | |
| 1 000008 3E3C8000 | | move.w | #1<<(16-1),d7 | bit counter | |
| 1 00000C 7AFF | | moveq | #-1,d5 | initialize bit mask | |
| 1 00000E 343C01FF | | move.w | #Border,d2 | | |
| 1 000012 3002 | | move.w | d2,d0 | y := 0 to Border | |
| 1 000014 3202 | bit1 | move.w | d2,d1 | x := 0 to Border | |
| 1 000016 E35E | bit2 | rol.w | #1,d6 | position accumulator for next bit | |
| 1 000018 B619 | | cmp.b | (a1)+,d3 | | |
| 1 00001A 53C5 | | sls | d5 | | |
| 1 00001C 5305 | | subq.b | #1,d5 | d5.w is FFFE if >= LS, FFFF if ... | |
| 1 00001E CC45 | | and.w | d5,d6 | clear output pixel if necessary | |

```
Address Object    Statement.
1 000020 E35F              rol.w    #1,d7                        advance output bit counter
1 000022 6B0E              bai.s    bit4                         if complete word
1 000024 51C9FFF0   bit3   dbra     d1,bit2                      if more bytes in this line
1 000028 51C8FFEA          dbra     d0,bit1                      if more lines to convert
1 00002C 4CDF06EF          movem.l  (sp)+,a1-a2/d0-d3/d5-d7      restore registers
1 000030 4E75              rts 1 000032 34C6       bit4   move.w   d5,(a2)+                     store word
1 000034 7CFF              moveq    #-1,d6                       reinitialize bit accumulator
1 000036 51C9FFDE          dbra     d1,bit2                      if more bytes in this line
1 00003A 51C8FFD8          dbra     d0,bit1                      if more lines to convert
1 00003E 4CDF06EF          movem.l  (sp)+,a1-a2/d0-d3/d5-d7      restore registers
1 000042 4E75              rts end 0 errors detected.
```

What is claimed is:

1. A method for operating programmable computing means to illumination equalize input pixel values of an array of input pixel values characteristic of a fingerprint image so as to produce an illumination equalized array of pixel values characteristic of an illumination equalized image, including:

receiving an array of input pixel values characteristic of a fingerprint image;

selecting equalizing subarrays of input pixel values, each including an input pixel value to be illumination equalized;

generating subarray average values as a function of the pixel values within the equalizing subarrays;

subtracting the subarray average values from the corresponding pixel values being equalized to generate pixel difference values;

adding a predetermined constant to the pixel difference values to generate intermediate illumination equalized pixel values;

setting the illumination equalized pixel values equal to a predetermined minimum pixel value if the corresponding intermediate illumination equalized pixel values are less than the minimum pixel value;

setting the illumination equalized pixel values equal to the corresponding intermediate illumination equalized pixel values if the corresponding intermediate illumination equalized pixel values are greater than or equal to the minimum pixel value, and less than or equal to a predetermined maximum pixel value;

setting the illumination equalized pixel values equal to the maximum pixel value if the corresponding intermediate illumination equalized pixel values are greater than the maximum pixel value; and storing the illumination equalized pixel values as an array of illumination equalized pixel values characteristic of the fingerprint image.

2. The method of claim 1 wherein selecting equalizing subarrays comprises selecting equalizing subarrays, each including an input pixel value to be illumination equalized and a plurality of input pixel values adjacent to and surrounding the pixel value to be illumination equalized.

3. The method of claim 2 wherein selecting equalizing subarrays comprises selecting eight-by-eight subarrays of input pixel values.

4. The method of claim 1 wherein generating subarray average values includes, for each subarray, summing the pixel values of the subarray and dividing the sum by the number of pixel values summed.

5. The method of claim 1 wherein adding a predetermined constant to the pixel difference values includes adding a constant determined as a function of noise in the fingerprint image.

6. The method of claim 1 wherein adding a predetermined constant includes adding a constant characteristic of an expected average illumination of the image.

7. The method of claim 1 wherein adding a predetermined constant includes adding a constant representative of a pixel value halfway between the maximum pixel value and the minimum pixel value.

* * * * *

UNITED STATES PATENT AND TRADEMARK OFFICE
CERTIFICATE OF CORRECTION

PATENT NO. : 4,811,414

DATED : March 7, 1989

INVENTOR(S) : Glenn M. Fishbine et al.

It is certified that error appears in the above-identified patent and that said Letters Patent is hereby corrected as shown below:

Insert the following before line 1 of the specification:

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Signed and Sealed this

Seventh Day of November, 1989

*Attest:*

JEFFREY M. SAMUELS

*Attesting Officer*     *Acting Commissioner of Patents and Trademarks*